(12) United States Patent
Pelletier et al.

(10) Patent No.: US 11,873,266 B2
(45) Date of Patent: *Jan. 16, 2024

(54) METHODS OF TREATING OR CONTROLLING CYTOTOXIC CEREBRAL EDEMA CONSEQUENT TO AN ISCHEMIC STROKE

(71) Applicant: Aeromics, Inc., New Haven, CT (US)

(72) Inventors: Marc F. Pelletier, Shaker Heights, OH (US); George William Farr, Rocky River, OH (US); Paul Robert McGuirk, Spring Hill, FL (US); Christopher H Hall, Shaker Heights, OH (US); Walter F. Boron, Shaker Heights, OH (US)

(73) Assignee: AEROMICS, INC., New Haven, CT (US)

( * ) Notice: Subject to any disclaimer, the term of this patent is extended or adjusted under 35 U.S.C. 154(b) by 73 days.

This patent is subject to a terminal disclaimer.

(21) Appl. No.: 17/443,361

(22) Filed: Jul. 26, 2021

(65) Prior Publication Data

US 2022/0081391 A1 Mar. 17, 2022

Related U.S. Application Data

(63) Continuation of application No. 15/982,644, filed on May 17, 2018, now Pat. No. 11,084,778, which is a continuation of application No. 14/398,947, filed as application No. PCT/US2013/040194 on May 8, 2013, now Pat. No. 9,994,514.

(60) Provisional application No. 61/799,606, filed on Mar. 15, 2013, provisional application No. 61/651,778, filed on May 25, 2012, provisional application No. 61/644,268, filed on May 8, 2012.

(51) Int. Cl.
| | |
|---|---|
| *A61K 31/24* | (2006.01) |
| *A61K 31/661* | (2006.01) |
| *A61K 31/6615* | (2006.01) |
| *A61K 31/167* | (2006.01) |
| *C07C 235/64* | (2006.01) |
| *C07D 295/185* | (2006.01) |
| *C07F 9/12* | (2006.01) |
| *A61K 31/5375* | (2006.01) |

(52) U.S. Cl.
CPC .......... *C07C 235/64* (2013.01); *A61K 31/167* (2013.01); *A61K 31/24* (2013.01); *A61K 31/5375* (2013.01); *A61K 31/661* (2013.01); *A61K 31/6615* (2013.01); *C07D 295/185* (2013.01); *C07F 9/12* (2013.01)

(58) Field of Classification Search
CPC .. A61K 31/167; A61K 31/24; A61K 31/5375; A61K 31/661; A61K 31/6615; C07C 235/64; A61P 1/16; A61P 13/12; A61P 25/00; A61P 25/06; A61P 25/08; A61P 27/02; A61P 3/00; A61P 3/10; A61P 3/12; A61P 39/00; A61P 43/00; A61P 7/10; A61P 9/04; A61P 9/10; C07F 9/12
See application file for complete search history.

(56) References Cited

U.S. PATENT DOCUMENTS

| | | | |
|---|---|---|---|
| 3,331,874 | A | 7/1967 | Stecker |
| 3,332,996 | A | 7/1967 | Zerweck et al. |
| 5,137,871 | A | 8/1992 | Wei |
| (Continued) | | | |

FOREIGN PATENT DOCUMENTS

| | | |
|---|---|---|
| CA | 2 108 794 C | 6/2003 |
| EP | 0 338 415 A2 | 10/1989 |
| (Continued) | | |

OTHER PUBLICATIONS

Roth, Pharmacology Notes, Proc (Baylor Univ Med. Cent), vol. 24(3), pp. 257-259, publ. 2011 (Year: 2011).*
U.S. Appl. No. 12/381,086, filed Mar. 6, 2009, Wood et al.
U.S. Appl. No. 14/398,947, filed Nov. 4, 2014, Pelletier et al.
U.S. Appl. No. 14/752,839, filed Jun. 27, 2015, Pelletier et al.
U.S. Appl. No. 16/296,663, filed Mar. 8, 2019, Pelletier et al.
U.S. Appl. No. 16/665,333, filed Oct. 28, 2019, Pelletier et al.
U.S. Appl. No. 17/099,435, filed Nov. 16, 2020, Pelletier et al.
U.S. Appl. No. 17/304,201, filed Jun. 16, 2021, Pelletier et al.

(Continued)

*Primary Examiner* — Sarah Pihonak
(74) *Attorney, Agent, or Firm* — Hoxie & Associates LLC

(57) ABSTRACT

The present invention relates to the use of selective aquaporin inhibitors, e.g., of aquaporin-4 or aquaporin-2, e.g., certain phenylbenzamide compounds, for the prophylaxis, treatment and control of aquaporin-mediated conditions, e.g., diseases of water imbalance, for example edema (particularly edema of the brain and spinal cord, e.g., following trauma or ischemic stroke, as well as the edema associated with glioma, meningitis, acute mountain sickness, epileptic seizures, infections, metabolic disorders, hypoxia, water intoxication, hepatic failure, hepatic encephalopathy, diabetic ketoacidosis, abscess, eclampsia, Creutzfeldt-Jakob disease, and lupus cerebritis, as well as edema consequent to microgravity and/or radiation exposure, as well as edema consequent to invasive central nervous system procedures, e.g., neurosurgery, endovascular clot removal, spinal tap, aneurysm repair, or deep brain stimulation, as well as retinal edema), as well as hyponatremia and excess fluid retention, and diseases such as epilepsy, retinal ischemia and other diseases of the eye associated with abnormalities in intraocular pressure and/or tissue hydration, myocardial ischemia, myocardial ischemia/reperfusion injury, myocardial infarction, myocardial hypoxia, congestive heart failure, sepsis, and neuromyelitis optica, as well as migraines, as well as to novel assays for identifying aquaporin inhibitors.

25 Claims, 14 Drawing Sheets

(56) References Cited

U.S. PATENT DOCUMENTS

| | | |
|---|---|---|
| 5,324,749 A | 6/1994 | Woog et al. |
| 5,486,530 A | 1/1996 | Boelke et al. |
| 5,519,035 A | 5/1996 | Maiese et al. |
| 5,741,671 A | 4/1998 | Agre |
| 5,858,702 A | 1/1999 | Agre |
| 5,905,090 A | 5/1999 | Bertolini et al. |
| 6,255,298 B1 | 7/2001 | Lysko et al. |
| 6,500,809 B1 | 12/2002 | Frazer |
| 7,601,745 B2 | 10/2009 | Leban et al. |
| 7,626,042 B2 | 12/2009 | Muto et al. |
| 7,659,312 B2 | 2/2010 | Nakada et al. |
| 7,671,058 B2 | 3/2010 | Tokuyama et al. |
| 7,700,655 B2 | 4/2010 | Muto et al. |
| 7,872,048 B2 | 1/2011 | Simard |
| 7,906,555 B2 | 3/2011 | Flynn et al. |
| 8,003,610 B2 | 8/2011 | Shaw et al. |
| 8,097,759 B2 | 1/2012 | Muto et al. |
| 8,263,657 B2 | 9/2012 | Muto et al. |
| 8,277,845 B2 | 10/2012 | Jacobson |
| 8,946,293 B2 | 2/2015 | Jacobson |
| 8,980,952 B2 | 3/2015 | Simard et al. |
| 9,573,885 B2 | 2/2017 | Pelletier et al. |
| 9,827,253 B2 | 11/2017 | Pelletier et al. |
| 9,949,991 B2 | 4/2018 | Pelletier et al. |
| 9,994,514 B2 | 6/2018 | Pelletier et al. |
| 10,004,703 B2 | 6/2018 | Jacobson et al. |
| 10,258,636 B2 | 4/2019 | Pelletier et al. |
| 10,894,055 B2 | 1/2021 | Pelletier et al. |
| 11,071,744 B2 | 7/2021 | Pelletier et al. |
| 11,084,778 B2 | 8/2021 | Pelletier et al. |
| 11,117,909 B2 | 9/2021 | McGuirk et al. |
| 2001/0046993 A1 | 11/2001 | Ikeda et al. |
| 2002/0061311 A1 | 5/2002 | Haas et al. |
| 2003/0215889 A1 | 11/2003 | Simard et al. |
| 2004/0259877 A1 | 12/2004 | Muto et al. |
| 2005/0085734 A1 | 4/2005 | Tehrani |
| 2005/0182012 A1 | 8/2005 | McEvoy et al. |
| 2005/0187300 A1 | 8/2005 | Bajji et al. |
| 2006/0014811 A1 | 1/2006 | Muto et al. |
| 2006/0019958 A1 | 1/2006 | Muto et al. |
| 2006/0035944 A1 | 2/2006 | Muto et al. |
| 2006/0094718 A1 | 5/2006 | Muto et al. |
| 2006/0100257 A1 | 5/2006 | Muto et al. |
| 2006/0111409 A1 | 5/2006 | Muto et al. |
| 2006/0167110 A1 | 7/2006 | Blume et al. |
| 2007/0254956 A1 | 11/2007 | Shudo et al. |
| 2007/0281978 A1 | 12/2007 | Nakada et al. |
| 2008/0125488 A1 | 5/2008 | Leverve et al. |
| 2008/0171719 A1 | 7/2008 | Chatterton et al. |
| 2008/0176822 A1 | 7/2008 | Chen |
| 2008/0214486 A1 | 9/2008 | Chatterton et al. |
| 2008/0221169 A1 | 9/2008 | Flynn et al. |
| 2008/0234233 A1 | 9/2008 | Muto et al. |
| 2009/0118350 A1 | 5/2009 | McLean |
| 2009/0163545 A1 | 6/2009 | Goldfarb |
| 2009/0239868 A1 | 9/2009 | Muto et al. |
| 2009/0239919 A1 | 9/2009 | Wood et al. |
| 2010/0016381 A1 | 1/2010 | Asakawa et al. |
| 2010/0113770 A1 | 5/2010 | Muto et al. |
| 2010/0125090 A1 | 5/2010 | Hadida Ruah et al. |
| 2010/0184856 A1 | 7/2010 | Lau et al. |
| 2010/0190796 A1 | 7/2010 | Verkman et al. |
| 2010/0274051 A1 | 10/2010 | Muto et al. |
| 2011/0052678 A1 | 3/2011 | Shantha et al. |
| 2011/0172195 A1 | 7/2011 | Flynn et al. |
| 2012/0010178 A1 | 1/2012 | Rubin et al. |
| 2012/0039805 A1 | 2/2012 | Lisanti et al. |
| 2012/0183600 A1 | 7/2012 | Chen |
| 2012/0196875 A1 | 8/2012 | Bouyssou et al. |
| 2012/0238623 A1 | 9/2012 | Chandraratna et al. |
| 2012/0245094 A1 | 9/2012 | Jacobsen et al. |
| 2012/0282591 A1 | 11/2012 | Thatte et al. |
| 2015/0133405 A1 | 5/2015 | Pelletier et al. |
| 2015/0166589 A1 | 6/2015 | Anderson et al. |
| 2015/0342967 A1 | 12/2015 | Pelletier et al. |
| 2016/0220680 A1 | 8/2016 | Itai et al. |
| 2016/0264604 A1 | 9/2016 | Pelletier et al. |
| 2016/0279155 A1 | 9/2016 | Pelletier et al. |
| 2016/0346302 A1 | 12/2016 | Pelletier et al. |
| 2017/0216321 A1 | 8/2017 | Jacobson et al. |
| 2018/0042873 A1 | 2/2018 | Pelletier et al. |
| 2018/0155727 A1 | 6/2018 | Simard et al. |
| 2018/0169118 A1 | 6/2018 | Pelletier et al. |
| 2019/0185496 A1 | 6/2019 | McGuirk et al. |
| 2019/0307779 A1 | 10/2019 | Pelletier et al. |
| 2021/0275549 A1 | 9/2021 | Pelletier et al. |
| 2022/0143048 A1 | 5/2022 | Pelletier et al. |
| 2022/0204536 A1 | 6/2022 | McGuirk et al. |

FOREIGN PATENT DOCUMENTS

| | | |
|---|---|---|
| EP | 1 352 650 A1 | 10/2003 |
| EP | 1 510 210 A1 | 3/2005 |
| EP | 1 512 397 A1 | 3/2005 |
| EP | 1 514 544 A1 | 3/2005 |
| EP | 1 535 609 A1 | 6/2005 |
| EP | 1 555 018 A1 | 7/2005 |
| EP | 1 649 852 A1 | 4/2006 |
| EP | 2 201 946 A1 | 6/2010 |
| RU | 2 461 375 C1 | 9/2012 |
| WO | WO 99/07382 A1 | 2/1999 |
| WO | WO 01/23399 A1 | 4/2001 |
| WO | WO 02/49632 A1 | 6/2002 |
| WO | WO 2004/006858 A2 | 1/2004 |
| WO | WO 2006/036278 A2 | 4/2006 |
| WO | WO 2006/074127 A2 | 7/2006 |
| WO | WO 2007/084464 A2 | 7/2007 |
| WO | WO 2007/143689 A2 | 12/2007 |
| WO | WO 2008/046014 A1 | 4/2008 |
| WO | WO 2008/052190 A2 | 5/2008 |
| WO | WO 2008/060705 A2 | 5/2008 |
| WO | WO 2008/089103 A2 | 7/2008 |
| WO | WO 2008/089212 A1 | 7/2008 |
| WO | WO 2008/098160 A1 | 8/2008 |
| WO | WO 2008/100636 A2 | 8/2008 |
| WO | WO 2008/133884 A2 | 11/2008 |
| WO | WO 2009/002832 A2 | 12/2008 |
| WO | WO 2009/006555 A2 | 1/2009 |
| WO | WO 2009/054439 A1 | 4/2009 |
| WO | WO 2009/073711 A1 | 6/2009 |
| WO | WO 2009/074809 A1 | 6/2009 |
| WO | WO 2009/097443 A2 | 8/2009 |
| WO | WO 2009/139925 A1 | 11/2009 |
| WO | WO 2010/033560 A2 | 3/2010 |
| WO | WO 2010/048273 A2 | 4/2010 |
| WO | WO 2010/101648 A1 | 9/2010 |
| WO | WO 2011/112791 A1 | 9/2011 |
| WO | WO 2012/012347 A2 | 1/2012 |
| WO | WO 2012/150857 A1 | 11/2012 |
| WO | WO 2013/052844 A1 | 4/2013 |
| WO | WO 2013/152313 A1 | 10/2013 |
| WO | WO 2013/165606 A1 | 11/2013 |
| WO | WO 2015/037659 A1 | 3/2015 |
| WO | WO 2015/069948 A1 | 5/2015 |
| WO | WO 2015/069956 A2 | 5/2015 |
| WO | WO 2015/069961 A1 | 5/2015 |
| WO | WO 2016/077787 A1 | 5/2016 |
| WO | WO 2016/196113 A1 | 12/2016 |
| WO | WO 2017/062765 A1 | 4/2017 |
| WO | WO 2017/197371 A1 | 11/2017 |
| WO | WO 2018/023035 A1 | 2/2018 |
| WO | WO 2022/028459 A1 | 2/2022 |

OTHER PUBLICATIONS

U.S. Appl. No. 17/460,061, filed Aug. 27, 2021, McGuirk et al.
Abir-Awan, M. et al., "Inhibitors of Mammalian Aquaporin Water Channels," International Journal of Molecular Sciences, 2019, 20, 1589, 22 pages, doi:10.3390/ijms20071589.
Aeromics, Anti-Edema Therapy for Patients Affected by Disabling and Life-Threatening Severe Ischemic Stroke, 7 pages, retrieved on Aug. 5, 2020, from: https://www.aeromics.com/.

(56) References Cited

OTHER PUBLICATIONS

Aeromics, "Aeromics Initiates Phase 1 Clinical Trial of CNS Edema Inhibitor AER-271 in Healthy Human Volunteers," dated Jul. 9, 2018, 4 pages, retrieved on Aug. 5, 2020, from: https://www.aeromics.com/press-releases/aeromics-inc-initiates-phase-1-trial-of-aer-271-in-healthy-human-volunteers.
Aeromics, "Aeromics, Inc. Appoints Pharmaceutical and Biotech Veterans Mark Day, Ph.D. and Thomas Zindrick, J.D. to Its Board of Directors," dated Aug. 16, 2018, 7 pages, retrieved on Aug. 5, 2020, from: https://www.aeromics.com/press-releases/aeromics-inc-appoints-pharmaceutical-and-biotech-veterans-mark-day-phd-and-thomas-zindrick-jd-to-its-board-of-directors.
Aeromics, "Aeromics, Inc. Appoints Nobel Laureate Peter Agre to Its Board of Directors," dated Sep. 2019, 4 pages, retrieved on Aug. 5, 2020, from: https://www.aeromics.com/pr-090919-p-agre-director.
Aeromics, "Aeromics and Simcere Announce Collaboration and License Agreement for AER-271 in Greater China," dated Nov. 2019, 4 pages, retrieved on Aug. 5, 2020, from: https://www.aeromics.com/pr-110519-simcere.
Aeromics, "Aeromics, Inc. Appoints Joseph Schindler, M.D. as Chief Medical Officer," dated Jan. 2020, 1 page, retrieved on Sep. 23, 2020, from: https://www.aeromics.com/pr-010720-schindler.
Alexander, J. et al., "Administration of the Soluble Complement Inhibitor, Crry-Ig, Reduces Inflammation and Aquaporin 4 Expression in Lupus Cerebritis," Biochimica et Biophysica Acta, 2003, 1639, 169-176.
Amiry-Moghaddam, M. et al., "Alpha-Syntrophin Deletion Removes the Perivascular But Not Endothelial Pool of Aquaporin-4 at the Blood-Brain Barrier and Delays the Development of Brain Edema in an Experimental Model of Acute Hyponatremia," The FASEB Journal, 2004, 18, 542-544.
Amiry-Moghaddam, M. et al. "Anchoring of Aquaporin-4 in Brain: Molecular Mechanisms and Implications for the Physiology and Pathophysiology of Water Transport," Neuroscience, 2004, 129, 999-1010.
Aoki, K. et al., "Enhanced Expression of Aquaporin 4 in Human Brain with Infarction," Acta Neuropathologica, 2003, 106, 121-124.
Aoki-Yoshino, K. et al., "Enhanced Expression of Aquaporin 4 in Human Brain with Inflammatory Diseases," Acta Neuropathologica, 2005, 110, 281-288.
Ayasoufi, K. et al., "Aquaporin 4 Blockade Improves Survival of Murine Heart Allografts Subjected to Prolonged Cold Ischemia," American Journal of Transplantation, 2018, 18, 1238-1246.
Banamine (Flunixin Meglumine), retrieved from https://web.archive.org/web/20110711140225/http://www.banamine.com/research/FlunixinMeglumine.asp, 1 page, face of article states: Jul. 11, 2011.
Bao, W. et al., "Selective mGluR5 Receptor Antagonist or Agonist Provides Neuroprotection in a Rat Model of Focal Cerebral Ischemia," Brain Research, 2001, 922, 173-179.
Baraldo, M. et al., "*Steroid-free* and *Steroid Withdrawal* Protocols in Heart Transplantation: The Review of Literature," Transplant International, 2014, 515-529.
Bardutzky, J. et al., "Antiedema Therapy in Ischemic Stroke," Stroke, 2007, 38, 3084-3094.
Beeton, C. et al., "Induction and Monitoring of Active Delayed Type Hypersensitivity (DTH) in Rats," JoVe. 6. http://www.jove.com/index/Details.stp?ID=237, doi:10.3791/237, copyright 2007, 2 pages.
Benga, O. et al., "Brain Water Channel Proteins in Health and Disease," Molecular Aspects of Medicine, 2012, 33, 562-578.
Bereczki, D. et al., "Cochrane Report: A Systematic Review of Mannitol Therapy for Acute Ischemic Stroke and Cerebral Parenchymal Hemorrhage," Stroke, 2000, 31, 2719-2722.
Bhattacharyya, S. et al., "Specific Effects of BCL10 Serine Mutations on Phosphorylations in Canonical and Noncanonical Pathways of NF-κB Activation Following Carrageenan," The American Journal of Physiology—Gastrointesintal and Liver Physiology, 2011, 301, G475-G486.
Binder, D. et al., "Increased Seizure Threshold in Mice Lacking Aquaporin-4 Water Channels," NeuroReport, 2004, 15 (2), 259-262.
Binder, D. et al., "Increased Seizure Duration and Slowed Potassium Kinetics in Mice Lacking Aquaporin-4 Water Channels," GLIA, 2006, 53, 631-636.
Binder, D. et al., "Aquaporin-4 and Epilepsy," GLIA, 2012, 60, 1203-1214.
Bloch, O. et al., "Aquaporin-4 Gene Deletion in Mice Increases Focal Edema Associated with *Staphylococcal* Brain Abscess," Journal of Neurochemistry, 2005, 95, 254-262.
Brown, L. et al., "In Vitro and In Vivo Hydrolysis of Salicy lanilide N-Methylcarbamate and 4-Bipheny N-Methylcarbamate," Journal of Pharmaceutical Sciences, 1972, 61 (6), 858-860.
Caraci, F. et al., "Metabotropic Glutamate Receptors in Neurodegeneration/Neuroprotection: Still a Hot Topic?," Neurochemistry International, 2012, 61, 559-565.
Cernak, I., "Animal Models of Head Trauma," NeuroRx, 2005, 2, 410-422.
Chen, C. et al., "Animal Models of Nervous System Diseases," Jilin Science and Technology Press, 2007, pp. 252-254.
Chiamulera, C. et al., "Activation of Metabotropic Receptors has a Neuroprotective Effect in a Rodent Model of Focal Ischaemia," European Journal of Pharmacology, 1992, 216, 335-336.
Colucci, M. et al., "In Vitro Clot Lysis as a Potential Indicator of Thrombus Resistance to Fibrinolysis—Study in Healthy Subjects and Correlation with Blood Fibrinolytic Parameters," Thrombosis and Haemostasis, 1997, 77 (4), 725-729.
Cooper, G. et al., "Transport of Volatile Solutes Through AQP1," Journal of Physiology, 2002, 542.1, 17-29.
Costanzo, M., "The International Society of Heart and Lung Transplantation Guidelines for the Care of Heart Transplant Recipients," The Journal of Heart and Lung Transplantation, 2010, 29 (8), 914-956.
CRASH Trial, "Effect of Intravenous Corticosteroids on Death within 14 Days in 10008 Adults with Clinically Significant Head Injury (MRC CRASH Trial): Randomised Placebo Controlled Trial," Lancet, 2004, 264, 1321-1328.
Cummins, E. et al., "Prolyl Hydroxylase-1 Negatively Regulates IκB Kinase-β, Giving Insight into Hypoxia-induced NFκB Activity," Proceedings of the National Academy of Sciences, 2006, 103 (48), 18154-18159.
Da, T. et al., "Aquaporin-4 Gene Disruption in Mice Protects Against Impaired Retinal Function and Cell Death after Ischemia," Investigative Ophthalmology & Visual Science, 2004, 45 (12), 4477-4483.
Davis, M. et al., "State of the Art: Cardiac Transplantation," Trends in Cardiovascular Medicine, 2014, 24, 341-349.
Dearden, N. et al., "Effect of High-Dose Dexamethasone on Outcome from Severe Head Injury," Journal of Neurosurgery, 1986, 64, 81-88.
Di Renzo, G. et al., "Why have Ionotropic and Metabotropic Glutamate Antagonists Failed in Stroke Therapy?," in New Strategies in Stroke Intervention, L. Annunziato, Ed., Humana Press, 2009, pp. 13-25.
Dibas, A. et al., "Changes in Ocular Aquaporin-4 (AQP4) Expression Following Retinal Injury," Molecular Vision, 2008, 14, 1770-1783.
Ding, F., Neurobiology, Science Press, 2007, pp. 421-423.
Ding, T. et al., "Knockdown a Water Channel Protein, Aquaporin-4 Induced Glioblastoma Cell Apoptosis," PLoS ONE, 2013, 8 (8), e66751, 9 pages, doi: 10.1371/journal.pone.0066751.
Dixon, C. et al., "A Controlled Cortical Impact Model of Traumatic Brain Injury in the Rat," Journal of Neuroscience Methods, 1991, 39, 253-262.
Dudek, F. et al., "Regulation of Brain Water: Is there a Role for Aquaporins in Epilepsy?," Epilepsy Currents, 2005, 5 (3), 104-106, retrieved on Jul. 22, 2015, from http://www.ncbi.nlm.nih.gov/pmc/articles/PMC1198631/.
Dvirnik, N. et al., "Steroids in Cardiac Surgery: A Systematic Review and Meta-analysis," British Journal of Anaesthesia, 2018, 120 (4), 657-667.
Eid, T. et al., "Loss of Perivascular Aquaporin 4 May Underlie Deficient Water and $K^+$ Homeostasis in the Human Epileptogenic Hippocampus," Proceedings of the National Academy of Sciences, 2005, 102 (4), 1193-1198.

(56) References Cited

OTHER PUBLICATIONS

Eisenberg, H. et al., "High-Dose Barbiturate Control of Elevated Intracranial Pressure in Patients with Severe Head Injury," Journal of Neurosurgery, 1988, 69, 15-23.
Elati, C. et al., "Novel Synthesis of Fosphenytoin: Anti-Convulsant Prodrug," Synthetic Communications, 2008, 38, 2950-2957.
Engel, O. et al., "Modeling Stroke in Mice—Middle Cerebral Artery Occlusion with the Filament Model," Journal of Visualized Experiments, 2011, 47, e2423, 5 pages, doi: 10.3791/2423.
English-language translation of Abaturov, A. et al., "Molecular Mechanisms of Nonspecific Protection of the Respiratory Tract (Continuation, beginning in No. 3, 2006) 2. Pathophysiological Significance of Transcription Factors NF-KB," Zhurnal "Zdorovie Rebenka" (Journal "Child's Health"), 2007, 1 (4), 14 pages.
English-language translation of Nimer, S. et al., "Edema as a Basic Response of the Vascular Component of Brain Perfusion Systems in Traumatic Brain Injury," Problems of Health and Ecology, 2007, 10 pages.
Esteva-Font, C. et al., "Experimental Evaluation of Proposed Small-Molecule Inhibitors of Water Channel Aquaporin-1," Molecular Pharmacology, 2016, 89, 686-693.
Farinas, J. et al., "Plasma Membrane Water Permeability of Cultured Cells and Epithelia Measured by Light Microscopy with Spatial Filtering," The Journal of General Physiology, 1997, 110, 283-296.
Farr, G. et al., "Aquaporin-4 Inhibitor AER-270 and Its Prodrug AER-271 Reduce Cerebral Edema and Improve Outcomes in Two Models of CNS Injury," Abstract M1905, Annals of Neurology, 2014, 76 (Supplement 18), S126-S127.
Farr, G. et al., "Phenylbenzamide Derivatives AER-270/271 Inhibit Aquaporin-4 Reducing Cerebral Edema and Improving Outcome in Two Models of CNS Injury," Poster presented at 2014 American Neurological Association Annual Meeting, 1 page.
Farr, G. et al., "Functionalized Phenylbenzamides Inhibit Aquaporin-4 Reducing Cerebral Edema and Improving Outcome in Two Models of CNS Injury," Neuroscience, 2019, accepted manuscript, https://doi.org/10.1016/j.neuroscience.2019.01.034, 46 pages.
Fei, Z. et al., "Metabotropic Glutamate Receptor Antagonists and Agonists: Potential Neuroprotectors in Diffuse Brain Injury," Journal of Clinical Neuroscience, 2006, 13, 1023-1027.
Fischer, U. et al., "The Antioxidant N-Acetylcysteine Preserves Myocardial Function and Diminishes Oxidative Stress After Cardioplegic Arrest," The Journal of Thoracic and Cardiovascular Surgery, 2003, 126 (5), 1483-1488.
Fomovska, A. et al., "Salicylanilide Inhibitors of *Toxoplasma gondii*," NIH Public Access, Author Manuscript, available in PMC 2013, 40 pages, face of article states: Published in final edited form as: *J Med Chem*. Oct. 1, 20121; 55(19): 8375-8391. doi: 10.1021/jm3007596.
Frigeri, A. et al., "Localization of MIWC and GLIP Water Channel Homologs in Neuromuscular, Epithelial and Glandular Tissues," Journal of Cell Science, 1995, 108, 2993-3002.
Frigeri, A et al., "Immunolocalization of the Mercurial—Insensitive Water Channel and Glycerol Intrinsic Protein in Epithelial Cell Plasma Membranes," Proceedings of the National Academy of Sciences, 1995, 92, 4328-4331.
Fukuda, A. et al., "Aquaporin 4: A Player in Cerebral Edema and Neuroinflammation," Journal of Neuroinflammation, 2012, 9:279, 9 pages, doi: 10.1186/1742-2094-9-279.
Gerber, J. et al., "Mechanisms of Injury in Bacterial Meningitis," Current Opinion in Neurology, 2010, 23, 312-318.
Gomez-Cabrero, A et al., "IMD-0354 Targets Breast Cancer Stem Cells: A Novel Approach for an Adjuvant to Chemotherapy to Prevent Multidrug Resistance in a Murine Model," PLOS One, 2013, 8 (8), e73607, 14 pages, doi:10.1371/journal.pone.0073607.
Gotoh, O. et al., "Ischemic Brain Edema Following Occlusion of the Middle Cerebral Artery in the Rat. I: The Time Courses of the Brain Water, Sodium and Potassium Contents and Blood Brain Barrier Permeability to [125]I-Albumin," Stroke, 1985, 16 (1), 101-109.

Gullans, S., "Control of Brain vol. During Hyperosmolar and Hypoosmolar Conditions," Annual Review of Medicine, 1993, 44, 289-301.
Gunnarson, E. et al., "Identification of a Molecular Target for Glutamate Regulation of Astrocyte Water Permeability," Glia, 2008, 56, 587-596.
Gunnarson, E. et al., "Erythropoietin Modulation of Astrocyte Water Permeability as a Component of Neuroprotection," Proceedings of the National Academy of Sciences, 2009, 106 (5), 1602-1607.
Guo, Q. et al., "Progesterone Administration Modulates AQP4 Expression and Edema After Traumatic Brain Injury in Male Rats," Experimental Neurology, 2006, 198, 469-478.
Hall, G. et al., "Inhibitor-κB Kinase-β Regulates LPS-Induced TNF-α Production in Cardiac Myocytes Through Modulation of NF-κB p65 Subunit Phosphorylation," American Journal of Heart Physiology—Heart and Circulatory Physiology, 2005, 289, H2103-H2111.
Haller, M. et al., "Steroid Avoidance or Withdrawal for Kidney Transplant Recipients (Review)," Cochrane Database of Systematic Reviews, 2016, Issue 8, Art. No. CD005632, Doi: 10.1002/14651858.CD005632.pub3, 167 pages.
Himadri, P. et al., "Role of Oxidative Stress and Inflammation in Hypoxia-Induced Cerebral Edema: A Molecular Approach," High Altitude Medicine & Biology, 2010, 11 (3), 231-244.
Hiroaki, Y. et al., "Implications of the Aquaporin-4 Structure on Array Formation and Cell Adhesion," Journal of Molecular Biology, 2006, 355, 628-639.
Ho, J. et al., "Crystal Structure of Human Aquaporin 4 at 1.8 Å and Its Mechanism of Conductance," Proceedings of the National Academy of Sciences, 2009, 106 (18), 7437-7442.
Hsu, M. et al., "Potential Role of the Glial Water Channel Aquaporin-4 in Epilepsy," Neuron Glia Biology, 2008, doi: 10.1017/S1740925X08000112, 11 pages.
Huang, Y. et al., "The Dual Role of AQP4 in Cytotoxic and Vasogenic Edema Following Spinal Cord Contusion and Its Possible Association with Energy Metabolism via COX5A," Frontiers in Neuroscience, 2019, 13:584, 15 pages, doi:10.3389/fnins.2019.00584.
Huber, V. et al., "Identification of Arylsulfonamides as Aquaporin 4 Inhibitors," Bioorganic & Medicinal Chemistry Letters, 2007, 17, 1270-1273.
Huber, V. et al., "Identification of Aquaporin 4 Inhibitors Using in vitro and in silico Methods," Bioorganic & Medicinal Chemistry, 2009, 17, 411-417.
Huber, V. et al., "Inhibition of Aquaporin 4 by Antiepileptic Drugs," Bioorganic & Medicinal Chemistry, 2009, 17, 418-424.
Igarashi, H. et al., "Pretreatment with a Novel Aquaporin 4 Inhibitor, TGN-020, Significantly Reduces Ischemic Cerebral Edema," Neurological Sciences, 2011, 32, 113-116.
Ikeshima-Kataoka, H., "Neuroimmunological Implications of AQP4 in Astrocytes," International Journal of Molecular Sciences, 2016, 17, 1306, 16 pages, doi: 10.3390/ijms17081306.
Illarionova, N. et al., "Functional and Molecular Interactions Between Aquaporins and Na,K-ATPase," Neuroscience, 2010, 168, 915-925.
Inayama, M. et al., "A Novel IκB Kinase-β Inhibitor Ameliorates Bleomycin-induced Pulmonary Fibrosis in Mice," American Journal of Respiratory and Critical Care Medicine, 2006, 173, 1016-1022.
International Preliminary Report on Patentability for International Application No. PCT/US2013/040194, dated Nov. 11, 2014, 8 pages.
International Search Report for International Application No. PCT/US2013/040194, dated Dec. 20, 2013, 5 pages.
International Search Report for International Application No. PCT/US2014/064432, dated Apr. 13, 2015, 5 pages.
International Search Report for International Application No. PCT/US2014/064441, dated Feb. 13, 2015, 4 pages.
International Search Report for International Application No. PCT/US2014/064447, dated Apr. 6, 2015, 5 pages.
International Search Report for International Application No. PCT/US2015/060731, dated Jan. 29, 2016, 4 pages.
International Search Report for International Application No. PCT/US2017/032563, dated Aug. 24, 2017, 3 pages.

(56) References Cited

OTHER PUBLICATIONS

Ito, J. et al., "Characterization of Edema by Diffusion-Weighted Imaging in Experimental Traumatic Brain Injury," Journal of Neurosurgery, 1996, 84, 97-103.
Ito, H. et al., "Interleukin-1-β Induces the Expression of Aquaporin-4 Through a Nuclear Factor-κB Pathway in Rat Astrocytes," Journal of Neurochemistry, 2006, 99, 107-118.
Janssens, S. et al., "TNF-alpha and Interferon-gamma Upregulate AQP4 Protein Expression in ARPE-19, a Human Retinal Pigmented Epithelial Cell Line," Acta Ophthalmologica, 2007, 85, Issue s240, abstract only, 2 pages, retrieved on Nov. 18, 2020, from: https://onlinelibrary.wiley.com/doi/abs/10.1111/j.1600-0420.2007.01063_3298.x.
Jeyaseelan, K. et al., "Aquaporins: A Promising Target for Drug Development," Expert Opinion on Therapeutic Targets, 2006, 10 (6), 889-909.
Johannesdottir, S. et al., "Use of Glucocorticoids and Risk of Venous Thromboembolism," JAMA Internal Medicine, 2013, 173 (9), 743-752.
Juenemann, M. et al., "Aquaporin-4 Autoantibodies Increase Vasogenic Edema Formation and Infarct Size in a Rat Stroke Model," BMC Immunology, 2015, 16:30, 7 pages, doi: 10.1186/s12865-015-0087-y.
Jung, J. et al., "Molecular Characterization of an Aquaporin cDNA from Brain: Candidate Osmoreceptor and Regulator of Water Balance," Proceedings of the National Academy of Sciences, 1994, 91, 13052-13056.
Jüttler, E. et al., "Clinical Review: Therapy for Refractory Intracranial Hypertension in Ischaemic Stroke," Critical Care, 2007, 11, 231, 14 pages, doi: 10.1186/cc6087.
Kalita, J. et al., "Current Status of Osmotherapy in Intracerebral Hemorrhage," Neurology India, 2003, 51 (1), 104-109.
Kamegawa, A. et al., "Two-dimensional Crystal Structure of Aquaporin-4 Bound to the Inhibitor Acetazolamide," Microscopy, 2016, 65 (2), 177-184.
Kamon, J. et al., "A Novel IKKα Inhibitor Stimulates Adiponectin Levels and Ameliorates Obesity-Linked Insulin Resistance," Biochemical and Biophysical Research Communications, 2004, 323, 242-248.
Katada, R. et al., "Greatly Improved Survival and Neuroprotection in Aquaporin-4-Knockout Mice Following Global Cerebral Ischemia," The FASEB Journal, 2014, 28, 10 pages, face of article states: published online Nov. 1, 2013, doi: 10.1096/fj.13-231274.
Kaufmann, A. et al., "Ischemic Core and Penumbra in Human Stroke," Stroke, 1999, 30, 93-99.
Ke, C. et al., "Heterogeneous Responses of Aquaporin-4 in Oedema Formation in a Replicated Severe Traumatic Brain Injury Model in Rats," Neuroscience Letters, 2001, 301, 21-24.
Kiening, K. et al., "Decreased Hemispheric Aquaporin-4 is Linked to Evolving Brain Edema Following Controlled Cortical Impact Injury in Rats," Neuroscience Letters, 2002, 324, 105-108.
Kim, H. et al., "Preoperative Corticosteroid Use and Early Postoperative Bronchial Anastomotic Complications after Lung Transplantation," The Korean Journal of Thoracic and Cardiovascular Surgery, 2018, 51, 384-389.
Kirby, A. et al., "The Reactivity of Phosphate Esters. Monoester Hydrolysis," Journal of the American Chemical Society, 1967, 89 (2), 415-423.
Kitchen, P. et al., "Targeting Aquaporin-4 Subcellular Localization to Treat Central Nervous System Edema," Cell, 2020, 181, 784-799.
Kochanek, P. et al., "Operation Brain Trauma Therapy: 2016 Update," Military Medicine, 2018, 183, 303-312.
Krave, U. et al., "Transient, Powerful Pressures are Generated in the Brain by a Rotational Acceleration Impulse to the Head," European Journal of Neuroscience, 2005, 21, 2876-2882.
Laird, M. et al., "Curcumin Attenuates Cerebral Edema Following Traumatic Brian Injury in Mice: A Possible Role for Aquaporin-4?," Journal of Neurochemistry, 2010, 113, 637-648.
Lea, P. et al., "Neuroprotective Activity of the mGluR5 Antagonists MPEP and MTEP Against Acute Excitotoxicity Differs and Does Not Reflect Actions at mGluR5 Receptors," British Journal of Pharmacology, 2005, 145 (4), 527-534.
Lee, D. et al., "Decreased Expression of the Glial Water Channel Aquaporin-4 in the Intrahippocampal Kainic Acid Model of Epileptogenesis," Experimental Neurology, 2012, doi: 10.1016/j.expneurolo.2012.02.002, 10 pages.
Lennikov, A. et al., "Amelioration of Endotoxin-induced Uveitis Treated with an IκB Kinase β Inhibitor in Rats," Molecular Vision, 2012, 18, 2586-2597.
Lennikov, A. et al., "Selective IKK2 Inhibitor IMD0354 Disrupts NF-KB Signaling to Suppress Corneal Inflammation and Angiogenesis," Angiogenesis, 2018, 21, 267-285.
Lennon, V. et al., "IgG Marker of Optic-Spinal Multiple Sclerosis Binds to the Aquaporin-4 Water Channel," The Journal of Experimental Medicine, 2005, 202 (4), 473-477.
Li, J. et al., "Synthesis and Biological Evaluation of a Water Soluble Phosphate Prodrug of 3-Aminopyridine-2-carboxaldehyde Thiosemicarbazone (3-AP)," Bioorganic & Medicinal Chemistry Letters, 1998, 8, 3159-3164.
Li, L. et al., "Greatly Attenuated Experimental Autoimmune Encephalomyelitis in Aquaporin-4 Knockout Mice," BMC Neuroscience, 2009, 10, 94, 5 pages, doi:10.1186/1471-2202-10-94.
Li, L. et al., "Proinflammatory Role of Aquaporin-4 in Autoimmune Neuroinflammation," The FASEB Journal, 2011, 25, 1556-1566.
Li, W. et al., "Curcumin by Down-Regulating NF-KB and Elevating Nrf2, Reduces Brain Edema and Neurological Dysfunction after Cerebral I/R," Microvascular Research, 2016, 106, 117-127.
Li, Y-R. et al., "Study of the Inhibitory Effects on TNF-α-induced NF-κB Activation of IMD0354 Analogs," Chemical Biology & Drug Design, 2017, 90, 1307-1311.
Loane, D. et al., "Activation of Metabotropic Glutamate Receptor 5 Modulates Microglial Reactivity and Neurotoxicity by Inhibiting NADPH Oxidase," The Journal of Biological Chemistry, 2009, 284 (23), 15629-15639.
Longa, E. et al., "Reversible Middle Cerebral Artery Occlusion Without Craniectomy in Rats," Stroke, 1989, 20, 84-91.
Ma, T. et al., "Generation and Phenotype of a Transgenic Knockout Mouse Lacking the Mercurial-Insensitive Water Channel Aquaporin-4," Journal of Clinical Investigation, 1997, 100 (5), 957-962.
Maddahi, A. et al., "The Role of Tumor Necrosis Factor-α and TNF-α Receptors in Cerebral Arteries Following Cerebral Ischemia in Rat," Journal of Neuroinflammation, 2011, 8:107, 13 pages, doi: 10.1186/1742-2094-8-107.
Manley, G. et al., "Aquaporin-4 Deletion in Mice Reduces Brain Edema After Acute Water Intoxication and Ischemic Stroke," Nature Medicine, 2000, 6 (2), 159-163.
Manley, G. et al., "New Insights into Water Transport and Edema in the Central Nervous System from Phenotype Analysis of Aquaporin-4 Null Mice," Neuroscience, 2004, 129, 983-991.
Marmarou, A. et al., "Traumatic Brain Edema in Diffuse and Focal Injury: Cellular or Vasogenic?," Acta Neurochirurgica, 2006 [Supplement], 96, 24-29.
Mcanally, K. et al., "Effect of Pre-transplantation Prednisone on Survival After Lung Transplantation," The Journal of Heart and Lung Transplantation, 2006, 25, 67-74.
Mehlhorn, U. et al., "Myocardial Fluid Balance," European Journal of Cardio-thoracic Surgery, 2001, 20, 1220-1230.
Meli, E. et al., "Activation of mGlu1 but not mGlu5 Metabotropic Glutamate Receptors Contributes to Postischemic Neuronal Injury In Vitro and In Vivo," Pharmacology, Biochemistry and Behavior, 2002, 73, 439-446.
Migliati, E. et al., "Inhibition of Aquaporin-1 and Aquaporin-4 Water Permeability by a Derivative of the Loop Diuretic Bumetanide Acting at an Internal Pore-Occluding Binding Site," Molecular Pharmacology, 2009, 76 (1), 105-112.
Mola, M. et al., "Automated Cell-Based Assay for Screening of Aquaporin Inhibitors," Analytical Chemistry, 2009, 81, 8219-8229.
Mola, M. et al., "Automated Cell-Based Assay for Screening of Aquaporin Inhibitors," Author Manuscript, available in PMC 2010, 24 pages, face of article states: Published in final edited form as: Anal Chem. Oct. 1, 2009; 81(19): 8219-8229. doi: 10.1021/ac901526k.

(56) References Cited

OTHER PUBLICATIONS

Monai, H. et al., "Adrenergic Receptor Antagonism Induces Neuroprotection and Facilitates Recovery from Acute Ischemic Stroke," Proceedings of the National Academy of Sciences, 2019, 116 (22), 11010-11019.

Morimoto, Y. et al., "Acute Brain Swelling After Out-of-Hospital Cardiac Arrest: Pathogenesis and Outcome," Critical Care Medicine, 1993, 21 (1), 104-110.

Mudge, D., "Avoiding or Stopping Steroids in Kidney Transplant Recipients: Sounds Good But Does It Work?," Cochrane Database of Systematic Reviews, 2016, 8, ED000114, https://doi.org/10.1002/14651858.ED000114, 2 pages.

Neely, J. et al., "Syntrophin-Dependent Expression and Localization of Aquaporin-4 Water Channel Protein, " Proceedings of the National Academy of Sciences, 2001, 98 (24), 14108-14113.

Nicosia, M. et al., "Aquaporin 4 Blockade Alters T Cell Trafficking Through a Novel Mechanism of S1PR1 Regulation," The Journal of Immunology, 2018, 200 (1 Supplement) 55.33, abstract only, 4 pages, retrieved on Oct. 10, 2018, from: http://www.jimmunol.org/content/200/1_Supplement/55.33.

Nicosia, M. et al., "Aquaporin 4 Inhibition Alters Chemokine Receptor Expression and T Cell Trafficking," Scientific Reports, 2019, 9:7417, 11 pages, https://doi.org/10.1038/s41598-019-43884-2.

Nimer, S. et al., "Edema as a Basic Response of the Vascular Component of Brain Perfusion Systems in Traumatic Brain Injury," Problems of Health and Ecology, 2007, 61-65.

Nishikawa, S. et al., "A Molecular Targeting Against Nuclear Factor-κB, as a Chemotherapeutic Approach for Human Malignant Mesothelioma," Cancer Medicine, 2014, 3 (2), 416-425.

Nordén, R. et al., "Activation of Host Antiviral RNA-sensing Factors Necessary for Herpes Simplex Virus Type 1-Activated Transcription of Host Cell Fucosyltransferase Genes FUT3, FUT5, and FUT6 and Subsequent Expression of sLex in Virus-Infected Cells," Glycobiology, 2009, 19 (7), 776-788.

Nordqvist, C. "Everything You Need to Know About Infections," Medical News Today, face of article states: Last update Tue Aug. 22, 2017, 11 pages retrieved on Nov. 26, 2018, from http://www.medicalnewstoday.com/articles/196271.php.

Ogawa, M. et al., "The Mechanism of Anti-Inflammatory Effects of Prostaglandin $E_2$ Receptor 4 Activation in Murine Cardiac Transplantation, " Transplantation, 2009, 87, 1645-1653.

Onai, Y. et al., "Inhibition of IκB Phosphorylation in Cardiomyoctyes Attenuates Myocardial Ischemia/Reperfusion Injury," Cardiovascular Research, 2004, 63, 51-59.

Onai, Y. et al., "Inhibition of NF-κB improves Left Ventricular Remodeling and Cardiac Dysfunction after Myocardial Infarction," American Journal of Heart Physiology—Heart and Circulatory Physiology, 2007, 292, H530-H538.

Pallan, T. et al., "Glyburide in Treating Malignant Cerebral Edema. Blocking Sulfonyl Urea One (SUR1) Receptors," Journal of Vasuclar and Interventional Neurology, 2014, 22-24.

Papadopoulos, M. et al., "Aquaporin-4 Facilitates Reabsorption of Excess Fluid in Vasogenic Brain Edema," The FASEB Journal, published online Jun. 18, 2004, doi: 10.1096/fj.04-1723jfe, 18 pages.

Papadopoulos, M. et al., "Aquaporin-4 Facilitates Reabsorption of Excess Fluid in Vasogenic Brain Edema," The FASEB Journal, 2004, 18, 1291-1293.

Papadopoulos, M. et al., "Aquaporin-4 Gene Disruption in Mice Reduces Brain Swelling and Mortality in Pneumococcal meningitis," The Journal of Biological Chemistry, 2005, 280 (14), 13906-13912.

Papadopoulos, M. et al., "Potential Utility of Aquaporin Modulators for Therapy of Brain Disorders," NIH Public Access, Author Manuscript, available in PMC 2013, 17 pages, face of article states: Published in final edited form as: Prog Brain Res. 2008; 170: 589-601. doi: 10.1016/S0079-6123(08)00446-9.

Papadopoulos, M. et al., "Aquaporin Water Channels in the Nervous System," NIH Public Access, Author Manuscript, available in PMC 2014, 28 pages, face of article states: Published in final edited form as Nat Rev Neurosci. Apr. 2013; 14(4): 265-277. doi: 10.1038/nrn3468.

Pippione, A. et al., "4-Hydroxy-N-[3,5-bis(trifluoromethyl)phenyl]-1,2,5-thiadiazole-3- carboxamide: A Novel Inhibitor of the Canonical NF-kB Cascade," Medicinal Chemistry Communications, 2017, 8, 1850-1855.

Prescott, J. et al., "Targeting IKKβ in Cancer: Challenges and Opportunities for the Therapeutic Utilisation of IKKβ Inhibitors," Cells, 2018, 7, 115, 34 pages, doi: 10.3390/cells7090115.

Quick, A. et al., "Pregnancy-Induced Up-Regulation of Aquaporin-4 Protein in Brain and Its Role in Eclampsia," The FASEB Journal, 2005, 19, 170-175.

Rabinstein, A., "Treatment of Cerebral Edema," Neurologist, 2006, 12 (2), 59-73.

Rabolli, V. et al., "Critical Role of Aquaporins in Interleukin 1β (IL-1β)-induced Inflammation," The Journal of Biological Chemistry, 2014, 289 (20), 13937-13947.

Ramiro, L. et al., "Circulating Aquaporin-4 as a Biomarker of Early Neurological Improvement in Stroke Patients: A Pilot Study," Neuroscience Letters, 2020, 714, 134580, 7 pages, https://doi.org/10.1016/j.neulet.2019.134580.

Rao, K. et al., "Marked Potentiation of Cell Swelling by Cytokines in Ammonia-Sensitized Cultured Astrocytes," Journal of Neuroinflammation, 2010, 7 (66), 8 pages.

Rao, K. et al., "Aquaporin-4 Expression in Cultured Astrocytes after Fluid Percussion Injury," Journal of Neurotrauma, 2011, 28, 371-381.

Raslan, A. et al., "Medical Management of Cerebral Edema," Neurosurgical Focus, 2007, 22 (5), E12, 12 pages.

Raslan, A. et al., "Medical Management of Cerebral Edema," retrieved on Jan. 2, 2015, from http://www.medscape.com/viewarticle559004_6, 17 pages, face of article states: Neurosurgery Focus, 2007, 22 (5), E12.

Restrepo, D. et al., "Essential Activation of $Na^+$—$H^+$ Exchange by $[H^+]$; in HL-60 Cells," American Journal of Physiology, 1990, 259, C490-C502.

Restrepo, L. et al., "Osmotherapy: A Call to Arms," and Response, Stroke, 2001, 32, 811-812.

Rutkovskiy, A. et al., "Aquaporin-4 in the Heart: Expression, Regulation and Functional Role in Ischemia," Basic Research in Cardiology, 2012, doi: 10.1007/s00395-012-0280-6, 13 pages.

Saadoun, S. et al., "Involvement of Aquaporin-4 in Astroglial Cell Migration and Glial Scar Formation," Journal of Cell Science, 2005, 118, 5691-5698.

Saadoun, S. et al., "Greatly Improved Neurological Outcome After Spinal Cord Compression Injury in AQP4-Deficient Mice," Brain, 2008, 131, 1087-1098.

Saadoun, S. et al., "AQP4 Gene Deletion in Mice Does Not Alter Blood-Brain Barrier Integrity or Brain Morphology," Neuroscience, 2009, 161, 764-772.

Saadoun, S. et al., "Aquaporin-4 in Brain and Spinal Cord Oedema," Neuroscience, 2010, 168, 1036-1046.

Sandercock, P. et al., "Corticosteroids for Acute Ischaemic Stroke (Review)," Cochrane Database of Systematic Reviews, 2011, Issue 9, Art. No. CD000064, doi: 10.1002/14651858.CD000064.pub2, 20 pages.

Sandha, J. et al., "Steroids Limit Myocardial Edema During Ex Vivo Perfusion of Hearts Donated After Circulatory Death," Annals of Thoracic Surgery, 2018, 105, 1763-1770.

Sandhu, H. et al., "Upregulation of Contractile Endothelin Type B Receptors by Lipid-soluble Cigarette Smoking Particles in Rat Cerebral Arteries via Activation of MAPK," Toxicology and Applied Pharmacology, 2010, 249, 25-32.

Schwartz, M. et al., "The University of Toronto Head Injury Treatment Study: A Prospective, Randomized Comparison of Pentobarbital and Mannitol," The Canadian Journal of Neurological Sciences, 1984, 11, 434-440.

Second Office Action issued in Chinese Patent Application No. 201380033198.7 dated Dec. 13, 2016, and English-language translation, 13 pages (8 pages Second Office Action, 5 pages translation).

Sepramaniam, S. et al. "MicroRNA 320a Functions as a Novel Endogenous Modulator of Aquaporins 1 and 4 as Well as a Potential

(56) References Cited

OTHER PUBLICATIONS

Therapeutic Target in Cerebral Ischemia," The Journal of Biological Chemistry, 2010, 285 (38), 29223-29230.
Shi, Z. et al., "Aquaporin 4-Mediated Glutamate-Induced Astrocyte Swelling is Partially Mediated through Metabotropic Glutatmate Receptor 5 Activation," Frontiers in Cellular Neuroscience, 2017, 11:116, 12 pages, doi: 10.3389/fncel.2017.0016.
Silberstein, C. et al., "Membrane Organization and Function of M1 and M23 Isoforms of Aquaporin-4 in Epithelial Cells," American Journal of Physiology, Renal Physiology, 2004, 287, F501-F511.
Slater, J. et al., "Discriminating Between Preservation and Reperfusion Injury in Human Cardiac Allografts Using Heart Weight and Left Ventricular Mass," retrieved on Jul. 23, 2015, from https://circ.ahajournals.org/content/92/9/223.full, 8 pages, face of article states: Circulation, 1995, 92, 223-227.
Slivka, A. et al., "High Dose Methylprednisolone Treatment in Experimental Focal Cerebral Ischemia," Experimental Neurology, 2001, 167, 166-172.
Söderlund, C. et al., "Immunosuppressive Therapies after Heart Transplantation—The Balance between Under and Over-immunosuppression," Transplantation Reviews, 2015, 29, 181-189.
Sodium Phosphate, Cold Spring Harbor Protocols, doi: 10.1101/pdb.rec8303, face of document states: copyright 2006, 1 page, retrieved Aug. 31, 2017 from: http://cshprotocols.cshlp.org/content/2006/1/pdb.rec8303.full?text_only=true.
Solenov, E. et al., "Sevenfold-Reduced Osmotic Water Permeability in Primary Astrocyte Cultures from AQP-4-Deficient Mice, Measured by a Fluorescence Quenching Method," American Journal of Physiology, Cell Physiology, 2004, 286, C426-C432.
Stehlik, J. et al., "The Registry of the International Society for Heart and Lung Transplantation: 29th Official Adult Heart Transplant Report—2012," The Journal of Heart and Lung Transplantation, 2012, 31 (10), 1052-1064.
Steiner, T. et al., "Treatment Options for Large Hemispheric Stroke," Neurology, 2001, 57 (Supplement 2), S61-68.
Stella, V. et al., Eds., Biotechnology: Pharmaceutical Aspects; Prodrugs: Challenges and Rewards, Part 2, Springer, New York, New York, 2007, p. 161.
Stokum, J. et al., "Mechanisms of Astrocyte-Mediated Cerebral Edema," NIH Public Access, Author Manuscript, available in PMC 2016, 22 pages, face of article states: Published in final edited form as: Neurochem Res. Feb. 2015; 40 (2):317-328. doi:10.1007/s11064-014-1374- 3.
Stokum, J. et al., "Molecular Pathophysiology of Cerebral Edema," Journal of Cerebral Blood Flow & Metabolism, 2016, 36 (3), 513-538.
Stokum, J. et al., "SUR1-TRPM4 and AQP4 Form a Heteromultimeric Complex that Amplifies Ion/Water Osmotic Coupling and Drives Astrocyte Swelling," HHS Public Access, Author Manuscript, available in PMC 2019, 36 pages, face of article states: Published in final edited form as: *Glia*. Jan. 2018; 66(1): 108-125. doi:10.1002/glia.23231.
Stroop, R. et al., "Magnetic Resonance Imaging Studies with Cluster Algorithm for Characterization of Brain Edema after Controlled Cortical Impact Injury (CCII)," Acta Neurochirurgica, 1998 [Supplement], 71, 303-305.
Su, C. et al., "Endogenous Memory CD8 T Cells Directly Mediate Cardiac Allograft Rejection," American Journal of Transplantation, 2014, 14, 568-579.
Sui, H. et al., "Structural Basis of Water-Specific Transport Through the AQP1 Water Channel," Nature, 2001, 414 (20/27), 872-878.
Sun, M. et al., "Regulation of Aquaporin-4 in a Traumatic Brain Injury Model in Rats," Journal of Neurosurgery, 2003, 98, 565-569.
Suzuki, J. et al., "Novel IKB Kinase Inhibitors for Treatment of Nuclear Factor-κB-related Diseases," Expert Opinion on Investigational Drugs, 2011, 20 (3), 395-405.
Szabó, G. et al., "Systolic and Diastolic Properties and Myocardial Blood Flow in the Heterotopically Transplanted Rat Heart during Acute Cardiac Rejection," World Journal of Surgery, 2001, 25, 545-552.

Tait, M. et al. "Increased Brain Edema in AQP4 Null Mice in an Experimental Model of Subarachnoid Hemorrhage," Neuroscience, 2010, 167, 60-67.
Tajkhorshid, E. et al., "Control of the Selectivity of the Aquaporin Water Channel Family by Global Orientational Tuning," Science, 2002, 296, 525-530.
Tanaka, A. et al., "A Novel NF-κB Inhibitor, IMD-0354, Suppresses Neoplastic Proliferation of Human Mast Cells with Constitutively Activated c-kit Receptors," Blood, 2005, 105 (6), 2324-2331.
Tanaka, A. et al., "A New IκB Kinase β Inhibitor Prevents Human Breast Cancer Progression through Negative Regulation of Cell Cycle Transition," Cancer Research, 2006, 66 (1), 419-426.
Tanaka, A. et al., "Topical Application with a New NF-κB Inhibitor Improves Atopic Dermatitis in NC/NgaTnd Mice," Journal of Investigative Dermatology, 2007, 127, 855-863.
Tang, Z. et al., "Structure-Activity Relationship of Niclosamide Derivatives," Anticancer Research, 2017, 37, 2839-2843.
Taniguchi, M. et al., "Induction of Aquaporin-4 Water Channel mRNA After Focal Cerebral Ischemia in Rat," Molecular Brain Research, 2000, 78, 131-137.
Tanimura, Y. et al., "Acetazolamide Reversibly Inhibits Water Conduction by Aquaporin-4," Journal of Structural Biology, 2009, 166, 16-21.
Tenbroek, E. et al., "Randomized Controlled Studies on the Efficacy of Antiarthritic Agents in Inhibiting Cartilage Degeneration and Pain Associated with Progression of Osteoarthritis in the Rat," Arthritis Research & Therapy, 2016, 18:24, 29 pages, doi: 10.1186/s13075-016-0921-5.
Thiemermann, C., Editorial, "Inhibition of the Activation of Nuclear Factor Kappa B to Reduce Myocardial Reperfusion Injury and Infarct Size," Cardiovascular Research, 63, 2004, 8-10.
Thomalla, G. et al., "Prediction of Malignant Middle Cerebral Artery Infarction by Magnetic Resonance Imaging Within 6 Hours of Symptom Onset: A Prospective Multicenter Observational Study," Annals of Neurology, 2010, 68 (4), 435-445.
Townsend, R. et al., "A Highly Selective Inhibitor of IκB Kinase, BMS-345541, Augments Graft Survival Mediated by Suboptimal Immunosupression in a Murine Model of Cardiac Graft Rejection," Transplantation, 2004, 77 (7), 1090-1094.
Unterberg, A. et al., "Characterisation of Brain Edema Following 'Controlled Cortical Impact Injury' in Rats," Acta Neurochirurgica, 1997 [Supplement], 70, 106-108.
Unterberg, A. et al., "Edema and Brain Trauma," Neuroscience, 2004, 129, 1021-1029.
Van Hoek, A. et al., "Freeze-Fracture Analysis of Plasma Membranes of CHO Cells Stably Expressing Aquaporins 1-5," The Journal of Membrane Biology, 1998, 165, 243-254.
Verkman, A. et al., "Three Distinct Roles of Aquaporin-4 in Brain Function Revealed by Knockout Mice," Biochmica et Biophysica Acta, 2006, doi:10.1016/j.bbamem.2006.02.018, 9 pages.
Verkman, A., "Aquaporins at a Glance," Journal of Cell Science, 2011, 124, 2107-2112.
Verkman, A. et al., "Aquaporin-4: Orthogonal Array Assembly, CNS Functions, and Role in Neuromyelitis Optica," Acta Pharmacologica Sinica, NIH Public Access, Author Manuscript, available in PMC Mar. 19, 2013, 16 pages, article states: published in final edited form as: *Acta Pharmacol Sinica*, Jun. 2011, 32 (6), 702-710. doi:10.1038/aps.2011.27.
Verkman, A., "Aquaporins in Clinical Medicine," NIH Public Access, Author Manuscript, available in PMC 2013, 16 pages, face of article states: Published in final edited form as *Annu Rev Med*. 2012 63: 303-316. doi: 10.1146/annurev-med-043010-193843.
Verkman, A., "Aquaporins," NIH Public Access, Author Manuscript, available in PMC 2014, 6 pages, face article states: Published in final edited form as: *Curr Biol*. Jan. 21, 2013; 23(2): R52-R55, doi: 10.1016/j.cub.2012.11.025.
Verkman, A. et al., "Aquaporins: Important But Elusive Drug Targets," Nature Reviews Drug Discovery, published online 2014, 19 pages, doi: 10.1038/nrd4426.
Verkman, A. et al., "The Aquaporin-4 Water Channel as a Potential Drug Target in Neurological Disorders," HHS Public Access, Author Manuscript, available in PMC 2019, 21 pages, face of article states:

(56) References Cited

OTHER PUBLICATIONS

Published in final edited form as: *Expert Opin Ther Targets*. Dec. 2017; 21(12): 1161-1170. doi:10.1080/14728222.2017.1398236.
Vizuete, M. et al., "Differential Upregulation of Aquaporin-4 mRNA Expression in Reactive Astrocytes After Brain Injury: Potential Role in Brain Edema," Neurobiology of Disease, 1999, 6, 245-258.
Wakatsuki, S. et al., "A Novel IKK Inhibitor Suppresses Heart Failure and Chronic Remodeling After Myocardial Ischemia Via MMP Alteration," Expert Opinion on Therapeutic Targets, 2008, 12 (12), 1469-1476.
Wallisch, J. et al., "Effect of the Novel Aquaporin-4 Antagonist AER-271 in Combined TBI Plus Hemorrhagic Shock in Mice," Critical Care Medicine, 2015, 43 (12, Supplement), Abstract 23.
Wallisch, J. et al., "Aquaporin-4 Inhibitor AER-271 Blocks Early Cerebral Edema in Pediatric Rat Asphyxial Cardiac Arrest," Critical Care Medicine, 2016, 44 (12, Supplement), Abstract 718.
Wallisch, J. et al., "Evaluation of AER-271 in the Controlled Cortical Impact Model of Traumatic Brain Injury: An OBTT Consortium Study," Journal of Neurotrauma, 2016, 33, A-61, Abstract PSA-137.
Wallisch, J. et al., "Aquaporin-4 Inhibitor AER-271 Blocks Edema and Improves Outcome in Pediatric Rat Cardiac Arrest," Critical Care Medicine, 2017, 46 (1, Supplement), Abstract 49.
Wallisch, J. et al., "The Aquaporin-4 Inhibitor AER-271 Blocks Acute Cerebral Edema and Improves Early Outcome in a Pediatric Model of Asphyxial Cardiac Arrest," Pediatric Research, 2018, https://doi.org/10.1038/s41390-018-0215-5, 7 pages.
Waljee, A. et al., "Short Term Use of Oral Corticosteroids and Related Harms Among Adults in the United States: Population Based Cohort Study," BMJ, 2017, 357:j1415, 8 pages, doi: 10.1136/bmj.j1415.
Wang, C. et al., "Mechanism of Aquaporin 4 (AQP 4) Up-regulation in Rat Cerebral Edema Under Hypobaric Hypoxia and the Preventative Effect of Puerarin," Life Sciences, 2018, 193, 270-281.
Wang, F. et al., "Aquaporins as Potential Drug Targets," Acta Pharmacologica Sinica, 2006, 27 (4), 395-401.
Wang, J-W. et al., "Activation of Metabotropic Glutamate Receptor 5 Reduces the Secondary Brain Injury After Traumatic Brain Injury in Rats," Biochemical and Biophysical Research Communications, 2013, 430, 1016-1021.
Wang, X. et al., "Pre-Ischemic Treadmill Training Alleviates Brain Damage Via GLT-1-Mediated Signal Pathway After Ischemic Stroke in Rats," Neuroscience, 2014, 274, 393-402.
Wang, Z-R. et al., "Regulating Effect of Activated NF-κB on Edema Induced by Traumatic Brain Injury of Rats," Asian Pacific Journal of Tropical Medicine, 2016, 9 (3), 274-277.
Whitlock, R. et al., "Methylprednisolone in Patients Undergoing Cardiopulmonary Bypass (SIRS): A Randomised, Double-blind, Placebo-Controlled Trial," Lancet, 2015, 386, 1243-1253.
Wick, W. et al., "Brain Edema in Neurooncology: Radiological Assessment and Management," Onkologie, 2004, 27, 261-266.
Wilson, M. et al., "The Cerebral Effects of Ascent to High Altitudes," Lancet Neurology, 2009, 8, 175-191.
Wong, L. et al., "Vasopressin V2 Receptor Antagonists," Cardiovascular Research, 2001, 51, 391-402.
Written Opinion of the International Searching Authority for International Application No. PCT/US2014/064432, dated Apr. 13, 2015, 7 pages.
Written Opinion of the International Searching Authority for International Application No. PCT/US2014/064441, dated Feb. 13, 2015, 8 pages.
Written Opinion of the International Searching Authority for International Application No. PCT/US2014/064447, dated Apr. 6, 2015, 6 pages.
Written Opinion of the International Searching Authority for International Application No. PCT/US2015/060731, dated Jan. 29, 2016, 8 pages.
Written Opinion of the International Searching Authority for International Application No. PCT/US2017/032563, dated Aug. 24, 2017, 5 pages.

Yang, B. et al., "The Mercurial Insensitive Water Channel (AQP-4) Forms Orthogonal Arrays in Stably Transfected Chinese Hamster Ovary Cells," The Journal of Biological Chemistry, 1996, 271 (9), 4577-4580.
Yang, B. et al., "Lack of Aquaporin-4 Water Transport Inhibition by Antiepileptics and Arylsulfonamides," Bioorganic & Medicinal Chemistry, 2008, 16, 7489-7493.
Yang, M. et al., "Temporal Changes in Expression of Aquaporin3, -4, -5, and -8 in Rat Brains After Permanent Focal Cerebral Ischemia," Brain Research, 2009, 1290, 121-132.
Yang, N. et al., "Effect of (S)-4C3HPG on Brain Damage in the Acute Stage of Moderate Traumatic Brain Injury Model of Mice and Underlying Mechanism," Acta Physiologica Sinica, 2010, 62 (6), 555-559.
Yao, X. et al., "Mildly Reduced Brain Swelling and Improved Neurological Outcome in Aquaporin-4 Knockout Mice following Controlled Cortical Impact Brain Injury," Journal of Neurotrauma, 2015, 32, 1458-1464.
Young, E., Chapter 9 entitled "IKKβ as a Therapeutic Intervention Point for Diseases Related to Inflammation," pp. 255-296, in Anti-Inflammatory Drug Discovery, Levin, J et al., Eds., Royal Society of Chemistry, 2012.
Zador, Z. et al., "Aquaporins: Role in Cerebral Edema and Brain Water Balance," Progress in Brain Research, 2007, 161, Chapter 12, 185-194.
Zeidel, M. et al., "Ultrastructure, Pharmacologic Inhibition, and Transport Selectivity of Aquaporin Channel-Forming Integral Protein in Proteoliposomes," Biochemistry, 1994, 33, 1606-1615.
Zelenina, M. et al., "Water Permeability of Aquaporin-4 is Decreased by Protein Kinase C and Dopamine," American Journal of Physiology, Renal Physiology, 2002, 283, F309-F318.
Zeng, X-N. et al., "AQP4 Knockout Aggravates Ischemia/Reperfusion Injury in Mice," CNS Neuroscience & Therapeutics, 2012, 18, 388-394.
Zhang, D. et al., "Aquaporin Deletion in Mice Reduces Intraocular Pressure and Aqueous Fluid Production," The Journal of General Physiology, 2002, 119, 561-569.
Zhang, F. et al., "The Effect of Treadmill Training Pre-Exercise on Glutamate Receptor Expression in Rats After Cerebral Ischemia," International Journal of Molecular Sciences, 2010, 11, 2658-2669.
Zhang, Z-Y. et al., "Activation of mGluR5 Attenuates Microglial Activation and Neuronal Apoptosis in Early Brain Injury After Experimental Subarachnoid Hemorrhage in Rats," Neurochemical Research, 2015, 40, 1121-1132.
Zhao, F. et al., "Aquaporin-4 Deletion Ameliorates Hypoglycemia-induced BBB Permeability by Inhibiting Inflammatory Responses," Journal of Neuroinflammation, 2018, 15:157, 13 pages, https://doi.org/10.1186/s12974-018-1203-8.
Requirement for Restriction/Election dated Aug. 13, 2015, issued in U.S. Appl. No. 14/398,947, 10 pages.
Non-Final Office Action dated Dec. 18, 2015, issued in U.S. Appl. No. 14/398,947, 31 pages.
Final Office Action dated Sep. 20, 2016, issued in U.S. Appl. No. 14/398,947, 41 pages.
Advisory Action dated Dec. 16, 2016, issued in U.S. Appl. No. 14/398,947, 3 pages.
Non-Final Office Action dated Aug. 16, 2017, issued in U.S. Appl. No. 14/398,947, 24 pages.
Notice of Allowance dated Feb. 2, 2018, in U.S. Appl. No. 14/398,947, 10 pages.
Notice of Allowability and Examiner-Initiated Interview Summary dated Feb. 15, 2018, in U.S. Appl. No. 14/398,947, 7 pages.
Requirement for Restriction/Election dated Sep. 22, 2015, issued in U.S. Appl. No. 14/752,839, 6 pages.
Non-Final Office Action dated Mar. 8, 2016, issued in U.S. Appl. No. 14/752,839, 23 pages.
Final Office Action dated Aug. 30, 2016, issued in U.S. Appl. No. 14/752,839, 17 pages.

(56) References Cited

OTHER PUBLICATIONS

Notice of Allowance dated Oct. 7, 2016, in U.S. Appl. No. 14/752,839, 10 pages.
Notice of Allowance dated Jul. 19, 2017, issued in U.S. Appl. No. 15/034,274, 9 pages.

* cited by examiner

METHODS OF TREATING OR CONTROLLING CYTOTOXIC CEREBRAL EDEMA CONSEQUENT TO AN ISCHEMIC STROKE

CROSS REFERENCE TO RELATED APPLICATIONS

This application is a continuation of U.S. patent application Ser. No. 15/982,644, filed May 17, 2018, which is a continuation of U.S. patent application Ser. No. 14/398,947, filed Nov. 4, 2014, now issued as U.S. Pat. No. 9,994,514, which is the National Stage Entry under 35 U.S.C. § 371 of International Application No. PCT/US2013/040194 filed May 8, 2013, which claims priority to U.S. Provisional Application No. 61/644,268 filed May 8, 2012, U.S. Provisional Application No. 61/651,778 filed May 25, 2012, and U.S. Provisional Application No. 61/799,606 filed Mar. 15, 2013, the contents of each of which are incorporated herein by reference.

STATEMENT REGARDING FEDERALLY SPONSORED RESEARCH OR DEVELOPMENT

This invention was made with government support under Grant Numbers R43 NS060199 and R44 NS060199 awarded by the National Institutes of Health. The government has certain rights in the invention.

FIELD OF THE INVENTION

The present invention relates to the use of selective aquaporin inhibitors, e.g., of aquaporin-4 or aquaporin-2, e.g., certain phenylbenzamide compounds, for the prophylaxis, treatment and control of aquaporin-mediated conditions, e.g., diseases of water imbalance, for example edema (particularly edema of the brain and spinal cord, e.g., following trauma or ischemic stroke, as well as the edema associated with glioma, meningitis, acute mountain sickness, epileptic seizures, infections, metabolic disorders, hypoxia, water intoxication, hepatic failure, hepatic encephalopathy, diabetic ketoacidosis, abscess, eclampsia, Creutzfeldt-Jakob disease, and lupus cerebritis, as well as edema consequent to microgravity and/or radiation exposure, as well as edema consequent to invasive central nervous system procedures, e.g., neurosurgery, endovascular clot removal, spinal tap, aneurysm repair, or deep brain stimulation, as well as retinal edema), as well as hyponatremia and excess fluid retention, and diseases such as epilepsy, retinal ischemia and other diseases of the eye associated with abnormalities in intraocular pressure and/or tissue hydration, myocardial ischemia, myocardial ischemia/reperfusion injury, myocardial infarction, myocardial hypoxia, congestive heart failure, sepsis, and neuromyelitis optica, as well as migraines, as well as to novel assays for identifying aquaporin inhibitors.

BACKGROUND OF THE INVENTION

Aquaporins are cell membrane proteins that act as molecular water channels to mediate the flow of water in and out of the cells. While there is some degree of passive diffusion or osmosis of water across cell membranes, the rapid and selective transport of water in and out of cells involves aquaporins. These water channels selectively conduct water molecules in and out of the cell, while blocking the passage of ions and other solutes, thereby preserving the membrane potential of the cell. Aquaporins are found in virtually all life forms, from bacteria to plants to animals. In humans, they are found in cells throughout the body.

Cerebral edema (CE) is a major contributor to stroke damage, as it can result in increased intracerebral pressure (ICP), a corresponding decrease in cerebral perfusion, and potentially permanent or fatal brain damage. Edema also contributes to CNS damage in, for example, traumatic brain and spinal cord injury, glioma, meningitis, acute mountain sickness, epileptic seizures, infections, metabolic disorders, hypoxia, water intoxication, hepatic failure, hepatic encephalopathy, diabetic ketoacidosis, abscess, eclampsia, Creutzfeldt-Jakob disease, and lupus cerebritis. Patients surviving the period of maximal ICP, usually the three days following a stroke or traumatic brain injury, are likely to survive. Unfortunately, only a few treatment options are available for CE, and these are of limited efficacy.

Hyponatremia, characterized by serum sodium levels ≤135 mM, is the most common form of electrolyte imbalance with hospitals nationwide reporting an incidence of 15-20%. The associated fluid retention is symptomatic of heart failure (HF), liver cirrhosis, nephrotic disorder, and syndrome of inappropriate antidiuretic hormone secretion (SIADH). Various diuretics are used to treat congestion associated with HF. By inhibiting the Na/K/Cl cotransporter in the thick ascending loop of Henle, loop diuretics cause natriuresis by decreasing $Na^+$ and $Cl^-$ reabsorption from the urine. An alternative therapy for hyponatremia is the use of vasopressin receptor antagonists, which inhibit water reabsorption by inhibiting the vasopressin-induced trafficking of AQP2. Unfortunately, both loop diuretics and vasopressin receptor antagonists act indirectly toward a desired physiological outcome. An ideal drug would block water reabsorption directly, thus minimizing potential side-effects caused by upstream effectors, but no such drugs are currently known.

Epilepsy is a brain disorder characterized by recurrent seizures. Seizures occur because of disturbed brain activity resulting in some degree of temporary brain dysfunction. Seizures may cause uncontrollable shaking and loss of consciousness but, more commonly, a person experiencing a seizure stops moving or becomes unaware of what is happening. Anticonvulsants may be used to treat epilepsy, however anticonvulsants are not effective for all people with epilepsy.

Ischemia is a condition characterized by an interruption or inadequate supply of blood to tissues. Retinal ischemia occurs due to a deficient supply of blood to the retina. Vascular occlusion, glaucoma, and diabetic retinopathy are associated with retinal ischemia and can produce retinal edema and ganglion cell death leading to visual impairment and blindness. AQP4 is expressed in the Müller cells in the retina. Due to relatively ineffectual treatment, retinal ischemia remains a common cause of visual impairment and blindness.

Myocardial ischemia is a condition caused by a blockage or constriction of one more of the coronary arteries, such as can occur with atherosclerotic plaque occlusion or rupture. Myocardial infarction, a heart attack, occurs when myocardial ischemia exceeds a critical threshold and overwhelms myocardial cellular repair mechanisms designed to maintain normal operating function and homeostasis. Myocardial infarction remains a leading cause of morbidity and mortality worldwide. Compounds effective in treating myocardial ischemia, myocardial ischemia/reperfusion injury, myocardial infarction, and congestive heart failure would be useful pharmaceuticals.

Phenylbenzamide compounds are known as pharmaceuticals. Phenylbenzamides include compounds such as niclosamide (5-chloro-N-(2-chloro-4-nitrophenyl)-2-hydroxybenzamide), an antihemintic agent used to treat tapeworms, but are not known to have any effect on aquaporins. US Patent Publication US 2010/0274051 A1 (the contents of which are incorporated herein by reference) describe certain phenylbenzamides as being useful to inhibit NF-κB via selective inhibition of IKK-β, while U.S. Pat. No. 7,626,042 (also incorporated herein by reference) discloses O-acyl derivatives of such compounds, while U.S. Pat. No. 7,700,655 (also incorporated herein by reference) describe certain phenylbenzamides as being useful to treat allergic diseases. These patent applications, however, do not disclose anything about cerebral edema or water imbalance (aquaresis) or aquaporins.

In a 2004 paper, a group purportedly investigated the efficacy of N-(3,5-Bis-trifluoromethyl-phenyl)-5-chloro-2-hydroxy-benzamide in 1 κB phosphorylation blockade in a rat myocardial ischemia/reperfusion injury model. Onai, Y. et al., "Inhibition of IκB Phosphorylation in Cardiomyocytes Attenuates Myocardial Ischemia/Reperfusion Injury," Cardiovascular Research, 2004, 63, 51-59. The group reported some activity. However, subsequently, the activity effect could not be confirmed and accordingly N-(3,5-Bis-trifluoromethyl-phenyl)-5-chloro-2-hydroxy-benzamide was not pursued for this indication in humans.

Prior to this invention, there are have been no known specific, validated inhibitors of aquaporins, for example AQP4 or AQP2. Certain antiepileptic or sulfonamide drugs (e.g., acetylsulfanilamide, acetazolamide, 6-ethoxy-benzothiazole-2-sulfonamide, topiramate, zonisamide, phenytoin, lamotrigine, and sumatriptan) were at one point reported to be possible inhibitors of AQP4, but this later proved to be incorrect. Yang, et al., Bioorganic & Medicinal Chemistry (2008) 16: 7489-7493. No direct inhibitors of AQP2 have been reported. The search for therapeutically useful aquaporin inhibitors has been hampered by a lack of effective high throughput screening assays, as well as by a lack of highly selective inhibitors to develop and validate the assays and to serve as positive controls or binding competitors.

There is a great need for improved approaches to treating and controlling diseases of water imbalance, such as edema, for example cerebral edema, and water retention and hyponatremia, as well as diseases such as epilepsy, retinal ischemia, myocardial ischemia, myocardial ischemia/reperfusion injury, myocardial infarction, myocardial hypoxia, congestive heart failure, sepsis, and neuromyelitis optica, as well as migraines.

BRIEF SUMMARY OF THE INVENTION

The invention provides the use of selective aquaporin inhibitors, e.g., of aquaporin-4 or aquaporin-2 for the prophylaxis, treatment and control of aquaporin-mediated conditions, e.g., diseases of water imbalance, for example edema (particularly edema of the brain and spinal cord, e.g., following trauma or ischemic stroke, as well as the edema associated with glioma, meningitis, acute mountain sickness, epileptic seizures, infections, metabolic disorders, water intoxication, hepatic failure, hepatic encephalopathy, diabetic ketoacidosis, abscess, eclampsia, Creutzfeldt-Jakob disease, and lupus cerebritis, as well as the edema consequent to microgravity and/or radiation exposure, as well as edema consequent to invasive central nervous system procedures, e.g., neurosurgery, endovascular clot removal, spinal tap, aneurysm repair, or deep brain stimulation, as well as retinal edema, as well as brain swelling consequent to cardiac arrest, e.g., related to the development of the metabolic acidosis (e.g. lactic acidosis) due to hypoxia before the resuscitation period), as well as hyponatremia and excess fluid retention, as well as diseases such as epilepsy, retinal ischemia and other diseases of the eye associated with abnormalities in intraocular pressure or tissue hydration, myocardial ischemia, myocardial ischemia/reperfusion injury, myocardial infarction, myocardial hypoxia, congestive heart failure, sepsis, and neuromyelitis optica, as well as migraines.

The invention further provides the use of certain phenylbenzamides to inhibit aquaporins, particularly AQP4 and AQP2.

The invention provides, inter alia, methods of treating or controlling a disease or condition mediated by an aquaporin, e.g., diseases or conditions of water imbalance and other diseases, for example, edema of the brain or spinal cord, e.g., cerebral edema, e.g. cerebral edema consequent to head trauma, ischemic stroke, glioma, meningitis, acute mountain sickness, epileptic seizures, infections, metabolic disorders, hypoxia (including general systemic hypoxia and hypoxia due to cardiac arrest), water intoxication, hepatic failure, hepatic encephalopathy, diabetic ketoacidosis, abscess, eclampsia, Creutzfeldt-Jakob disease, lupus cerebritis, or invasive central nervous system procedures, e.g., neurosurgery, endovascular clot removal, spinal tap, aneurysm repair, or deep brain stimulation or, e.g., spinal cord edema consequent to spinal cord trauma, e.g., spinal cord compression; or cerebral and/or optical nerve edema consequent to microgravity and/or radiation exposure; or retinal edema; or hyponatremia or excessive fluid retention, e.g., consequent to heart failure (HF), liver cirrhosis, nephrotic disorder, or syndrome of inappropriate antidiuretic hormone secretion (SIADH); or epilepsy, retinal ischemia or other diseases of the eye associated with abnormalities in intraocular pressure and/or tissue hydration, myocardial ischemia, myocardial ischemia/reperfusion injury, myocardial infarction, myocardial hypoxia, congestive heart failure, sepsis, or neuromyelitis optica;

or migraines, comprising administering to a patient in need thereof an effective amount of an aquaporin inhibitor, e.g., an inhibitor of AQP2 or AQP4, for example a phenylbenzamide, e.g., niclosamide or a compound of formula (I) as described in US 2010/0274051 A1 or U.S. Pat. No. 7,700,655, e.g., a compound of general formulae (I), (I-1), (I-2), (I-3), and (I-4) as set forth therein, e.g., selected from Compound Nos. 1-223 as set forth in US 2010/0274051 or Compound Nos. 301-555 as set forth in U.S. Pat. No. 7,700,655, or a compound of formula (I) as described in U.S. Pat. No. 7,626,042, e.g., selected from Compound Nos. 1-151 as set forth therein; for example a compound of formula 1a:

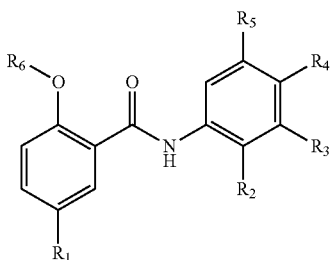

wherein $R_1$, $R_2$, $R_3$, $R_4$, and $R_5$ are selected from H, halo, halogenated $C_{1-4}$ alkyl (e.g., trifluoromethyl), and cyano; and $R_6$ is selected from H and physiologically hydrolysable and acceptable acyl groups, in free or pharmaceutically acceptable salt form.

The invention further provides high throughput assays for identification of specific aquaporins, comprising measuring the response of an aquaporin-expressing cell population versus a control cell population to a hypertonic or hypotonic solution in the presence or absence of a test compound.

The invention further provides a compound of formula

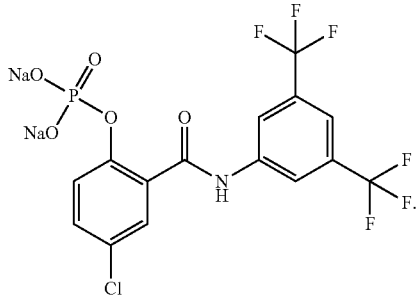

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

$V/V_0 = V_i + dV_{max}(1-e^{(-kt)})$; where $V/V_0$=relative brain volume, $V_i$=initial relative brain volume, $dV_{max}$=maximum change in relative brain volume, k=first order rate constant (min$^{-1}$), and t=time in minutes.

Figure 7:
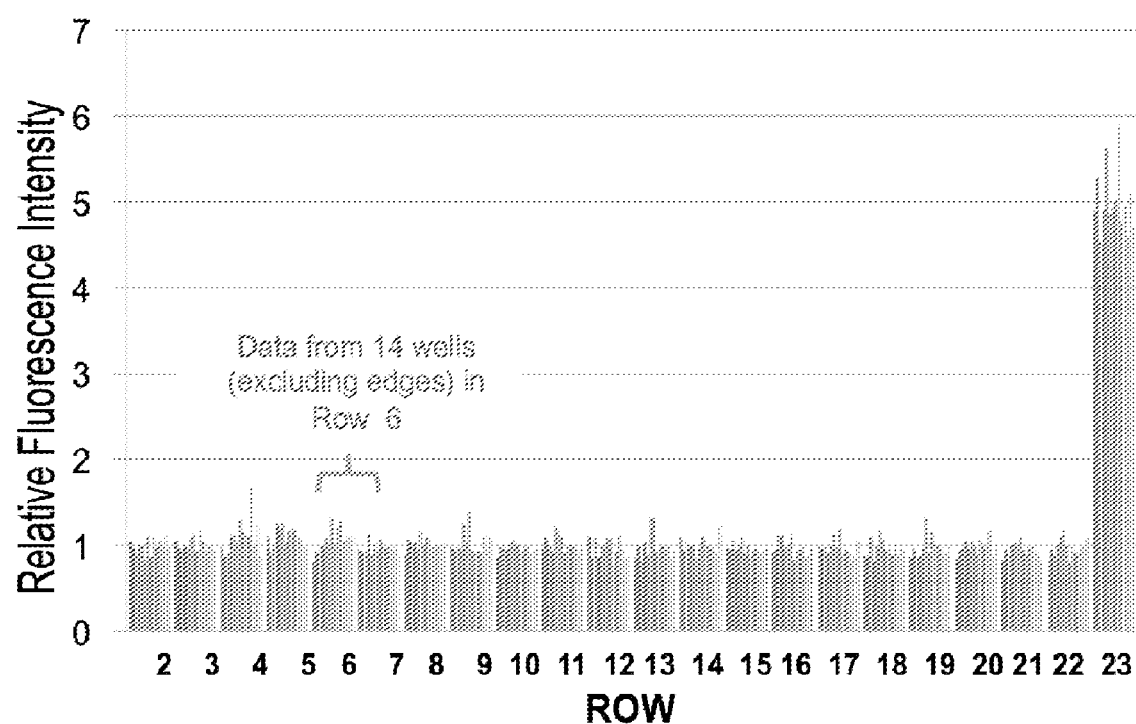

FIG. 7 depicts the calcein fluorescence end-point assay used for high throughput screening.

Figure 8:
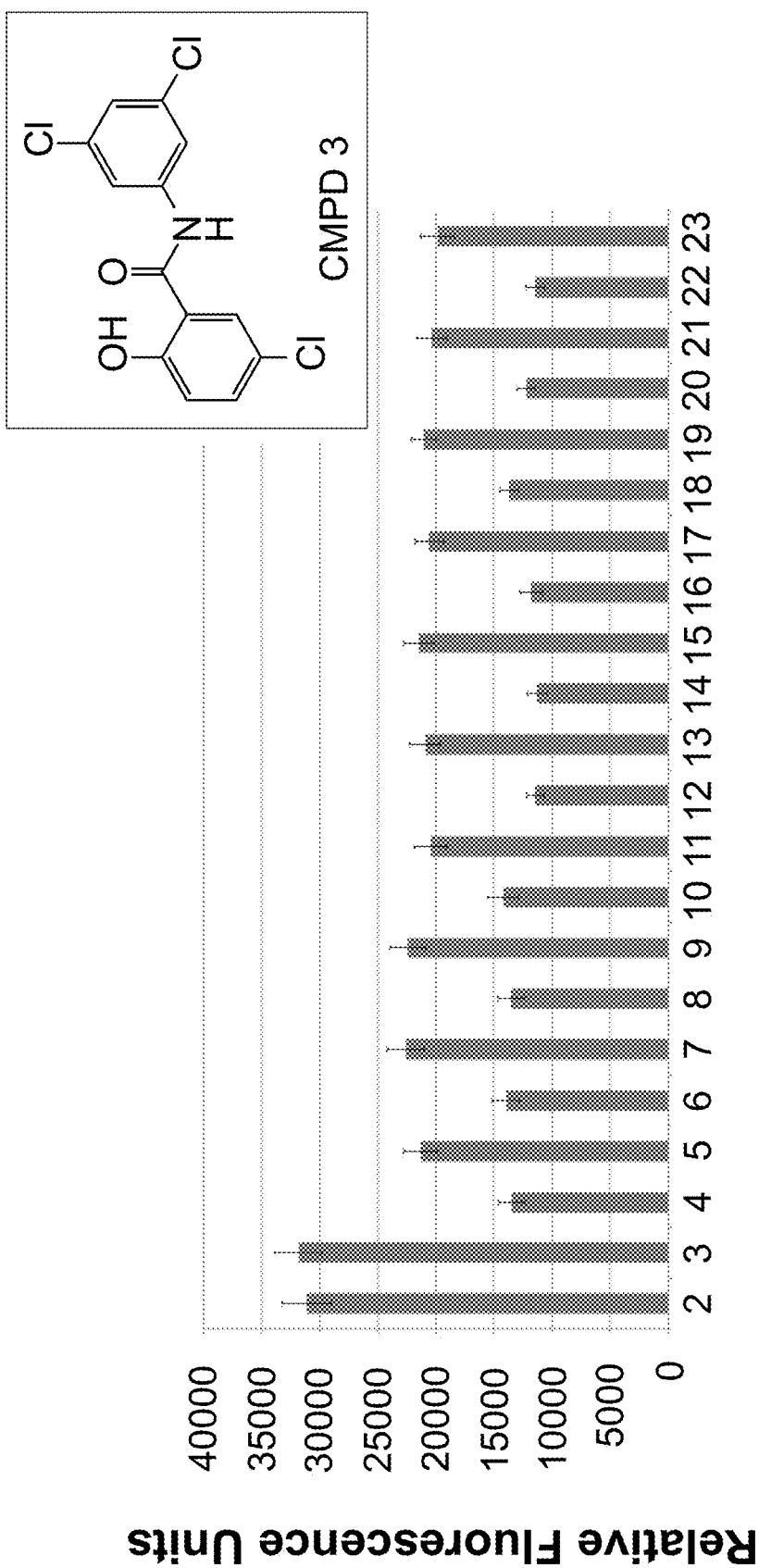

FIG. 8 depicts hit validation using the Cell Bursting Aquaporin Assay; inset shows the structure of Compound 3.

Figure 9:
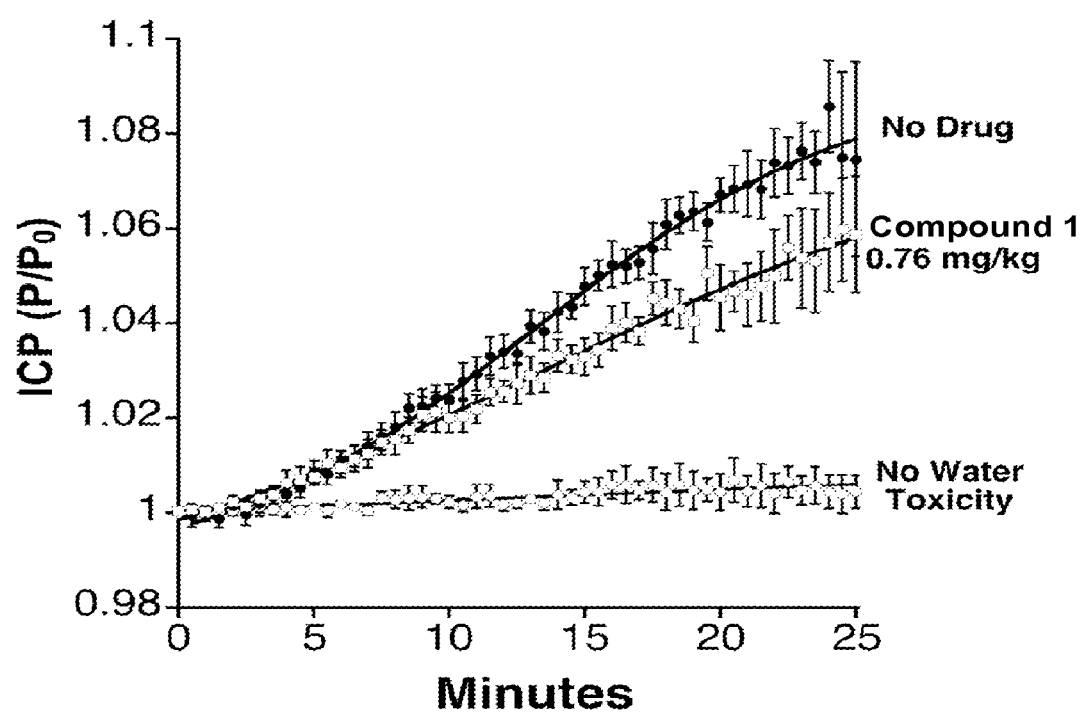

FIG. 9 depicts reduction in intracranial pressure (ICP) in the mouse water toxicity model with Compound 1 at 0.76 mg/kg.

Figure 10:
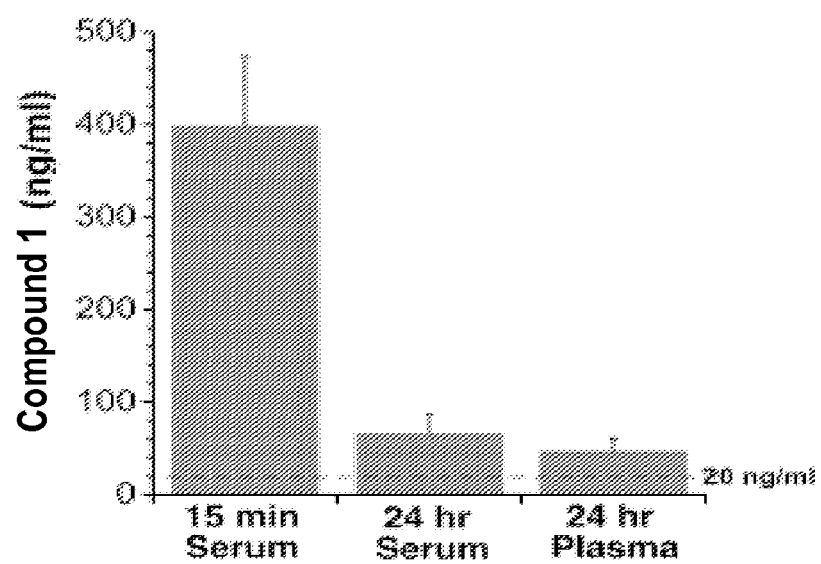

FIG. 10 depicts plasma and serum levels of Compound 1 converted from Compound 5 (compound of formula 1a where $R_1$ is chloro, $R_3$ and $R_5$ are each trifluoromethyl, $R_2$ and $R_4$ are H, and $R_6$ is P(=O)(O)$_2$ in disodium salt form).

Figure 11:
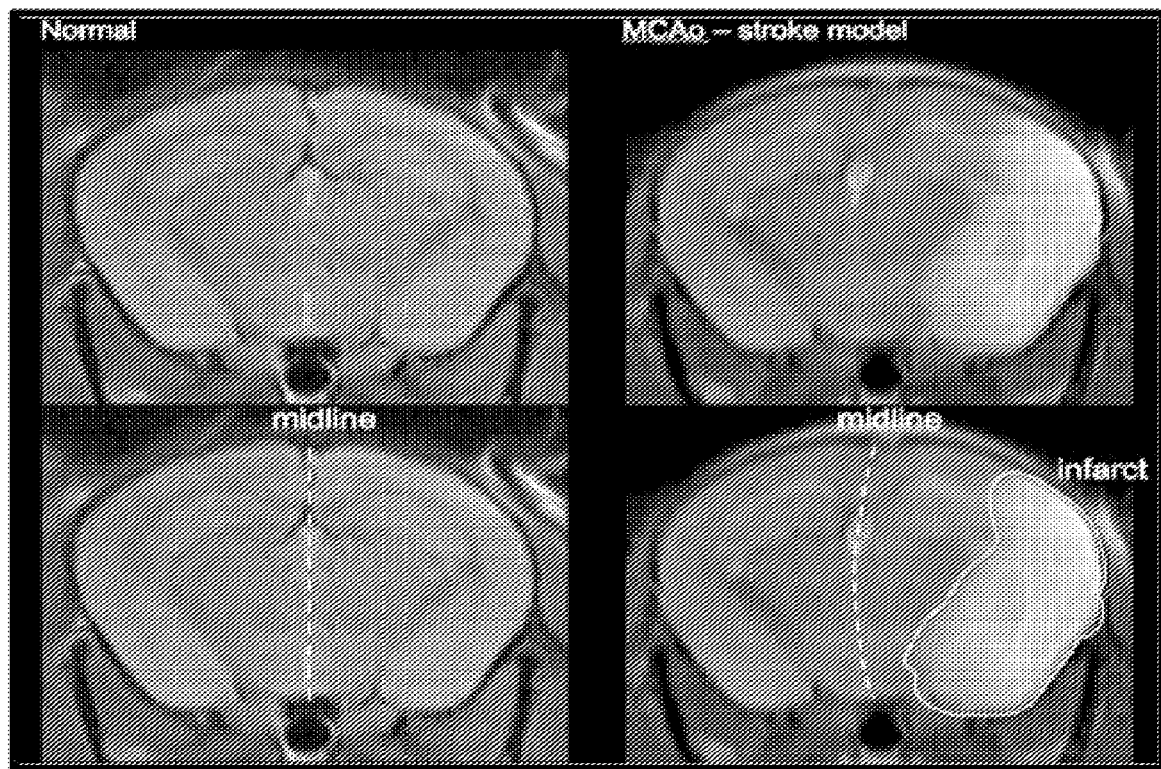

FIG. 11 depicts mouse middle cerebral artery occlusion (MCAo) model of ischemic stroke.

Figure 12:
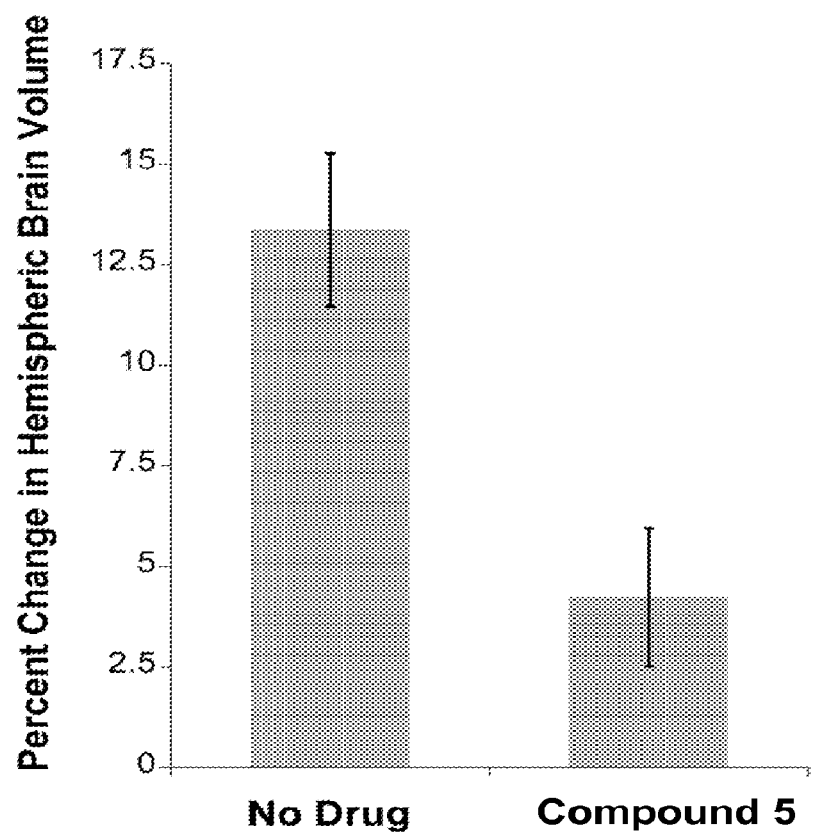

FIG. 12 depicts relative change in hemispheric brain volume in the mouse middle cerebral artery occlusion (MCAo) model.

Figure 13:
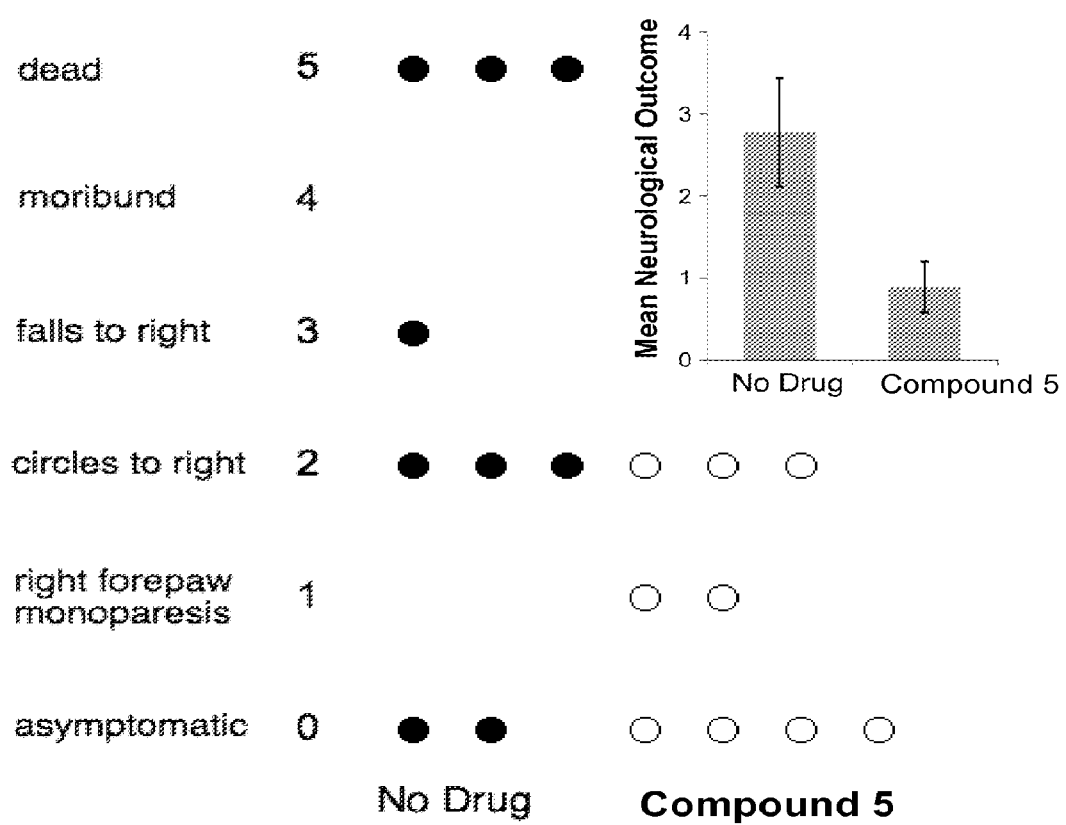

FIG. 13 depicts neurological outcome following MCAo in mice treated with saline (no drug, •) or Compound 5 (o).

DETAILED DESCRIPTION OF THE INVENTION

The following description of the preferred embodiments is merely exemplary in nature and is in no way intended to limit the invention, its application, or uses.

Expression of Aquaporin-4 (AQP4) is upregulated in animal models of trauma, stroke and water intoxication as well as around human malignant brain tumors. Aquaporin-4 (AQP4) has been shown to play a critical role in the development of cerebral and spinal cord edema. AQP4 provides the primary route for water movement across the BBB and glia limitans. AQP4 knockout mice, without the APQ4 gene, have improved survival compared to wild-type mice in models of ischemic stroke, water toxicity, bacterial meningitis, and spinal cord compression.

Cerebral edema (CE) is generally divided into 2 major categories: vasogenic and cytotoxic. Vasogenic cerebral edema may occur when a breach in the blood-brain barrier (BBB) allows water and solutes to diffuse into the brain. It has been reported that AQP4-null mice have increased brain edema in a model of subarachnoid hemorrhage, suggesting that AQP4 may be required for the clearance of water collected in intercellular space. In contrast, cytotoxic cerebral edema may be initiated by ischemia which results in reduced plasma osmolality rather than a disrupted BBB. Ischemia may lead to a drop in ATP levels which is thought to slow the Na—K ATPase pump resulting in an uptake of Na$^+$ and Cl$^-$ through leakage pathways. The net effect may be a cellular osmotic imbalance, drawing H$_2$O into cells—astrocytes more so than neurons—and leading to increased ICP.

Mouse models for ischemic stroke, water toxicity, bacterial meningitis, and spinal-cord compression fall into this category. In these models, AQP4-null mice have reduced CE pointing to AQP4 as the central pathway for water movement into the brain during the formation of cytotoxic CE. However, cytotoxic and vasogenic edema are not sharply divided categories; an injury that initially causes cytotoxic edema may be followed later, e.g., within the next hours to days, by vasogenic edema. This may suggest different treatments for cerebral edema at different times.

It has been reported that propensity to epileptic seizures is related to relative cellular and extracellular space (ECS) volume. Hyperexcitability and increased epileptiform activity results from hypotonic exposure which decreases ECS volume, while attenuated epileptiform activity results from hyperosmolar medium. Furosemide, which blocks seizure-induced cell swelling, has been reported to inhibit epileptiform activity in vitro and in vivo. AQP4 knockout mice were reported to have lower seizure susceptibility to the convulsant pentylenetetrazol and a greater electrographic seizure threshold when seizures were induced by electrical stimulation in the hippocampus. It was also reported that AQP4 knockout mice had more prolonged hippocampal-stimulation evoked seizures compared to wild type mice.

AQP4 is expressed in the Müller cells in the retina. Studies have implicated Müller cells in the pathogenesis of retinal injury after ischemia. It has been reported that AQP4 deletion in mice conferred significant preservation of retinal function and architecture after retinal ischemia.

AQP4 is reportedly found in mammalian hearts. It has been reported that AQP4 expression in the human heart is present at both the mRNA and protein level. Water accumulates in the myocardium as a result of ischemia, when ischemic tissue becomes hyperosmolar and attracts water from the capillary lumen. The water is transported into the myocardial cells, for example, into cardiomyocytes. Reperfusion delivers normoosmolar blood to the hyperosmolar cells, which leads to further cell swelling, which may even involve cells outside the risk area. This water accumulation leads to a pronounced depression of cardiac function, and aggravates effects of shortage in oxygen and nutrient supply. Myocardial ischemia/reperfusion injury refers to damage caused by ischemia followed by reperfusion in the heart. It has been reported that AQP4 knockout mice had reduced infarct size after both ex vivo ischemia-reperfusion and after in vivo ischemia without reperfusion. It was concluded that the AQP4 knockout genotype conferred increased tolerance to ischemic injury.

Neuromyelitis optica (NMO) is a neuroinflammatory demyelinating disease that primarily affects optic nerve and spinal cord. A feature of NMO is the presence of serum antibodies directed against extracellular epitopes on AQP4. It has been reported that most, if not all, NMO patients are seropositive for AQP4 autoantibodies (NMO-IgG). It is thought that NMO-IgG binding to AQP4 in astrocytes initiates an inflammatory cascade and the consequent neuroinflammation and myelin loss produce neurological deficits. Blocking binding of those antibodies to AQP4 could prevent the initiation of the inflammatory cascade.

In one embodiment, the invention provides methods of treating edema mediated by aquaporin, e.g., AQP4, wherein the edema is consequent to hypoxia, e.g., general systemic hypoxia, e.g., hypoxia caused by an interruption of blood perfusion, for example wherein the edema is cerebral edema consequent to hypoxia caused by cardiac arrest, stroke, or other interruption of blood perfusion to the brain, or wherein the edema is cardiac edema consequent to cardiac ischemia or other interruption of blood flow to the heart. Hypoxia can lead to development of metabolic acidosis (e.g. lactic acidosis), which in turn leads to edema, and the edema itself can then reduce blood perfusion, leading to cell death and poorer outcomes, particularly in tissues where swelling is physically constrained, for example within the skull or within the pericardium. This hypoxia is believed to be why, for example, patients who have been rescued from cardiac arrest may subsequently exhibit brain swelling, as well as damage to the cardiac tissue. Blocking aquaporin channels, e.g., AQP4, e.g., by administering an aquaporin-inhibiting compound as described herein, inhibits or controls this edema, thereby limiting further damage to the affected tissue.

Aquaporin-2 (AQP2) is the primary route of water movement at the collecting duct in the kidney. Blocking this water channel would lower water reabsorption without incurring electrolyte imbalances or interfering with vasopressin receptor-mediated signaling. Evidence that an AQP2 blocker would not produce electrolyte imbalances, and instead be an effective treatment for hyponatremia, comes from patients with diabetes insipidus who lack functional AQP2. They exhibit chronic aquaresis but—if normal hydration is maintained—do not demonstrate any other consequence of their long term loss of AQP2 function.

The invention thus provides the use of aquaporin inhibitors in controlling diseases or conditions of water imbalance, including edema, particularly edema of the brain and spinal cord, e.g., following trauma or ischemic stroke, as well as the edema associated with glioma, meningitis, acute mountain sickness, epileptic seizures, infections, metabolic disorders, hypoxia, water intoxication, hepatic failure, hepatic encephalopathy, hypoxia, and diabetic ketoacidosis by inhibiting water uptake through the BBB, and also useful in treating and controlling hyponatremia and excessive fluid retention, by inhibiting water uptake at the kidneys. This invention also provides the use of aquaporin inhibitors in controlling diseases or conditions including epilepsy, retinal ischemia and other diseases of the eye associated with abnormalities in intraocular pressure and/or tissue hydration, myocardial ischemia, myocardial ischemia/reperfusion injury, myocardial infarction, myocardial hypoxia, congestive heart failure, sepsis, neuromyelitis optica, and migraines.

In one embodiment, the invention provides a method (Method 1) of treating or controlling a disease or condition mediated by an aquaporin comprising administering to a patient in need thereof an effective amount of a phenylbenzamide compound, e.g., an effective amount of niclosamide (5-chloro-N-(2-chloro-4-nitrophenyl)-2-hydroxybenzamide) or a compound of Formula 1:

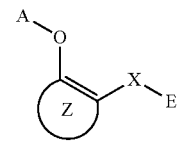

wherein X represents a connecting group whose number of atoms in the main chain is 2 to 5 (said connecting group may be substituted), A represents a hydrogen atom or an acyl group which may be substituted, or a $C_1$ to $C_6$ alkyl group which may be substituted, or A may bind to connecting group X to form a cyclic structure which may be substituted, E represents an aryl group which may be substituted or a heteroaryl group which may be substituted, ring Z represents an arene which may have one or more substituents in addition to the group represented by formula—O-A wherein A has the same meaning as that defined above and the group represented by formula—X-E wherein each of X and E has the same meaning as that defined above, or a heteroarene which may have one or more substituents in addition to the group represented by formula—O-A wherein A has the same meaning as that defined above and the group represented by formula—X-E wherein each of X and E has the same meaning as that defined above; in free or pharmaceutically acceptable salt form, including solvate or hydrate forms; e.g.

1.1. Method 1 wherein the compound of Formula I is selected from the compounds of formula (I) as described in US 2010/0274051 A1 or U.S. Pat. No. 7,700,655, e.g., a compound of general formulas (I), (I-1), (I-2), (I-3), and (I-4) as set forth therein, e.g., selected from Compound Nos. 1-223 as set forth in US 2010/0274051 or Compound Nos. 301-555 as set forth in U.S. Pat. No. 7,700,655.

1.2. Method 1.1 wherein the compound of Formula I is selected from the free or pharmaceutically acceptable salt forms of:
N-[3,5-bis(trifluoromethyl)phenyl]-5-fluoro-2-hydroxybenzamide,
N-[3,5-bis(trifluoromethyl)phenyl]-5-cyano-2-hydroxybenzamide,
N-[3,5-bis(trifluoromethyl)phenyl]-2-hydroxy-5-(trifluoromethyl)benzamide,
N-[3,5-bis(trifluoromethyl)phenyl]-2-hydroxy-5-(1,1,2,2,2-pentafluoroethyl)benzamide,
N-[3,5-bis(trifluoromethyl)phenyl]-5-(2,2-dicyanoethen-1-yl)-2-hydroxybenzamide,
N-[3,5-bis(trifluoromethyl)phenyl]-5-ethynyl-2-hydroxybenzamide,
N-[3,5-bis(trifluoromethyl)phenyl]-2-hydroxy-5-(phenylethynyl)benzamide,
N-[3,5-bis(trifluoromethyl)phenyl]-2-hydroxy-5-[(trimethylsilyl)ethynyl]benzamide,
N-[3,5-bis(trifluoromethyl)phenyl]-4-hydroxybiphenyl-3-carboxamide,
N-[3,5-bis(trifluoromethyl)phenyl]-2-hydroxy-5-(3-thienyl)benzamide,
N-[3,5-bis(trifluoromethyl)phenyl]-2-hydroxy-5-(1-pyrrolyl)benzamide,
N-[3,5-bis(trifluoromethyl)phenyl]-2-hydroxy-5-(2-methylthiazol-4-yl)benzamide,
N-[3,5-bis(trifluoromethyl)phenyl]-2-hydroxy-5-(2-pyridyl)benzamide,
N-[3,5-bis(trifluoromethyl)phenyl]-5-dimethylsulfamoyl-2-hydroxybenzamide,
N-[3,5-bis(trifluoromethyl)phenyl]-2-hydroxy-5-(pyrrole-1-sulfonyl)benzamide,
N-[2,5-bis(trifluoromethyl)phenyl]-5-chloro-2-hydroxybenzamide,
N-(2,5-bis(trifluoromethyl)phenyl-5-bromo-2-hydroxybenzamide,
2-acetoxy-N-[2,5-bis(trifluoromethyl)phenyl]-5-chlorobenzamide,
2-acetoxy-N-[3,5-bis(trifluoromethyl)phenyl]-5-chlorobenzamide,
5-chloro-N-[2-fluoro-3-(trifluoromethyl)phenyl]-2-hydroxybenzamide,
5-chloro-N-[2-fluoro-5-(trifluoromethyl)phenyl]-2-hydroxybenzamide,
5-chloro-N-[2-chloro-5-(trifluoromethyl)phenyl]-2-hydroxybenzamide,
5-bromo-N-[2-chloro-5-(trifluoromethyl)phenyl]-2-hydroxybenzamide,
2-acetoxy-5-chloro-N-[2-chloro-5-(trifluoromethyl)phenyl]benzamide,
5-chloro-N-[3-fluoro-5-(trifluoromethyl)phenyl]-2-hydroxybenzamide,
5-bromo-N-[3-bromo-5-(trifluoromethyl)phenyl]-2-hydroxybenzamide,
5-chloro-N-[3-fluoro-5-(trifluoromethyl)phenyl]-2-hydroxybenzamide,
5-chloro-N-[4-fluoro-3-(trifluoromethyl)phenyl]-2-hydroxybenzamide,
5-bromo-N-[4-chloro-3-(trifluoromethyl)phenyl]-2-hydroxybenzamide,
5-chloro-2-hydroxy-N-[2-nitro-5-(trifluoromethyl)phenyl]benzamide,
5-bromo-N-[4-cyano-3-(trifluoromethyl)phenyl]-2-hydroxybenzamide,
5-chloro-2-hydroxy-N-[2-methyl-3-(trifluoromethyl)phenyl]benzamide,
5-chloro-2-hydroxy-N-[2-methyl-5-(trifluoromethyl)phenyl]benzamide,
2-hydroxy-5-methyl-N-[2-methyl-5-(trifluoromethyl)phenyl]benzamide,
5-chloro-2-hydroxy-N-[4-methyl-3-(trifluoromethyl)phenyl]benzamide,
2-hydroxy-5-methyl-N-[4-methyl-3-(trifluoromethyl)phenyl]benzamide,
5-bromo-2-hydroxy-N-[2-methoxy-5-(trifluoromethyl)phenyl]benzamide,
5-chloro-2-hydroxy-N-[2-methoxy-5-trifluoromethyl)phenyl]benzamide,
5-bromo-2-hydroxy-N-[3-methoxy-5-(trifluoromethyl)phenyl]benzamide,
5-chloro-2-hydroxy-N-[4-methoxy-3-(trifluoromethyl)phenyl]benzamide,
5-chloro-2-hydroxy-N-[2-methylsulfanyl-5-(trifluoromethyl)phenyl]benzamide,
5-chloro-2-hydroxy-N-[2-(1-pyrrolidino)-5-(trifluoromethyl)phenyl]benzamide,
5-chloro-2-hydroxy-N-[2"-morpholino-5-(trifluoromethyl)phenyl]benzamide,
5-bromo-N-[5-bromo-4-(trifluoromethyl)thiazol-2-yl]-2-hydroxybenzamide,
5-chloro-N-{5-cyano-4-[(1,1-dimethyl)ethyl]thiazol-2-yl}-2-hydroxybenzamide,
5-bromo-N-{5-cyano-4-[(1,1-dimethyl)ethyl]thiazol-2-yl}-2-hydroxybenzamide,
2-(5-bromo-2-hydroxybenzoyl)amino-4 (trifluoromethyl) thiazol-5-carboxylic acid ethylester.

1.3. Method 1 wherein A is $C_{1-4}$ acyl (e.g. acetyl).
1.4. Method 1 wherein the compound is a compound of formula I as described in U.S. Pat. No. 7,626,042, for example of formula I-1, e.g. any of Compound Nos. 1-151 as described in U.S. Pat. No. 7,626,042.
1.5. Method 1.4 wherein A is $C_{1-4}$ acyl (e.g. acetyl).
1.6. Method 1 wherein A is the residue of an amino acid.
1.7. Method 1 wherein A is a 5 to 6-membered non-aromatic heterocyclic ring-carbonyl group, for example a 5 to 6-membered non-aromatic heterocyclic ring-carbonyl group which comprises at least one nitrogen atom as ring-constituting atoms (ring forming atoms) of said heterocyclic ring and binds to the carbonyl group at the nitrogen atom, e.g., wherein said 5 to 6-membered non-aromatic heterocyclic ring is selected from 1-pyrrolidinyl group, piperidino group, morpholino group, and 1-piperazinyl group, and said heterocyclic ring may be substituted with one or more substituents, e.g., independently selected from an alkyl group, an alkyl-oxy-carbonyl group, and a carboxy group; for example wherein A is (morpholin-4-yl)carbonyl.

1.8. Method 1 wherein A is a N,N-di-substituted carbamoyl group, wherein two substituents of said carbamoyl group may combine to each other, together with the nitrogen atom to which they bind, to form a nitrogen-containing heterocyclic group which may be substituted.

1.9. Method 1 wherein A is (morpholin-4-yl)carbonyl.

1.10. Method 1 wherein A is a phosphono group, which may be substituted, e.g., dibenzyl phosphono, or unsubstituted.

1.11. Method 1 wherein the compound of Formula I is a compound of formula 1a:

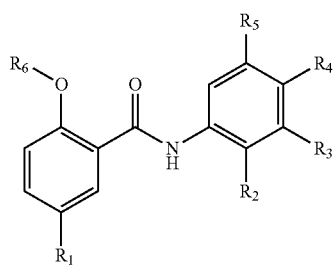

wherein $R_1$, $R_2$, $R_3$, $R_4$, and $R_5$ are selected from H, halo, halogenated $C_{1-4}$ alkyl (e.g., trifluoromethyl), and cyano; and $R_6$ is selected from H and physiologically hydrolysable and acceptable acyl, e.g., wherein $R_6$ is A as hereinbefore defined in any of Methods 1-1.9;

in free, pharmaceutically acceptable salt form.

1.12. Method 1.11 wherein the compound of Formula I is a compound of formula 1a wherein $R_1$ is selected from trifluoromethyl, chloro, fluoro, and bromo; $R_3$ and $R_5$ are the same or different and selected from trifluoromethyl, chloro, fluoro, and bromo; and $R_2$ and $R_4$ are both H.

1.13. Method 1.12 wherein the compound of Formula I is a compound of formula 1a wherein $R_1$ is selected from chloro and bromo; $R_3$ and $R_5$ are both trifluoromethyl; and $R_2$, $R_4$ and $R_6$ are all H, e.g., wherein the compound of formula 1a is selected from:

Compound 1

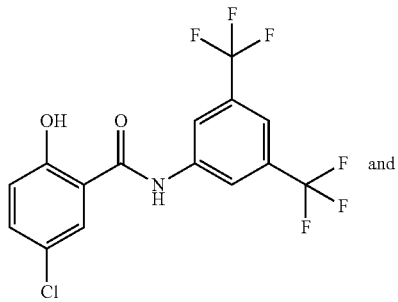

and

Compound 2

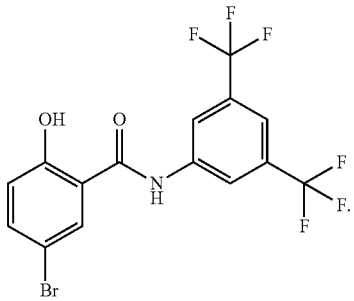 [SMILES: O=C(Nc1cc(C(F)(F)F)cc(C(F)(F)F)c1)c1cc(Cl)ccc1O]

1.14. Method 1.11 or 1.12 wherein $R_6$ is H.

1.15. Method 1.11 or 1.12 wherein $R_6$ is acetyl.

1.16. Method 1.11 or 1.12 wherein the compound of Formula I is a compound of formula 1a wherein $R_1$ is selected from chloro and bromo; $R_3$ and $R_5$ are both trifluoromethyl; and $R_2$ and $R_4$ are H and $R_6$ is acetyl, e.g., wherein the compound of formula 1a is selected from:

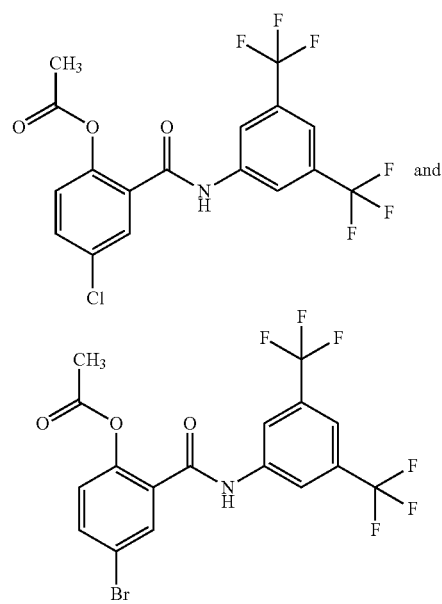

and 1.17. Method 1.13 wherein the compound of formula 1a is Compound 1

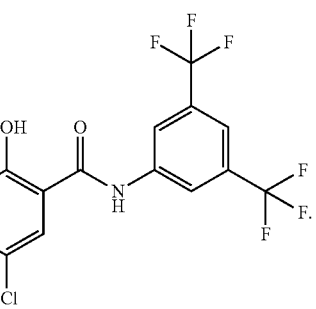

1.18. Method 1.12 wherein the compound of Formula I is a compound of formula 1a wherein $R_1$, $R_3$ and $R_5$ are each chloro, and $R_2$, $R_4$ and $R_6$ are each H (Compound 3).

1.19. Method 1.12 wherein the compound of Formula I is a compound of formula 1a wherein $R_1$, $R_3$ and $R_5$ are each trifluoromethyl, and $R_2$, $R_4$ and $R_6$ are each H (Compound 4).

1.20. Method 1.11 or 1.12 wherein the compound of Formula I is a compound of formula 1a, and $R_6$ is $C_{1-4}$ acyl (e.g. acetyl).

1.21. Method 1.11 or 1.12 wherein the compound of Formula I is a compound of formula 1a, and $R_6$ is the residue of an amino acid.

1.22. Method 1.11 or 1.12 wherein the compound of Formula I is a compound of formula 1a, and $R_6$ is a 5 to 6-membered non-aromatic heterocyclic ring-carbonyl group, for example a 5 to 6-membered non-aromatic heterocyclic ring-carbonyl group which comprises at least one nitrogen atom as ring-constituting atoms (ring forming atoms) of said heterocyclic ring and binds to the carbonyl group at the nitrogen atom, e.g., wherein said 5 to 6-membered non-aromatic heterocyclic ring is selected from 1-pyrrolidinyl group, piperidino group, morpholino group, and 1-piperazinyl group, and said heterocyclic ring may be substituted with one or more substituents, e.g., independently selected from an alkyl group, an alkyl-oxy-carbonyl group, and a carboxy group; for example wherein $R_6$ is (morpholin-4-yl)carbonyl.

1.23. Method 1.11 or 1.12 wherein the compound of Formula I is a compound of formula 1a, and $R_6$ is a N,N-di-substituted carbamoyl group, wherein two substituents of said carbamoyl group may combine to each other, together with the nitrogen atom to which they bind, to form a nitrogen-containing heterocyclic group which may be substituted.

1.24. Method 1.11 or 1.12 wherein the compound of Formula I is a compound of formula 1a, and $R_6$ is a (morpholin-4-yl)carbonyl group.

1.25. Method 1.11 or 1.12 wherein the compound of Formula I is a compound of formula 1a, and $R_6$ is a phosphono group, which may be substituted, e.g. dibenzylphosphono, or unsubstituted.

1.26. Method 1.25 wherein the compound of formula 1a is selected from:

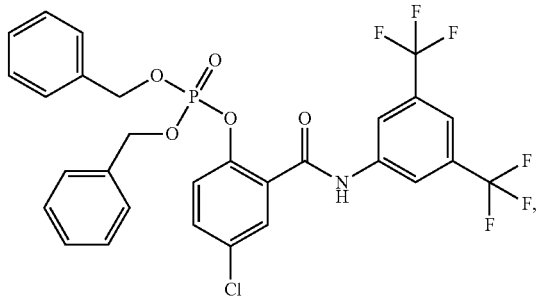

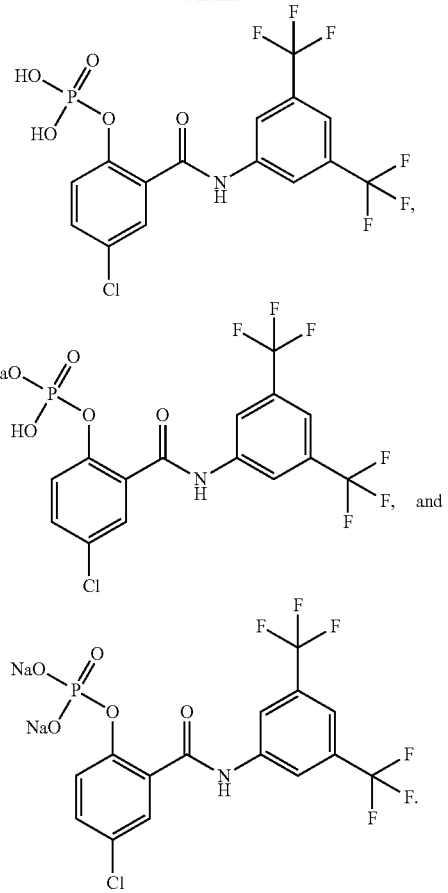

1.27. Method 1.26 wherein the compound of formula 1a is Compound 5

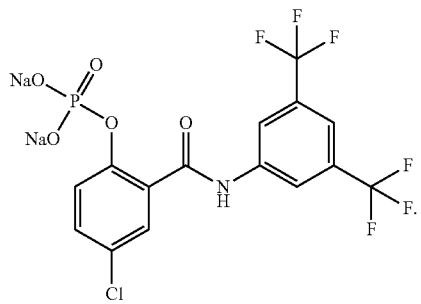

1.28. Method 1 wherein the phenylbenzamide compound is niclosamide or the compound shown below

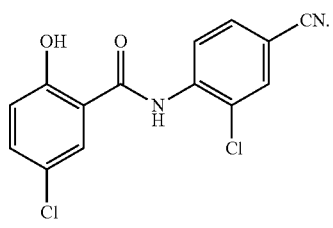 [SMILES: N#Cc1ccc(NC(=O)c2cc(Cl)ccc2O)c(Cl)c1]

1.29. Any of Method 1, et seq. wherein the aquaporin is AQP4.

1.30. Any of Method 1, et seq. wherein the condition to be treated or controlled is selected from edema, e.g. edema of the brain or spinal cord, e.g., cerebral edema, e.g. cerebral edema consequent to head trauma, ischemic stroke, glioma, meningitis, acute mountain sickness, epileptic seizures, infections, metabolic disorders, water intoxication, hepatic failure, hepatic encephalopathy, or diabetic ketoacidosis or, e.g., spinal cord edema, e.g., spinal cord edema consequent to spinal cord trauma, e.g., spinal cord compression.

1.31. Method 1.30 further comprising a treatment selected from one or more of the following: optimal head and neck positioning to facilitate venous outflow, e.g. head elevation 30°; avoidance of dehydration; systemic hypotension; maintenance of normothermia or hypothermia; aggressive measures; osmotherapy, e.g., using mannitol or hypertonic saline; hyperventilation; therapeutic pressor therapy to enhance cerebral perfusion; administration of barbiturates to reduce cerebral metabolism ($CMO_2$); hemicraniectomy; administration of aspirin; administration of amantadine; intravenous thrombolysis (e.g. using rtPA); mechanical clot removal; angioplasty; and/or stents.

1.32. Any of Method 1, et seq. wherein the patient is at elevated risk of cerebral edema, e.g., due to head trauma, ischemic stroke, glioma, meningitis, acute mountain sickness, epileptic seizure, infection, metabolic disorder, water intoxication, hepatic failure, hepatic encephalopathy, or diabetic ketoacidosis.

1.33. Method 1.30 wherein the patient has suffered a stroke, head injury, or spinal injury.

1.34. Method 1.33 wherein the patient has suffered a stroke, head injury or spinal injury within 12 hours, e.g. within 6 hours, preferably within 3 hours of commencing treatment.

1.35. Method 1.30 wherein the patient is at elevated risk of suffering a stroke, head injury or spinal injury, e.g., in combat or in an athletic competition.

1.36. Any of Method 1, et seq. wherein the patient already has cerebral edema.

1.37. Any of Method 1, et seq. wherein the condition to be treated or controlled is cerebral edema consequent to a stroke or a traumatic brain injury.

1.38. Any of Method 1, et seq. wherein the condition to be treated or controlled is cerebral edema consequent to a middle cerebral artery stroke.

1.39. Any of Method 1, et seq. wherein the condition to be treated or controlled is cerebral edema consequent to closed head trauma.

1.40. Any of Methods 1-1.32 wherein the condition to be treated or controlled is cerebral edema consequent to an epileptic seizure.

1.41. Any of Methods 1-1.32 wherein the condition to be treated or controlled is cerebral edema consequent to an infection.

1.42. Any of Methods 1-1.32 wherein the condition to be treated or controlled is cerebral edema consequent to a metabolic disorder.

1.43. Any of Methods 1-1.32 wherein the condition to be treated or controlled is cerebral edema consequent to glioma.

1.44. Any of Methods 1-1.32 wherein the condition to be treated or controlled is cerebral edema consequent to meningitis, acute mountain sickness, or water intoxication.

1.45. Any of Methods 1-1.32 wherein the condition to be treated or controlled is cerebral edema consequent to hepatic failure, hepatic encephalopathy, or diabetic ketoacidosis.

1.46. Any of Methods 1-1.31 wherein the condition to be treated or controlled is cerebral edema consequent to an abscess.

1.47. Any of Methods 1-1.31 wherein the condition to be treated or controlled is cerebral edema consequent to eclampsia.

1.48. Any of Methods 1-1.31 wherein the condition to be treated or controlled is cerebral edema consequent to Creutzfeldt-Jakob disease.

1.49. Any of Methods 1-1.31 wherein the condition to be treated or controlled is cerebral edema consequent to lupus cerebritis.

1.50. Any of Methods 1-1.31 wherein the condition to be treated or controlled is edema consequent to hypoxia, e.g., general systemic hypoxia, e.g., hypoxia caused by an interruption of blood perfusion, for example wherein the edema is cerebral edema consequent to hypoxia caused by cardiac arrest, stroke, or other interruption of blood perfusion to the brain, or wherein the edema is cardiac edema consequent to cardiac ischemia or other interruption of blood flow to the heart.

1.51. Any of Methods 1-1.31 wherein the condition to be treated or controlled is cerebral and/or optic nerve edema consequent to microgravity and/or radiation exposure, e.g., exposure from space flight or from working with radioactive materials or from working in radioactive areas.

1.52. Any of Methods 1-1.31 wherein the condition to be treated or controlled is cerebral edema consequent to an invasive central nervous system procedures, e.g., neurosurgery, endovascular clot removal, spinal tap, aneurysm repair, or deep brain stimulation.

1.53. Method 1.51 or 1.52 wherein the patient is at elevated risk of edema, e.g., due to microgravity and/or radiation exposure, neurosurgery, endovascular clot removal, spinal tap, aneurysm repair, or deep brain stimulation.

1.54. Method 1.51 or 1.52 wherein the patient already has edema.

1.55. Any of Methods 1, et seq. wherein the edema is cytotoxic cerebral edema or is primarily cytotoxic cerebral edema.

1.56. Any of Methods 1-1.45 or 1.50 wherein the edema is cytotoxic cerebral edema or is primarily cytotoxic cerebral edema.

1.57. Any of Methods 1-1.30 wherein the condition to be treated or controlled is spinal cord edema, e.g., spinal cord edema consequent to a spinal cord trauma, e.g., spinal cord compression.

1.58. Method 1.57 wherein the condition to be treated or controlled is spinal cord edema consequent to spinal cord compression.

1.59. Any of Methods 1-1.30 wherein the condition to be treated or controlled is retinal edema.

1.60. Any of Methods 1-1.29 wherein the condition to be treated or controlled is epilepsy.

1.61. Any of Methods 1-1.29 wherein the condition to be treated or controlled is retinal ischemia or other diseases of the eye associated with abnormalities in intraocular pressure and/or tissue hydration.

1.62. Any of Methods 1-1.29 wherein the condition to be treated or controlled is myocardial ischemia.

1.63. Any of Methods 1-1.29 wherein the condition to be treated or controlled is myocardial ischemia/reperfusion injury.
1.64. Any of Methods 1-1.29 wherein the condition to be treated or controlled is myocardial infarction.
1.65. Any of Methods 1-1.29 wherein the condition to be treated or controlled is myocardial hypoxia.
1.66. Any of Methods 1-1.29 wherein the condition to be treated or controlled is congestive heart failure.
1.67. Any of Methods 1-1.29 wherein the condition to be treated or controlled is sepsis.
1.68. Any of Methods 1-1.29 wherein the condition to be treated or controlled is a migraine.
1.69. Any of Methods 1-1.28 wherein the aquaporin is AQP2.
1.70. Any of Methods 1-1.28 or 1.69 wherein the condition to be treated is hyponatremia or excessive fluid retention, e.g., consequent to heart failure (HF), for example congestive heart failure, liver cirrhosis, nephrotic disorder, or syndrome of inappropriate antidiuretic hormone secretion (SIADH).
1.71. Any of Methods 1-1.28 or 1.69-1.70 further comprising one or more of restriction of dietary sodium, fluid and/or alcohol; and/or administration of one or more diuretics, vasopressin receptor antagonists, angiotensin converting enzyme (ACE) inhibitors, aldosterone inhibitors, angiotensin receptor blockers (ARBs), beta-adrenergic antagonists (beta-blockers), and/or digoxin.
1.72. Any of Method 1, et seq. wherein the niclosamide or the compound of Formula I or formula 1a inhibits aquaporin activity, e.g., AQP2 and/or AQP4 activity, by at least 50% at concentrations of 10 micromolar or less, for example inhibits APQ2 and/or AQP4 activity by at least 50% at concentrations of 10 micromolar or less in an aquaporin-mediated cell volume change assay, e.g., is active in any of the assays of Method 10, et seq. infra.
1.73. Any of Methods 1-1.29 wherein the condition to be treated or controlled is neuromyelitis optica.
1.74. Any of Method 1, et seq. wherein the niclosamide or the compound of Formula I or formula 1a is administered orally.
1.75. Any of Method 1, et seq. wherein the niclosamide or the compound of Formula I or formula 1a is administered parenterally.
1.76. Method 1.75 wherein the niclosamide or the compound of Formula I or formula 1a is administered intravenously.
1.77. Any of Method 1, et seq. wherein the patient is human.
1.78. Any of Method 1, et seq. wherein the onset of action of any of the compounds identified in Methods 1-1.28 is fairly rapid.

The invention further provides a phenylbenzamide, e.g. niclosamide or a compound of Formula I or formula 1a as hereinbefore described, for use in treating or controlling a disease or condition mediated by an aquaporin, e.g., in any of Methods 1, 1.1, et seq.

The invention further provides a phenylbenzamide, e.g. niclosamide or a compound of Formula I or formula 1a as hereinbefore described, in the manufacture of a medicament for treating or controlling a disease or condition mediated by an aquaporin, e.g., for use in any of Methods 1, 1.1, et seq.

The invention further provides a pharmaceutical composition comprising a phenylbenzamide, e.g. niclosamide or a compound of Formula I or formula 1a as hereinbefore described, in combination with a pharmaceutically acceptable diluent or carrier for use in treating or controlling a disease or condition mediated by an aquaporin, e.g., in any of Methods 1, 1.1, et seq.

Phenylbenzamides, e.g. of Formula I or formula 1a as hereinbefore described, may exist in free or salt form, e.g., as acid addition salts. In this specification unless otherwise indicated language such as "compound of Formula I or formula 1a" or "compounds of Formula I or formula 1a" is to be understood as embracing the compounds in any form, for example free base or acid addition salt form. Pharmaceutically acceptable salts are known in the art and include salts which are physiologically acceptable at the dosage amount and form to be administered, for example hydrochlorides.

Examples of the acyl group include, for example, formyl, glyoxyloyl group, thioformyl group, carbamoyl group, thiocarbamoyl group, sulfamoyl group, sulfinamoyl group, carboxy group, sulfo group, phosphono group, and groups represented by the following formulas:

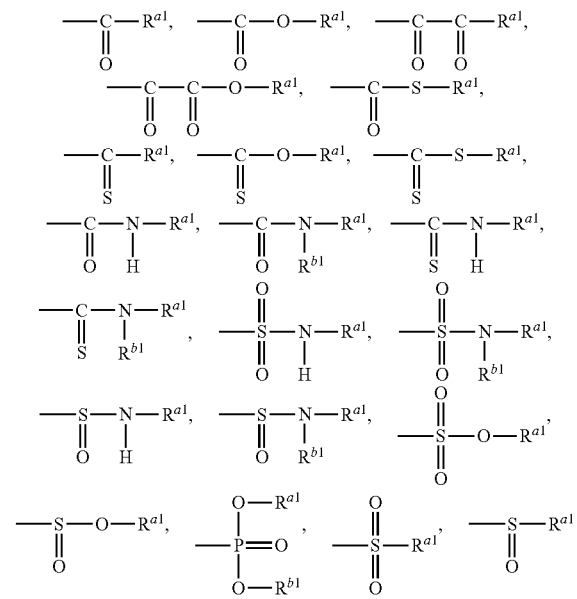

wherein $R^{a1}$ and $R^{b1}$ may be the same or different and represent a hydrocarbon group or a heterocyclic group, or $R^{a1}$ and $R^{b1}$ combine to each other, together with the nitrogen atom to which they bind, to form a cyclic amino group. Acyl includes physiologically hydrolysable and acceptable acyl group. Examples of the acyl group of "an acyl group which may be substituted" as used herein, e.g., in relation to "A" include similar groups to the acyl group in the aforementioned definition. "A" is a group selected from the following substituent group ω:

[Substituent group ω] a hydrocarbon-carbonyl group which may be substituted, a heterocyclic ring-carbonyl group which may be substituted, a hydrocarbon-oxy-carbonyl group which may be substituted, a hydrocarbon-sulfonyl group which may be substituted, a sulfamoyl group which may be substituted, a sulfo group which may be substituted, a phosphono group which may be substituted, and a carbamoyl group which may be substituted. By the term "physiologically hydrolysable and acceptable acyl" as used herein, e.g., in relation to "A" or "$R_6$" in compounds of Formula I or formula 1a, is meant a residue of an acid, for example a carboxylic acid, a carbamic acid or a phosphoric acid (e.g., optionally substituted carbonyl such as acetyl or the residue of an amino acid, optionally substituted carbamoyl, e.g. (morpholin-4-yl)carbonyl, or optionally substituted phosphono e.g., dibenzylphosphono), linked to an oxygen, e.g., as depicted in Formula 1 or formula 1a above, e.g. to form an ester or phosphoester with a compound of Formula I or formula 1a, which is capable of hydrolysis from said oxygen under physiological conditions to yield an acid which is physiologically tolerable at doses to be administered, together with the corresponding hydroxy compound of Formula I or formula 1a wherein A or $R_6$ is H. As will be appreciated the term thus embraces conventional pharmaceutical prodrug forms, although it is not necessarily required that the compounds must be hydrolyzed in order to be active. The acyl compounds may be prepared by conventional means, e.g., by acylation of a compound of Formula 1 or formula 1a, wherein A or $R_6$ is H, with the desired acid or acid halide. Examples of acylated compounds and methods of making them are provided, e.g., in US 2010/0274051 A1, U.S. Pat. No. 7,700,655, and in U.S. Pat. No. 7,626,042, each incorporated herein by reference.

The term "patient" includes human or non-human (i.e., animal) patient. In a particular embodiment, the invention encompasses both human and nonhuman. In another embodiment, the invention encompasses nonhuman. In another embodiment, the term encompasses human.

The term "fairly rapid" with respect to onset of action means that the time it takes after a compound is administered for a response to be observed is 30 minutes or less, for example 20 minutes or less, for example or 15 minutes or less, for example 10 minutes or less, for example 5 minutes or less, for example 1 minute or less.

Phenylbenzamides, e.g. of Formula 1 or formula 1a as hereinbefore described for use in the methods of the invention may be used as a sole therapeutic agent, but may also be used in combination or for co-administration with other active agents, for example in conjunction with conventional therapies for cerebral edema, stroke, traumatic brain injury, glioma, meningitis, acute mountain sickness, infection, metabolic disorder, hypoxia, water intoxication, hepatic failure, hepatic encephalopathy, diabetic ketoacidosis, abscess, eclampsia, Creutzfeldt-Jakob disease, lupus cerebritis, edema of the optic nerve, hyponatremia, fluid retention, epilepsy, retinal ischemia or other diseases of the eye associated with abnormalities in intraocular pressure and/or tissue hydration, myocardial ischemia, myocardial ischemia/reperfusion injury, myocardial infarction, myocardial hypoxia, congestive heart failure, sepsis, neuromyelitis optica, or migraines.

In a further embodiment, the invention provides a method (Method 2) of treating or controlling edema, e.g. edema of the brain or spinal cord, e.g., cerebral edema, e.g. cerebral edema consequent to head trauma, ischemic stroke, glioma, meningitis, acute mountain sickness, epileptic seizures, infections, metabolic disorders, hypoxia, water intoxication, hepatic failure, hepatic encephalopathy, diabetic ketoacidosis, abscess, eclampsia, Creutzfeldt-Jakob disease, or lupus cerebritis, as well as edema consequent to microgravity and/or radiation exposure, as well as edema consequent to invasive central nervous system procedures, e.g., neurosurgery, endovascular clot removal, spinal tap, aneurysm repair, or deep brain stimulation or, e.g., retinal edema or, e.g., spinal cord edema, e.g., spinal cord edema consequent to spinal cord trauma, e.g., spinal cord compression, comprising administering an effective amount of an inhibitor of AQP4, e.g, a compound binding to AQP4, to a patient in need thereof, e.g., wherein the inhibitor of AQP4 is selected from phenylbenzamides, e.g. niclosamide or a compound of Formula I or formula 1a as hereinbefore described, e.g., any of the compounds identified in Methods 1-1.28 above, for example 2.

2.1. Method 2 further comprising a treatment selected from one or more of the following: optimal head and neck positioning to facilitate venous outflow, e.g. head elevation 30°; avoidance of dehydration; systemic hypotension; maintenance of normothermia or hypothermia; aggressive measures; osmotherapy, e.g., using mannitol or hypertonic saline; hyperventilation; therapeutic pressor therapy to enhance cerebral perfusion; administration of barbiturates to reduce of cerebral metabolism ($CMO_2$); hemicraniectomy; administration of aspirin; administration of amantadine; intravenous thrombolysis (e.g. using rtPA); mechanical clot removal; angioplasty; and/or stents.

2.2. Method 2 or 2.1 wherein the patient is at elevated risk of cerebral edema, e.g., due to head trauma, ischemic stroke, glioma, meningitis, acute mountain sickness epileptic seizure, infection, metabolic disorder, water intoxication, hepatic failure, hepatic encephalopathy, or diabetic ketoacidosis.

2.3. Method 2, 2.1, or 2.2 wherein the patient has suffered a stroke, head injury, or spinal injury.

2.4. Any of Method 2, et seq. wherein the patient has suffered a stroke, head injury or spinal injury within 12 hours, e.g. within 6 hours, preferably within 3 hours of commencing treatment.

2.5. Any of Method 2, et seq. wherein the patient is at elevated risk of suffering a stroke, head injury or spinal injury, e.g., in combat or in an athletic competition.

2.6. Any of Method 2, et seq. wherein the patient already has cerebral edema.

2.7. Any of Method 2, et seq. wherein the condition to be treated or controlled is cerebral edema consequent to a stroke or a traumatic brain injury.

2.8. Any of Method 2, et seq. wherein the condition to be treated or controlled is cerebral edema consequent to a middle cerebral artery stroke.

2.9. Any of Method 2, et seq. wherein the condition to be treated or controlled is cerebral edema consequent to a closed head trauma.

2.10. Any of Methods 2-2.2 wherein the condition to be treated or controlled is cerebral edema consequent to an epileptic seizure.

2.11. Any of Methods 2-2.2 wherein the condition to be treated or controlled is cerebral edema consequent to an infection.

2.12. Any of Methods 2-2.2 wherein the condition to be treated or controlled is cerebral edema consequent to a metabolic disorder.

2.13. Any of Methods 2-2.2 wherein the condition to be treated or controlled is cerebral edema consequent to glioma.

2.14. Any of Methods 2-2.2 wherein the condition to be treated or controlled is cerebral edema consequent to meningitis, acute mountain sickness, or water intoxication.

2.15. Any of Methods 2-2.2 wherein the condition to be treated or controlled is cerebral edema consequent to hepatic failure, hepatic encephalopathy, or diabetic ketoacidosis.

2.16. Method 2 or 2.1 wherein the condition to be treated or controlled is cerebral edema consequent to an abscess.

2.17. Method 2 or 2.1 wherein the condition to be treated or controlled is cerebral edema consequent to eclampsia.
2.18. Method 2 or 2.1 wherein the condition to be treated or controlled is cerebral edema consequent to Creutzfeldt-Jakob disease.
2.19. Method 2 or 2.1 wherein the condition to be treated or controlled is cerebral edema consequent to lupus cerebritis.
2.20. Method 2 or 2.1 wherein the condition to be treated or controlled is cerebral and/or optic nerve edema consequent to microgravity exposure, e.g., exposure from space flight or from working with radioactive materials or from working in radioactive areas.
2.21. Method 2 or 2.1 wherein the condition to be treated or controlled is cerebral edema consequent to invasive central nervous system procedures, e.g., neurosurgery, endovascular clot removal, spinal tap, aneurysm repair, or deep brain stimulation.
2.22. Method 2.20 or 2.21 wherein the patient is at elevated risk of edema, e.g., due to microgravity and/or radiation exposure, neurosurgery, endovascular clot removal, spinal tap, aneurysm repair, or deep brain stimulation.
2.23. Method 2.20 or 2.21 wherein the patient already has edema.
2.24. Any of Methods 2, et seq. wherein the edema is cytotoxic cerebral edema or is primarily cytotoxic cerebral edema.
2.25. Any of Methods 2-2.15, et seq. wherein the edema is cytotoxic cerebral edema or is primarily cytotoxic cerebral edema.
2.26. Method 2 wherein the condition to be treated or controlled is spinal cord edema, e.g., spinal cord edema consequent to spinal cord trauma, e.g., spinal cord compression.
2.27. Method 2.26 wherein the condition to be treated or controlled is spinal cord edema consequent to spinal cord compression.
2.28. Method 2 wherein the condition to be treated or controlled is retinal edema.
2.29. Any of Method 2, et seq. wherein the AQP4 inhibitor inhibits AQP4 activity by at least 50% at concentrations of 10 micromolar or less, for example inhibits AQP4 activity by at least 50% at concentrations of 10 micromolar or less in an aquaporin-mediated cell volume change assay, e.g., is active in any of the assays of Method 10, et seq. infra.
2.30. Any of Method 2, et seq. wherein the duration of treatment with an AQP4 inhibitor is less than 21 days, e.g., less than 2 weeks, e.g., one week or less.
2.31. Any of Method 2, et seq. wherein the AQP4 inhibitor is administered orally.
2.32. Any of Method 2, et seq. wherein the AQP4 inhibitor is administered parenterally.
2.33. Method 2.32 wherein the AQP4 inhibitor is administered intravenously.
2.34. Any of Method 2, et seq. wherein the patient is human.
2.35. Any of Method 2, et seq. wherein the onset of action of any of the compounds identified in Methods 1-1.28 is fairly rapid.
2.36. Any of Method 2, et seq. wherein the edema is consequent to hypoxia, e.g., general systemic hypoxia, e.g., hypoxia caused by an interruption of blood perfusion, for example wherein the edema is cerebral edema consequent to hypoxia caused by cardiac arrest or other interruption of blood perfusion to the brain.

In a further embodiment, the invention provides a method (Method 3) of treating or controlling a condition selected from hyponatremia and excessive fluid retention, e.g., consequent to heart failure (HF), for example congestive heart failure, liver cirrhosis, nephrotic disorder, or syndrome of inappropriate antidiuretic hormone secretion (SIADH) comprising administering an effective amount of an inhibitor of AQP2, e.g., a compound binding to AQP2, e.g., to a patient in need thereof, e.g., wherein the inhibitor of AQP2 is selected from phenylbenzamides, e.g. niclosamide or a compound of Formula I or formula 1a as hereinbefore described, e.g., any of the compounds identified in Methods 1-1.28 above, for example
3.
3.1. Method 3 further comprising one or more of restriction of dietary sodium, fluid and/or alcohol; and/or administration of one or more diuretics, vasopressin receptor antagonists, angiotensin converting enzyme (ACE) inhibitors, aldosterone inhibitors, angiotensin receptor blockers (ARBs), beta-adrenergic antagonists (beta-blockers), and/or digoxin.
3.2. Any of Method 3, et seq. wherein the AQP2 inhibitor inhibits AQP2 activity by at least 50% at concentrations of 10 micromolar or less, for example inhibits APQ2 activity by at least 50% at concentrations of 10 micromolar or less in an aquaporin-mediated cell volume change assay, e.g., is active in any of the assays of Method 10, et seq. infra.
3.3. Any of Method 3, et seq. wherein the AQP2 inhibitor is administered orally.
3.4. Any of Method 3, et seq. wherein the AQP2 inhibitor is administered parenterally.
3.5. Method 3.4 wherein the AQP2 inhibitor is administered intravenously.
3.6. Any of Method 3, et seq. wherein the patient is human.
3.7. Any of Method 3, et seq. wherein the onset of action of any of the compounds identified in Methods 1-1.28 is fairly rapid.

In a further embodiment, the invention provides a method (Method 4) of treating or controlling a condition selected from epilepsy, retinal ischemia or other diseases of the eye associated with abnormalities in intraocular pressure and/or tissue hydration, myocardial ischemia, myocardial ischemia/reperfusion injury, myocardial infarction, myocardial hypoxia, congestive heart failure, sepsis, neuromyelitis optica, or migraines comprising administering an effective amount of an inhibitor of AQP4, e.g, a compound binding to AQP4, to a patient in need thereof, e.g., wherein the inhibitor of AQP4 is selected from phenylbenzamides, e.g. niclosamide or a compound of Formula I or formula 1a as hereinbefore described, e.g., any of the compounds identified in Method 1-1.28 above, for example
4.
4.1. Method 4 wherein the condition to be treated or controlled is retinal ischemia or other diseases of the eye associated with abnormalities in intraocular pressure and/or tissue hydration.
4.2. Method 4 wherein the condition to be treated or controlled is myocardial ischemia.
4.3. Method 4 wherein the condition to be treated or controlled is myocardial ischemia/reperfusion injury.
4.4. Method 4 wherein the condition to be treated or controlled is myocardial infarction.

4.5. Method 4 wherein the condition to be treated or controlled is myocardial hypoxia.
4.6. Method 4 wherein the condition to be treated or controlled is congestive heart failure.
4.7. Method 4 wherein the condition to be treated or controlled is sepsis.
4.8. Method 4 wherein the condition to be treated or controlled is neuromyelitis optica.
4.9. Method 4 wherein the condition to be treated or controlled is a migraine.
4.10. Any of Method 4, et seq. wherein the AQP4 inhibitor inhibits AQP4 activity by at least 50% at concentrations of 10 micromolar or less, for example inhibits APQ4 activity by at least 50% at concentrations of 10 micromolar or less in an aquaporin-mediated cell volume change assay, e.g., is active in any of the assays of Method 10, et seq. infra.
4.11. Any of Method 4, et seq. wherein the AQP4 inhibitor is administered orally.
4.12. Any of Method 4, et seq. wherein the AQP4 inhibitor is administered parenterally.
4.13. Method 4.12 wherein the AQP4 inhibitor is administered intravenously.
4.14. Any of Method 4, et seq. wherein the patient is human.
4.15. Any of Method 4, et seq. wherein the onset of action of any of the compounds identified in Methods 1-1.28 is fairly rapid.

In a further embodiment, the invention provides a method (Method 5) of treating or controlling a disease or condition mediated by an aquaporin comprising administering to a patient in need thereof a phenylbenzamide, e.g. niclosamide or a compound of Formula I or formula 1a as hereinbefore described, e.g., any of the compounds identified in Method 1-1.28 above, in an amount effective to inhibit the aquaporin, for example
5.
  5.1. Method 5 wherein the aquaporin is AQP4.
  5.2. Method 5 or 5.1 wherein the condition to be treated or controlled is selected from edema, e.g. edema of the brain or spinal cord, e.g., cerebral edema, e.g. cerebral edema consequent to head trauma, ischemic stroke, glioma, meningitis, acute mountain sickness, epileptic seizures, infections, metabolic disorders, water intoxication, hepatic failure, hepatic encephalopathy, or diabetic ketoacidosis or, e.g., spinal cord edema, e.g., spinal cord edema consequent to spinal cord trauma, e.g., spinal cord compression.
  5.3. Method 5.2 further comprising a treatment selected from one or more of the following: optimal head and neck positioning to facilitate venous outflow, e.g. head elevation 30°; avoidance of dehydration; systemic hypotension; maintenance of normothermia or hypothermia; aggressive measures; osmotherapy, e.g., using mannitol or hypertonic saline; hyperventilation; therapeutic pressor therapy to enhance cerebral perfusion; administration of barbiturates to reduce of cerebral metabolism ($CMO_2$); hemicraniectomy; administration of aspirin; administration of amantadine; intravenous thrombolysis (e.g. using rtPA); mechanical clot removal; angioplasty; and/or stents.
  5.4. Any of Method 5, et seq. wherein the patient is at elevated risk of cerebral edema, e.g., due to head trauma, ischemic stroke, glioma, meningitis, acute mountain sickness, epileptic seizure, infection, metabolic disorder, water intoxication, hepatic failure, hepatic encephalopathy, or diabetic ketoacidosis.
  5.5. Any of Method 5, et seq. wherein the patient has suffered a stroke, head injury, or spinal injury.
  5.6. Any of Method 5, et seq. wherein the patient has suffered a stroke, head injury or spinal injury within 12 hours, e.g. within 6 hours, preferably within 3 hours of commencing treatment.
  5.7. Any of Method 5, et seq. wherein the patient is at elevated risk of suffering a stroke, head injury or spinal injury, e.g., in combat or in an athletic competition.
  5.8. Any of Method 5, et seq. wherein the patient already has cerebral edema.
  5.9. Any of Method 5, et seq. wherein the condition to be treated or controlled is cerebral edema consequent to a stroke or a traumatic brain injury.
  5.10. Any of Method 5, et seq. wherein the condition to be treated or controlled is cerebral edema consequent to a middle cerebral artery stroke.
  5.11. Any of Method 5, et seq. wherein the condition to be treated or controlled is cerebral edema consequent to a closed head trauma.
  5.12. Any of Methods 5-5.4 wherein the condition to be treated or controlled is cerebral edema consequent to an epileptic seizure.
  5.13. Any of Methods 5-5.4 wherein the condition to be treated or controlled is cerebral edema consequent to an infection.
  5.14. Any of Methods 5-5.4 wherein the condition to be treated or controlled is cerebral edema consequent to a metabolic disorder.
  5.15. Any of Methods 5-5.4 wherein the condition to be treated or controlled is cerebral edema consequent to glioma.
  5.16. Any of Methods 5-5.4 wherein the condition to be treated or controlled is cerebral edema consequent to meningitis, acute mountain sickness, or water intoxication.
  5.17. Any of Methods 5-5.4 wherein the condition to be treated or controlled is cerebral edema consequent to hepatic failure, hepatic encephalopathy, or diabetic ketoacidosis.
  5.18. Any of Methods 5-5.3 wherein the condition to be treated or controlled is cerebral edema consequent to an abscess.
  5.19. Any of Methods 5-5.3 wherein the condition to be treated or controlled is cerebral edema consequent to eclampsia.
  5.20. Any of Methods 5-5.3 wherein the condition to be treated or controlled is cerebral edema consequent to Creutzfeldt-Jakob disease.
  5.21. Any of Methods 5-5.3 wherein the condition to be treated or controlled is cerebral edema consequent to lupus cerebritis.
  5.22. Any of Methods 5-5.3 wherein the condition to be treated or controlled is edema consequent to hypoxia, e.g., general systemic hypoxia, e.g., hypoxia caused by an interruption of blood perfusion, for example wherein the edema is cerebral edema consequent to hypoxia caused by cardiac arrest, stroke, or other interruption of blood perfusion to the brain, or wherein the edema is cardiac edema consequent to cardiac ischemia or other interruption of blood flow to the heart.
  5.23. Any of Methods 5-5.3 wherein the condition to be treated or controlled is cerebral and/or optic nerve edema consequent to microgravity and/or radiation exposure, e.g., exposure from space flight or from working with radioactive materials or from working in radioactive areas.

5.24. Any of Methods 5-5.3 wherein the condition to be treated or controlled is cerebral edema consequent to invasive central nervous system procedures, e.g., neurosurgery, endovascular clot removal, spinal tap, aneurysm repair, or deep brain stimulation.

5.25. Method 5.23 or 5.24 wherein the patient is at elevated risk of edema, e.g., due to microgravity and/or radiation exposure, neurosurgery, endovascular clot removal, spinal tap, aneurysm repair, or deep brain stimulation.

5.26. Method 5.23 or 5.24 wherein the patient already has edema.

5.27. Any of Methods 5, et seq. wherein the edema is cytotoxic cerebral edema or is primarily cytotoxic cerebral edema.

5.28. Any of Methods 5-5.17 or 5.22 wherein the edema is cytotoxic cerebral edema or is primarily cytotoxic cerebral edema.

5.29. Method 5 or 5.1 wherein the condition to be treated or controlled is spinal cord edema, e.g., spinal cord edema consequent to spinal cord trauma, e.g., spinal cord compression.

5.30. Method 5.29 wherein the condition to be treated or controlled is spinal cord edema consequent to spinal cord compression.

5.31. Any of Methods 5-5.2 wherein the condition to be treated or controlled is retinal edema.

5.32. Method 5 or 5.1 wherein the condition to be treated or controlled is epilepsy.

5.33. Method 5 or 5.1 wherein the condition to be treated or controlled is retinal ischemia or other diseases of the eye associated with abnormalities in intraocular pressure and/or tissue hydration.

5.34. Method 5 or 5.1 wherein the condition to be treated or controlled is myocardial ischemia.

5.35. Method 5 or 5.1 wherein the condition to be treated or controlled is myocardial ischemia/reperfusion injury.

5.36. Method 5 or 5.1 wherein the condition to be treated or controlled is myocardial infarction.

5.37. Method 5 or 5.1 wherein the condition to be treated or controlled is myocardial hypoxia.

5.38. Method 5 or 5.1 wherein the condition to be treated or controlled is congestive heart failure.

5.39. Method 5 or 5.1 wherein the condition to be treated or controlled is sepsis.

5.40. Method 5 or 5.1 wherein the condition to be treated or controlled is a migraine.

5.41. Method 5 wherein the aquaporin is AQP2.

5.42. Method 5 or 5.41 wherein the condition to be treated is hyponatremia or excessive fluid retention, e.g., consequent to heart failure (HF), for example congestive heart failure, liver cirrhosis, nephrotic disorder, or syndrome of inappropriate antidiuretic hormone secretion (SIADH).

5.43. Method 5.42 further comprising one or more of restriction of dietary sodium, fluid and/or alcohol; and/or administration of one or more diuretics, vasopressin receptor antagonists, angiotensin converting enzyme (ACE) inhibitors, aldosterone inhibitors, angiotensin receptor blockers (ARBs), beta-adrenergic antagonists (beta-blockers), and/or digoxin.

5.44. Any of Method 5, et seq. wherein the compound of Formula I or formula 1a inhibits aquaporin activity, e.g., AQP2 and/or AQP4 activity, by at least 50% at concentrations of 10 micromolar or less, for example inhibits APQ2 and/or AQP4 activity by at least 50% at concentrations of 10 micromolar or less in an aquaporin-mediated cell volume change assay, e.g., is active in any of the assays of Method 10, et seq. infra.

5.45. Any of Method 5, et seq. wherein the duration of treatment with the phenylbenzamide is less than 21 days, e.g., less than 2 weeks, e.g., one week or less.

5.46. Any of Method 5, et seq. wherein the niclosamide or the compound of Formula I or formula 1a is administered orally.

5.47. Any of Method 5, et seq. wherein the niclosamide or the compound of Formula I or formula 1a is administered parenterally.

5.48. Method 5.47 wherein the niclosamide or the compound of Formula I or formula 1a is administered intravenously.

5.49. Any of Method 5, et seq. wherein the patient is human.

5.50. Any of Method 5, et seq. wherein the onset of action of any of the compounds identified in Methods 1-1.28 is fairly rapid.

In a further embodiment, the invention provides a method (Method 6) of inhibiting an aquaporin comprising contacting the aquaporin with an effective amount of a phenylbenzamide, e.g. niclosamide or a compound of Formula I or formula 1a as hereinbefore described, e.g., any of the compounds identified in Method 1-1.28 above, for example 6.

6.1. Method 6 wherein the aquaporin is inhibited in vivo.

6.2. Method 6 wherein the aquaporin is inhibited in vitro.

6.3. Any of Methods 6, et seq. wherein the aquaporin is AQP4.

6.4. Any of Method 6, et seq. wherein the aquaporin is AQP2.

6.5. Any of Method 6, et seq. wherein the compound of Formula I or formula 1a inhibits aquaporin activity, e.g., AQP2 and/or AQP4 activity, by at least 50% at concentrations of 10 micromolar or less, for example inhibits APQ2 and/or AQP4 activity by at least 50% at concentrations of 10 micromolar or less in an aquaporin-mediated cell volume change assay, e.g., is active in any of the assays of Method 10, et seq. infra.

6.6. Method 6.1 wherein the niclosamide or the compound of Formula I or formula 1a is administered orally.

6.7. Method 6.1 wherein the niclosamide or the compound of Formula I or formula 1a is administered parenterally.

6.8. Method of 6.7 wherein the niclosamide or the compound of Formula I or formula 1a is administered intravenously.

In a further embodiment, the invention provides a method (Method 7) to inhibit an aquaporin in a patient suffering from a disease or condition mediated by an aquaporin comprising administering an effective amount of a phenylbenzamide, e.g. niclosamide or a compound of Formula I or formula 1a as hereinbefore described, e.g., any of the compounds identified in Method 1-1.28 above, to inhibit the aquaporin.

7.

7.1. Method 7 wherein the aquaporin is AQP4.

7.2. Method 7 or 7.1 wherein the condition to be treated or controlled is selected from edema, e.g. edema of the brain or spinal cord, e.g., cerebral edema, e.g. cerebral edema consequent to head trauma, ischemic stroke, glioma, meningitis, acute mountain sickness, epileptic seizure, infection, metabolic disorder, water intoxication, hepatic failure, hepatic encephalopathy, or diabetic ketoacidosis or, e.g., spinal cord edema, e.g., spinal cord edema consequent to spinal cord trauma, e.g., spinal cord compression.

7.3. Method 7.2 further comprising a treatment selected from one or more of the following: optimal head and neck positioning to facilitate venous outflow, e.g. head elevation 30°; avoidance of dehydration; systemic hypotension; maintenance of normothermia or hypothermia; aggressive measures; osmotherapy, e.g., using mannitol or hypertonic saline; hyperventilation; therapeutic pressor therapy to enhance cerebral perfusion; administration of barbiturates to reduce of cerebral metabolism ($CMO_2$); hemicraniectomy; administration of aspirin; administration of amantadine; intravenous thrombolysis (e.g. using rtPA); mechanical clot removal; angioplasty; and/or stents.

7.4. Any of Method 7, et seq. wherein the patient is at elevated risk of cerebral edema, e.g., due to head trauma, ischemic stroke, glioma, meningitis, acute mountain sickness, epileptic seizure, infection, metabolic disorder, water intoxication, hepatic failure, hepatic encephalopathy, or diabetic ketoacidosis.

7.5. Any of Method 7, et seq. wherein the patient has suffered a stroke, head injury, or spinal injury.

7.6. Any of Method 7, et seq. wherein the patient has suffered a stroke, head injury or spinal injury within 12 hours, e.g. within 6 hours, preferably within 3 hours of commencing treatment.

7.7. Any of Method 7, et seq. wherein the patient is at elevated risk of suffering a stroke, head injury or spinal injury, e.g., in combat or in an athletic competition.

7.8. Any of Method 7, et seq. wherein the patient already has cerebral edema.

7.9. Any of Method 7, et seq. wherein the condition to be treated or controlled is cerebral edema consequent to a stroke or a traumatic brain injury.

7.10. Any of Method 7, et seq. wherein the condition to be treated or controlled is cerebral edema consequent to a middle cerebral artery stroke.

7.11. Any of Method 7, et seq. wherein the condition to be treated or controlled is cerebral edema consequent to a closed head trauma.

7.12. Any of Methods 7-7.4 wherein the condition to be treated or controlled is cerebral edema consequent to an epileptic seizure.

7.13. Any of Methods 7-7.4 wherein the condition to be treated or controlled is cerebral edema consequent an infection.

7.14. Any of Methods 7-7.4 wherein the condition to be treated or controlled is cerebral edema consequent to a metabolic disorder.

7.15. Any of Methods 7-7.4 wherein the condition to be treated or controlled is cerebral edema consequent to glioma.

7.16. Any of Methods 7-7.4 wherein the condition to be treated or controlled is cerebral edema consequent to meningitis, acute mountain sickness, or water intoxication.

7.17. Any of Methods 7-7.4 wherein the condition to be treated or controlled is cerebral edema consequent to hepatic failure, hepatic encephalopathy, or diabetic ketoacidosis.

7.18. Any of Methods 7-7.3 wherein the condition to be treated or controlled is cerebral edema consequent to an abscess.

7.19. Any of Methods 7-7.3 wherein the condition to be treated or controlled is cerebral edema consequent to eclampsia.

7.20. Any of Methods 7-7.3 wherein the condition to be treated or controlled is cerebral edema consequent to Creutzfeldt-Jakob disease.

7.21. Any of Methods 7-7.3 wherein the condition to be treated or controlled is cerebral edema consequent to lupus cerebritis.

7.22. Any of Methods 7-7.3 wherein the condition to be treated or controlled is edema consequent to hypoxia, e.g., general systemic hypoxia, e.g., hypoxia caused by an interruption of blood perfusion, for example wherein the edema is cerebral edema consequent to hypoxia caused by cardiac arrest, stroke, or other interruption of blood perfusion to the brain, or wherein the edema is cardiac edema consequent to cardiac ischemia or other interruption of blood flow to the heart.

7.23. Any of Methods 7-7.3 wherein the condition to be treated or controlled is cerebral and/or optical nerve edema consequent to microgravity and/or radiation exposure, e.g., exposure from space flight or from working with radioactive materials or from working in radioactive areas.

7.24. Any of Methods 7-7.3 wherein the condition to be treated or controlled is cerebral edema consequent to invasive central nervous system procedures, e.g., neurosurgery, endovascular clot removal, spinal tap, aneurysm repair, or deep brain stimulation.

7.25. Method 7.23 or 7.24 wherein the patient is at elevated risk of edema, e.g., due to microgravity and/or radiation exposure, neurosurgery, endovascular clot removal, spinal tap, aneurysm repair, or deep brain stimulation.

7.26. Method 7.23 or 7.24 wherein the patient already has edema.

7.27. Any of Methods 7, et seq. wherein the edema is cytotoxic cerebral edema or is primarily cytotoxic cerebral edema.

7.28. Any of Methods 7-7.17 or 7.22 wherein the edema is cytotoxic cerebral edema or is primarily cytotoxic cerebral edema.

7.29. Any of Methods 7-7.2 wherein the condition to be treated or controlled is spinal cord edema, e.g., spinal cord edema consequent to spinal cord trauma, e.g., spinal cord compression.

7.30. Method 7.29 wherein the condition to be treated or controlled is spinal cord edema consequent to spinal cord compression.

7.31. Any of Methods 7-7.2 wherein the condition to be treated or controlled is retinal edema.

7.32. Method 7 or 7.1 wherein the condition to be treated or controlled is epilepsy.

7.33. Method 7 or 7.1 wherein the condition to be treated or controlled is retinal ischemia or other diseases of the eye associated with abnormalities in intraocular pressure and/or tissue hydration.

7.34. Method 7 or 7.1 wherein the condition to be treated or controlled is myocardial ischemia.

7.35. Method 7 or 7.1 wherein the condition to be treated or controlled is myocardial ischemia/reperfusion injury.

7.36. Method 7 or 7.1 wherein the condition to be treated or controlled is myocardial infarction.

7.37. Method 7 or 7.1 wherein the condition to be treated or controlled is myocardial hypoxia.

7.38. Method 7 or 7.1 wherein the condition to be treated or controlled is congestive heart failure.

7.39. Method 7 or 7.1 wherein the condition to be treated or controlled is sepsis.

7.40. Method 7 or 7.1 wherein the condition to be treated or controlled is a migraine.

7.41. Method 7 wherein the aquaporin is AQP2.

7.42. Method 7 or 7.41 wherein the condition to be treated is hyponatremia or excessive fluid retention, e.g., consequent to heart failure (HF), for example congestive heart failure, liver cirrhosis, nephrotic disorder, or syndrome of inappropriate antidiuretic hormone secretion (SIADH).

7.43. Method 7.42 further comprising one or more of restriction of dietary sodium, fluid and/or alcohol; and/or administration of one or more diuretics, vasopressin receptor antagonists, angiotensin converting enzyme (ACE) inhibitors, aldosterone inhibitors, angiotensin receptor blockers (ARBs), beta-adrenergic antagonists (beta-blockers), and/or digoxin.

7.44. Any of Method 7, et seq. wherein the compound of Formula I or formula 1a inhibits aquaporin activity, e.g., AQP2 and/or AQP4 activity, by at least 50% at concentrations of 10 micromolar or less, for example inhibits APQ2 and/or AQP4 activity by at least 50% at concentrations of 10 micromolar or less in an aquaporin-mediated cell volume change assay, e.g., is active in any of the assays of Method 10, et seq. infra.

7.45. Any of Method 7, et seq. wherein the duration of treatment with the phenylbenzamide is less than 21 days, e.g., less than 2 weeks, e.g., one week or less.

7.46. Any of Method 7, et seq. wherein the niclosamide or compound of Formula I or formula 1a is administered orally.

7.47. Any of Method 7, et seq. wherein the niclosamide or compound of Formula I or formula 1a is administered parenterally.

7.48. Method 7.47 wherein the niclosamide or compound of Formula I or formula 1a is administered intravenously.

7.49. Any of Method 7, et seq. wherein the patient is human.

7.50. Any of Method 7, et seq. wherein the onset of action of any of the compounds identified in Methods 1-1.28 is fairly rapid.

In a further embodiment, the invention provides a pharmaceutical composition comprising a phenylbenzamide, e.g. niclosamide or a compound of Formula I or formula 1a as hereinbefore described, e.g., any of the compounds identified in Methods 1-1.28 above, for use (Use 8) to inhibit an aquaporin in a patient suffering from a disease or condition mediated by the aquaporin. For example, for use in any of the foregoing methods.

8.
- 8.1. Use 8 wherein the aquaporin is AQP4.
- 8.2. Use 8 or 8.1 wherein the condition to be treated or controlled is selected from edema, e.g. edema of the brain or spinal cord, e.g., cerebral edema, e.g. cerebral edema consequent to head trauma, ischemic stroke, glioma, meningitis, acute mountain sickness, epileptic seizure, infection, metabolic disorder, water intoxication, hepatic failure, hepatic encephalopathy, or diabetic ketoacidosis or, e.g., spinal cord edema, e.g., spinal cord edema consequent to spinal cord trauma, e.g., spinal cord compression.
- 8.3. Use 8.2 further comprising a treatment selected from one or more of the following: optimal head and neck positioning to facilitate venous outflow, e.g. head elevation 30°; avoidance of dehydration; systemic hypotension; maintenance of normothermia or hypothermia; aggressive measures; osmotherapy, e.g., using mannitol or hypertonic saline; hyperventilation; therapeutic pressor therapy to enhance cerebral perfusion; administration of barbiturates to reduce of cerebral metabolism ($CMO_2$); hemicraniectomy; administration of aspirin; administration of amantadine; intravenous thrombolysis (e.g. using rtPA); mechanical clot removal; angioplasty; and/or stents.
- 8.4. Any of Use 8, et seq. wherein the patient is at elevated risk of cerebral edema, e.g., due to head trauma, ischemic stroke, glioma, meningitis, acute mountain sickness, epileptic seizure, infection, metabolic disorder, water intoxication, hepatic failure, hepatic encephalopathy, or diabetic ketoacidosis.
- 8.5. Any of Use 8, et seq. wherein the patient has suffered a stroke, head injury, or spinal injury.
- 8.6. Any of Use 8, et seq. wherein the patient has suffered a stroke, head injury or spinal injury within 12 hours, e.g. within 6 hours, preferably within 3 hours of commencing treatment.
- 8.7. Any of Use 8, et seq. wherein the patient is at elevated risk of suffering a stroke, head injury or spinal injury, e.g., in combat or in an athletic competition.
- 8.8. Any of Use 8, et seq. wherein the patient already has cerebral edema.
- 8.9. Any of Use 8, et seq. wherein the condition to be treated or controlled is cerebral edema consequent to a stroke or a traumatic brain injury.
- 8.10. Any of Use 8, et seq. wherein the condition to be treated or controlled is cerebral edema consequent to a middle cerebral artery stroke.
- 8.11. Any of Use 8, et seq. wherein the condition to be treated or controlled is cerebral edema consequent to a closed head trauma.
- 8.12. Any of Uses 8-8.4 wherein the condition to be treated or controlled is cerebral edema consequent to an epileptic seizure.
- 8.13. Any of Uses 8-8.4 wherein the condition to be treated or controlled is cerebral edema consequent to an infection.
- 8.14. Any of Uses 8-8.4 wherein the condition to be treated or controlled is cerebral edema consequent to a metabolic disorder.
- 8.15. Any of Uses 8-8.4 wherein the condition to be treated or controlled is cerebral edema consequent to glioma.
- 8.16. Any of Uses 8-8.4 wherein the condition to be treated or controlled is cerebral edema consequent to meningitis, acute mountain sickness, or water intoxication.
- 8.17. Any of Uses 8-8.4 wherein the condition to be treated or controlled is cerebral edema consequent to hepatic failure, hepatic encephalopathy, or diabetic ketoacidosis.
- 8.18. Any of the Uses 8-8.3 wherein the condition to be treated or controlled is cerebral edema consequent to an abscess.
- 8.19. Any of the Uses 8-8.3 wherein the condition to be treated or controlled is cerebral edema consequent to eclampsia.
- 8.20. Any of Uses 8-8.3 wherein the condition to be treated or controlled is cerebral edema consequent to Creutzfeldt-Jakob disease.

8.21. Any of Uses 8-8.3 wherein the condition to be treated or controlled is cerebral edema consequent lupus cerebritis.

8.22. Any of Uses 8-8.3 wherein the condition to be treated or controlled is edema consequent to hypoxia, e.g., general systemic hypoxia, e.g., hypoxia caused by an interruption of blood perfusion, for example wherein the edema is cerebral edema consequent to hypoxia caused by cardiac arrest, stroke, or other interruption of blood perfusion to the brain, or wherein the edema is cardiac edema consequent to cardiac ischemia or other interruption of blood flow to the heart.

8.23. Any of Uses 8-8.3 wherein the condition to be treated or controlled is cerebral and/or optic nerve edema consequent to microgravity and/or radiation exposure, e.g., exposure from space flight or from working with radioactive materials or from working in radioactive areas.

8.24. Any of Uses 8-8.3 wherein the condition to be treated or controlled is cerebral edema consequent to invasive central nervous system procedures, e.g., neurosurgery, endovascular clot removal, spinal tap, aneurysm repair, or deep brain stimulation.

8.25. Use 8.23 or 8.24 wherein the patient is at elevated risk of edema, e.g., due to microgravity exposure and/or radiation, neurosurgery, endovascular clot removal, spinal tap, aneurysm repair, or deep brain stimulation.

8.26. Use 8.23 or 8.24 wherein the patient already has edema.

8.27. Any of Uses 8, et seq. wherein the edema is cytotoxic cerebral edema or is primarily cytotoxic cerebral edema.

8.28. Any of Uses 8-8.17 or 8.22 wherein the edema is cytotoxic cerebral edema or is primarily cytotoxic cerebral edema.

8.29. Any of Uses 8-8.2 wherein the condition to be treated or controlled is spinal cord edema, e.g., spinal cord edema consequent to spinal cord trauma, e.g., spinal cord compression.

8.30. Use 8.29 wherein the condition to be treated or controlled is spinal cord edema consequent to spinal cord compression.

8.31. Any of Uses 8-8.2 wherein the condition to be treated or controlled is retinal edema.

8.32. Use 8 or 8.1 wherein the condition to be treated or controlled is epilepsy.

8.33. Use 8 or 8.1 wherein the condition to be treated or controlled is retinal ischemia or other diseases of the eye associated with abnormalities in intraocular pressure and/or tissue hydration.

8.34. Use 8 or 8.1 wherein the condition to be treated or controlled is myocardial ischemia.

8.35. Use 8 or 8.1 wherein the condition to be treated or controlled is myocardial ischemia/reperfusion injury.

8.36. Use 8 or 8.1 wherein the condition to be treated or controlled is myocardial infarction.

8.37. Use 8 or 8.1 wherein the condition to be treated or controlled is myocardial hypoxia.

8.38. Use 8 or 8.1 wherein the condition to be treated or controlled is congestive heart failure.

8.39. Use 8 or 8.1 wherein the condition to be treated or controlled is sepsis.

8.40. Use 8 or 8.1 wherein the condition to be treated or controlled is a migraine.

8.41. Use 8 wherein the aquaporin is AQP2.

8.42. Use 8 or 8.41 wherein the condition to be treated is hyponatremia or excessive fluid retention, e.g., consequent to heart failure (HF), for example congestive heart failure, liver cirrhosis, nephrotic disorder, or syndrome of inappropriate antidiuretic hormone secretion (SIADH).

8.43. Use 8.42 further comprising one or more of restriction of dietary sodium, fluid and/or alcohol; and/or administration of one or more diuretics, vasopressin receptor antagonists, angiotensin converting enzyme (ACE) inhibitors, aldosterone inhibitors, angiotensin receptor blockers (ARBs), beta-adrenergic antagonists (beta-blockers), and/or digoxin.

8.44. Any of Use 8, et seq. wherein the compound of Formula I or formula 1a inhibits aquaporin activity, e.g., AQP2 and/or AQP4 activity, by at least 50% at concentrations of 10 micromolar or less, for example inhibits APQ2 and/or AQP4 activity by at least 50% at concentrations of 10 micromolar or less in an aquaporin-mediated cell volume change assay, e.g., is active in any of the assays of Method 10, et seq. infra.

8.45. Any of Use 8, et seq. wherein the duration of treatment with the phenylbenzamide is less than 21 days, e.g., less than 2 weeks, e.g., one week or less.

8.46. Any of Use 8, et seq. wherein the pharmaceutical composition is administered orally.

8.47. Any of Use 8, et seq. wherein the pharmaceutical composition is administered parenterally.

8.48. Use 8.47 wherein the pharmaceutical composition is administered intravenously.

8.49. Any of Use 8, et seq. wherein the patient is human.

8.50. Any of Use 8, et seq. wherein the onset of action of the pharmaceutical composition is fairly rapid.

In a further embodiment, the invention provides use (Use 9) of a phenylbenzamide, e.g. niclosamide or a compound of Formula I or formula 1a as hereinbefore described, e.g., any of the compounds identified in Methods 1-1.28 above, in the manufacture of a medicament for treating or controlling a disease or condition mediated by an aquaporin wherein the medicament comprises the phenylbenzamide in an amount effective to inhibit the aquaporin. For example, for use in any of the foregoing methods.

9.

9.1. Use 9 wherein the aquaporin is AQP4.

9.2. Any of Use 9 or 9.1 wherein the condition to be treated or controlled is selected from edema, e.g. edema of the brain or spinal cord, e.g., cerebral edema, e.g. cerebral edema consequent to head trauma, ischemic stroke, glioma, meningitis, acute mountain sickness, epileptic seizure, infection, metabolic disorder, water intoxication, hepatic failure, hepatic encephalopathy, or diabetic ketoacidosis or, e.g., spinal cord edema, e.g., spinal cord edema consequent to spinal cord trauma, e.g., spinal cord compression.

9.3. Use 9.2 further comprising a treatment selected from one or more of the following: optimal head and neck positioning to facilitate venous outflow, e.g. head elevation 30°; avoidance of dehydration; systemic hypotension; maintenance of normothermia or hypothermia; aggressive measures; osmotherapy, e.g., using mannitol or hypertonic saline; hyperventilation; therapeutic pressor therapy to enhance cerebral perfusion; administration of barbiturates to reduce of cerebral metabolism ($CMO_2$); hemicraniectomy; administration of aspirin; administration of amantadine; intravenous thrombolysis (e.g. using rtPA); mechanical clot removal; angioplasty; and/or stents.

9.4. Any of Use 9, et seq. wherein the patient is at elevated risk of cerebral edema, e.g., due to head trauma, ischemic stroke, glioma, meningitis, acute mountain sickness, epileptic seizure, infection, metabolic disorder, water intoxication, hepatic failure, hepatic encephalopathy, or diabetic ketoacidosis.

9.5. Any of Use 9, et seq. wherein the patient has suffered a stroke, head injury, or spinal injury.

9.6. Any of Use 9, et seq. wherein the patient has suffered a stroke, head injury or spinal injury within 12 hours, e.g. within 6 hours, preferably within 3 hours of commencing treatment.

9.7. Any of Use 9, et seq. wherein the patient is at elevated risk of suffering a stroke, head injury or spinal injury, e.g., in combat or in an athletic competition.

9.8. Any of Use 9, et seq. wherein the patient already has cerebral edema.

9.9. Any of Use 9, et seq. wherein the condition to be treated or controlled is cerebral edema consequent to a stroke or a traumatic brain injury.

9.10. Any of Use 9, et seq. wherein the condition to be treated or controlled is cerebral edema consequent to a middle cerebral artery stroke.

9.11. Any of Use 9, et seq. wherein the condition to be treated or controlled is cerebral edema consequent to a closed head trauma.

9.12. Any of Uses 9-9.4 wherein the condition to be treated or controlled is cerebral edema consequent to an epileptic seizure.

9.13. Any of Uses 9-9.4 wherein the condition to be treated or controlled is cerebral edema consequent to an infection.

9.14. Any of Uses 9-9.4 wherein the condition to be treated or controlled is cerebral edema consequent to a metabolic disorder.

9.15. Any of Uses 9-9.4 wherein the condition to be treated or controlled is cerebral edema consequent to glioma.

9.16. Any of Uses 9-9.4 wherein the condition to be treated or controlled is cerebral edema consequent to meningitis, acute mountain sickness, or water intoxication.

9.17. Any of Uses 9-9.4 wherein the condition to be treated or controlled is cerebral edema consequent to hepatic failure, hepatic encephalopathy, or diabetic ketoacidosis.

9.18. Any of Uses 9-9.3 wherein the condition to be treated or controlled is cerebral edema consequent to an abscess.

9.19. Any of Uses 9-9.3 wherein the condition to be treated or controlled is cerebral edema consequent to eclampsia.

9.20. Any of Uses 9-9.3 wherein the condition to be treated or controlled is cerebral edema consequent to Creutzfeldt-Jakob disease.

9.21. Any of Uses 9-9.3 wherein the condition to be treated or controlled is cerebral edema consequent to lupus cerebritis.

9.22. Any of Uses 9-9.3 wherein the condition to be treated or controlled is edema consequent to hypoxia, e.g., general systemic hypoxia, e.g., hypoxia caused by an interruption of blood perfusion, for example wherein the edema is cerebral edema consequent to hypoxia caused by cardiac arrest, stroke, or other interruption of blood perfusion to the brain, or wherein the edema is cardiac edema consequent to cardiac ischemia or other interruption of blood flow to the heart.

9.23. Any of Uses 9-9.3 wherein the condition to be treated or controlled is cerebral and/or optic nerve edema consequent to microgravity and/or radiation exposure, e.g., exposure from space flight or from working with radioactive materials or from working in radioactive areas.

9.24. Any of Uses 9-9.3 wherein the condition to be treated or controlled is cerebral edema consequent to invasive central nervous system procedures, e.g., neurosurgery, endovascular clot removal, spinal tap, aneurysm repair, or deep brain stimulation.

9.25. Use 9.24 or 9.25 wherein the patient is at elevated risk of edema, e.g., due to microgravity and/or radiation exposure, neurosurgery, endovascular clot removal, spinal tap, aneurysm repair, or deep brain stimulation.

9.26. Use 9.24 or 9.25 wherein the patient already has edema.

9.27. Any of Uses 9, et seq. wherein the edema is cytotoxic cerebral edema or is primarily cytotoxic cerebral edema.

9.28. Any of Uses 9-9.17 or 9.22 wherein the edema is cytotoxic cerebral edema or is primarily cytotoxic cerebral edema.

9.29. Any of Uses 9-9.2 wherein the condition to be treated or controlled is spinal cord edema, e.g., spinal cord edema consequent to spinal cord trauma, e.g., spinal cord compression.

9.30. Use 9.29 wherein the condition to be treated or controlled is spinal cord edema consequent to spinal cord compression.

9.31. Any of Uses 9-9.2 wherein the condition to be treated or controlled is retinal edema.

9.32. Use 9 or 9.1 wherein the condition to be treated or controlled is epilepsy.

9.33. Use 9 or 9.1 wherein the condition to be treated or controlled is retinal ischemia or other diseases of the eye associated with abnormalities in intraocular pressure and/or tissue hydration.

9.34. Use 9 or 9.1 wherein the condition to be treated or controlled is myocardial ischemia.

9.35. Use 9 or 9.1 wherein the condition to be treated or controlled is myocardial ischemia/reperfusion injury.

9.36. Use 9 or 9.1 wherein the condition to be treated or controlled is myocardial infarction.

9.37. Use 9 or 9.1 wherein the condition to be treated or controlled is myocardial hypoxia.

9.38. Use 9 or 9.1 wherein the condition to be treated or controlled is congestive heart failure.

9.39. Use 9 or 9.1 wherein the condition to be treated or controlled is sepsis.

9.40. Use 9 or 9.1 wherein the condition to be treated or controlled is a migraine.

9.41. Use 9 wherein the aquaporin is AQP2.

9.42. Use 9 or 9.41 wherein the condition to be treated is hyponatremia or excessive fluid retention, e.g., consequent to heart failure (HF), for example congestive heart failure, liver cirrhosis, nephrotic disorder, or syndrome of inappropriate antidiuretic hormone secretion (SIADH).

9.43. Use 9.42 further comprising one or more of restriction of dietary sodium, fluid and/or alcohol; and/or administration of one or more diuretics, vasopressin receptor antagonists, angiotensin converting enzyme (ACE) inhibitors, aldosterone inhibitors, angiotensin receptor blockers (ARBs), beta-adrenergic antagonists (beta-blockers), and/or digoxin.

9.44. Any of Use 9, et seq. wherein the compound of Formula I or formula 1a inhibits aquaporin activity, e.g., AQP2 and/or AQP4 activity, by at least 50% at concentrations of 10 micromolar or less, for example inhibits APQ2 and/or AQP4 activity by at least 50% at concentrations of 10 micromolar or less in an aquaporin-mediated cell volume change assay, e.g., is active in any of the assays of Method 10, et seq. infra.

9.45. Any of Use 9, et seq. wherein the duration of treatment with the phenylbenzamide is less than 21 days, e.g., less than 2 weeks, e.g., one week or less.

9.46. Any of Use 9, et seq. wherein the medicament is formulated for oral administration.

9.47. Any of Use 9, et seq. wherein the medicament is formulated for parenteral administration.

9.48. Use 9.47 wherein the medicament is formulated for intravenous administration.

A dose or method of administration of the dose of the present invention is not particularly limited. Dosages employed in practicing the present invention will of course vary depending, e.g. on the particular disease or condition to be treated, the particular compound used, the mode of administration, and the therapy desired. The compounds may be administered by any suitable route, including orally, parenterally, transdermally, or by inhalation. In stroke or other severely debilitating diseases or conditions, for example where the patient may be unconscious or unable to swallow, an IV infusion or IV bolus may be preferred. In general, satisfactory results, e.g. for the treatment of diseases as hereinbefore set forth are indicated to be obtained on oral administration at dosages of the order from about 0.01 to 15.0 mg/kg. In larger mammals, for example humans, an indicated daily dosage for oral administration will accordingly be in the range of from about 0.75 to 1000 mg per day, conveniently administered once, or in divided doses 2 to 3 times, daily or in sustained release form. Unit dosage forms for oral administration thus for example may comprise from about 0.2 to 75 or 150 mg, e.g. from about 0.2 or 2.0 to 50, 75, 100, 125, 150 or 200 mg of a Compound of the Invention, together with a pharmaceutically acceptable diluent or carrier therefor. When the medicament is used via injection (subcutaneously, intramuscularly or intravenously) the dose may be 0.25 to 500 mg per day by bolus or if IV by bolus or infusion.

Pharmaceutical compositions comprising compounds of Formula I or formula 1a may be prepared using conventional diluents or excipients and techniques known in the galenic art. Thus oral dosage forms may include tablets, capsules, solutions, suspensions and the like.

Methods of making and formulating compounds of Formula I or formula 1a are set forth in US 2010/0274051 A1, U.S. Pat. No. 7,700,655, and in U.S. Pat. No. 7,626,042, each incorporated herein by reference.

In a further embodiment, the invention provides a method, e.g., Method 10, for identification of specific aquaporin inhibitors, comprising measuring the response of an aquaporin-expressing cell population versus a control cell population to a hypertonic or hypotonic solution in the presence or absence of a test compound. For example the invention provides, e.g., 10.
- 10.1. Method 10 wherein the aquaporin-expressing cell population expresses AQP2 or AQP4.
- 10.2. Any of Method 10 or 10.1 wherein the cells are mammalian, e.g., transgenic CHO cells.
- 10.3. Any of Method 10, et seq. wherein the control cells express a transgenic transmembrane protein other than an aquaporin, e.g., CD81.
- 10.4. Any of Method 10, et seq. wherein the cells are exposed to a hypotonic environment for a period of time and at a concentration which causes most of the aquaporin-expressing cell population to burst in the absence of test compound, but not the control cell population, e.g. 3-8 minutes in water.
- 10.5. Method 10.4 wherein cell bursting is measured by a fluorescent signal that is produced by viable cells but not by burst cells, e.g., conversion of acetoxymethyl calcein (calcein-AM) to the fluorescent dye calcein.
- 10.6. Method 10.4 or 10.5 wherein the cells are exposed to a hypotonic environment, e.g., deionized water, for a period of 3-8 minutes, and then returned to normotonic environment (e.g. ca. 300 mOSM) then the proportion of viable cells is measured.
- 10.7. Any of Method 10, et seq. wherein the measurement of viability is the ability of the cells to convert acetoxymethyl calcein (calcein-AM) to the fluorescent dye calcein.
- 10.8. Any of the foregoing Methods 10.4, et seq. wherein a compound of Formula I as hereinbefore described, e.g., of formula 1a, is used as a positive control, which inhibits the aquaporin-expressing cell population from bursting in a hypotonic environment.
- 10.9. Any of the foregoing Methods 10.4-10.8 wherein a test compound is identified as having aquaporin-inhibitory activity when the aquaporin-expressing cell population is identified viable, e.g., by the ability of the cells to convert acetoxymethyl calcein (calcein-AM) to the fluorescent dye calcein, following an exposure in a presence of test compound to a hypotonic environment that renders the aquaporin-expressing cell population non-viable in the absence of test compound.
- 10.10. Any of Method 10 or 10.1-10.3 wherein the cells are exposed to a hypertonic environment for a period of time and at a concentration sufficient to cause the aquaporin-expressing cell population to shrink in the absence of test compound, e.g. 3-8 minutes at ca. 530 mOsm.
- 10.11. Method 10.9 wherein the shrinkage of the cells is measured by light scattering.
- 10.12. Any of Method 10.10, et seq. wherein the hypertonic environment is approximately 530 mOsm and the normotonic environment is approximately 300 mOsm.
- 10.13. Any of the foregoing Methods 10.10, et seq. wherein a compound of Formula I as hereinbefore described, e.g., of formula 1a, is used as a positive control, which inhibits the aquaporin-expressing cell population from shrinking in a hypertonic environment.
- 10.14. Any of the foregoing Methods 10.10, et seq. wherein a test compound is identified as inhibiting aquaporin activity by inhibiting the aquaporin-expressing cell population from shrinking in a hypertonic environment.
- 10.15. Any of the foregoing methods wherein a test compound is identified as inhibiting aquaporin activity.
- 10.16. Any of Method 10, et seq. wherein the aquaporin-expressing cell population expresses AQP2.
- 10.17. Any of Method 10, et seq. wherein the aquaporin-expressing cell population expresses AQP4.
- 10.18. Any of Method 10, et seq. wherein the test compound is a phenylbenzamide, e.g., of Formula I as hereinbefore described, e.g., of formula 1a.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

Example 1—Phenylbenzamide-AQP Structure-Activity Relationship

Figure 1A:
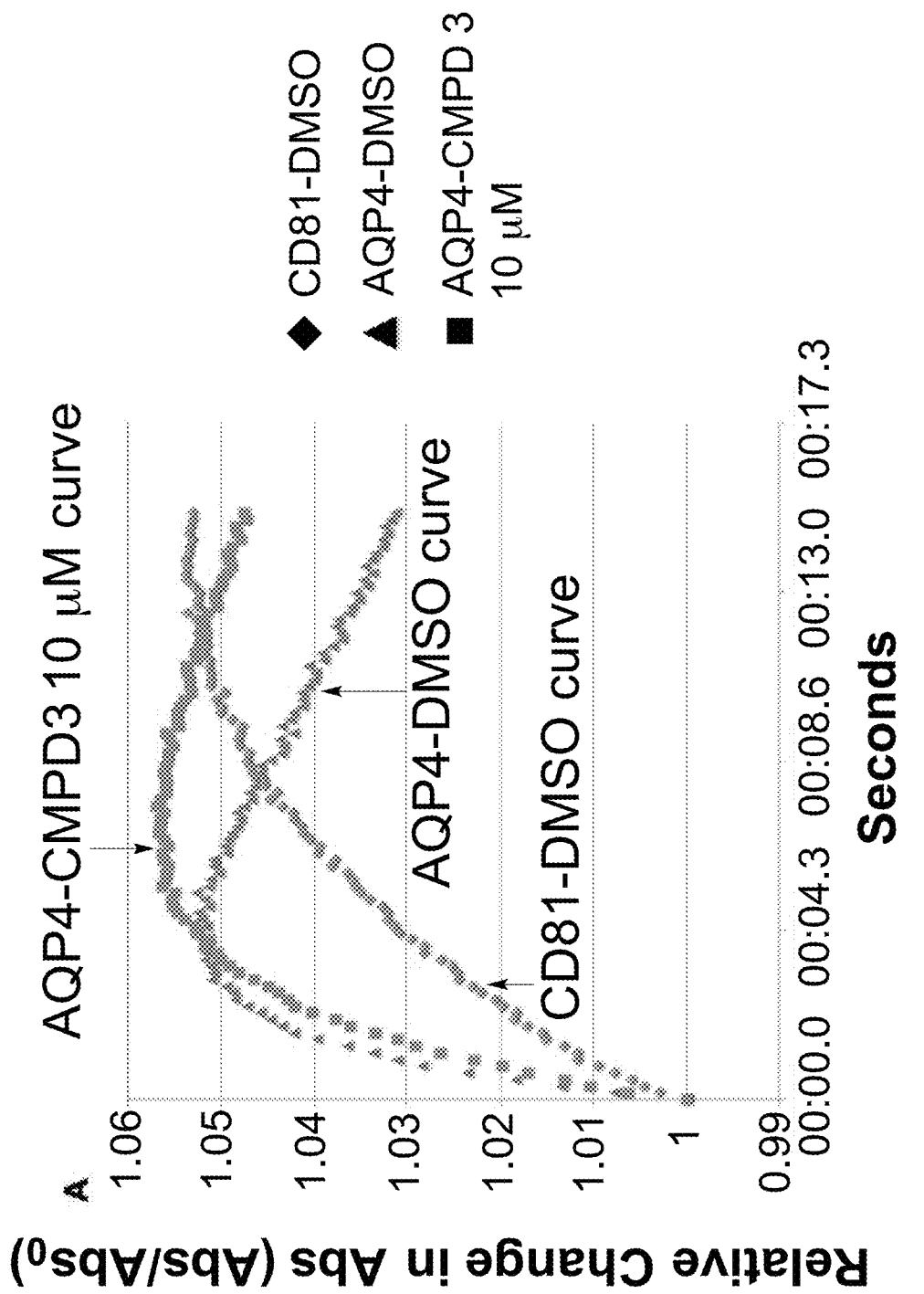
FIG. 1 depicts results of aquaporin-4 (FIG. 1A) and aquaporin-2 (FIG. 1B) mediated cell volume change assay, and the inhibitory effect of Compound 3 (compound of formula 1a where $R_1$, $R_3$ and $R_5$ are each chloro, and $R_2$, $R_4$ and $R_6$ are H) against these aquaporins.
Figure 1B:
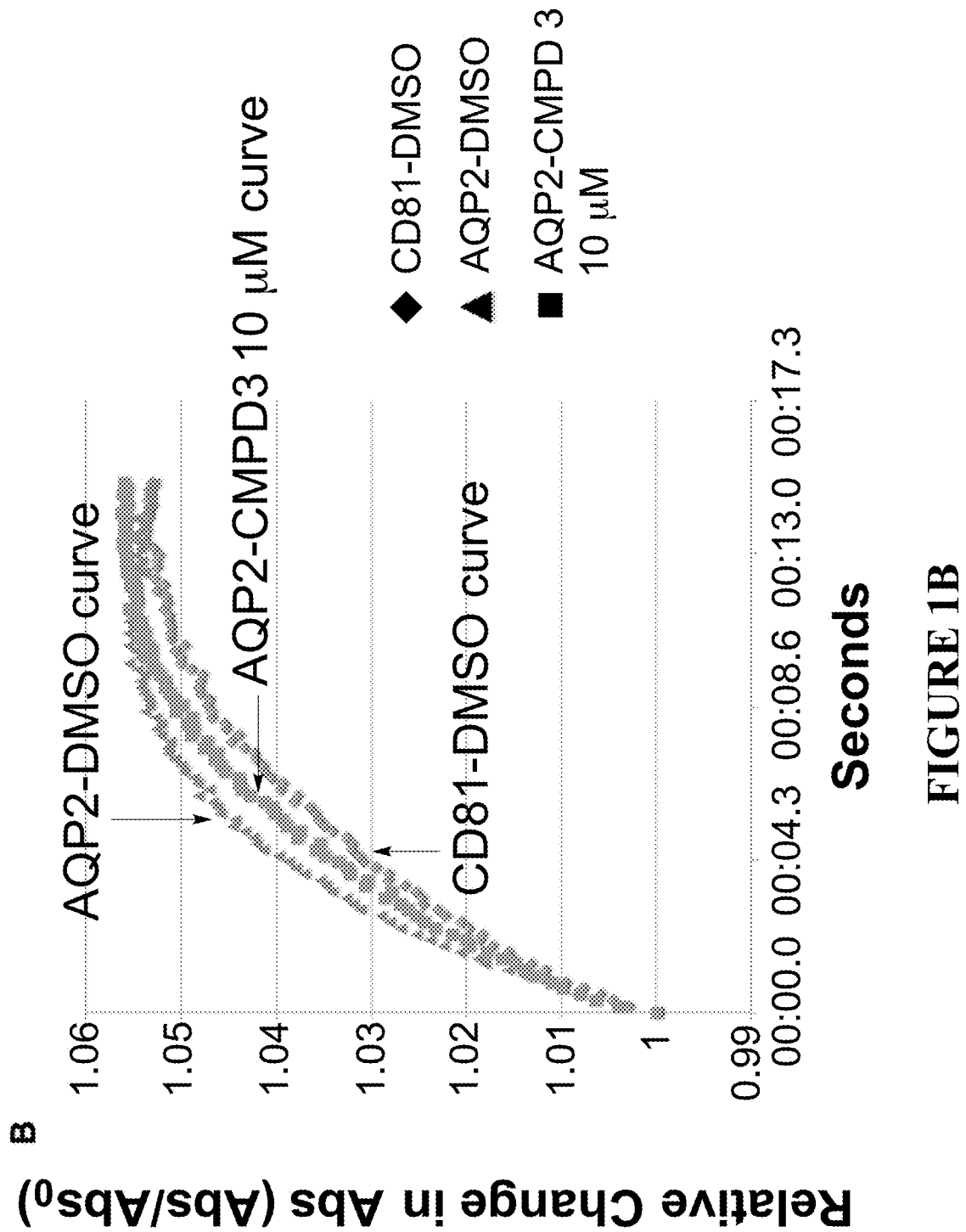

Structure activity relationships (SARs) are determined by assaying analogues of selected hits to guide chemistry for the preparation of new molecules to be tested for improved potency. For this iterative process we use a quantitative kinetic assay—the Aquaporin-Mediated Cell Volume Change Assa—in a 96-well multiplate reader. It detects changes in light scattering by a monolayer of CHO cells expressing the desired AQP as they shrink when exposed to hypertonic solution (300 mOsm→530 mOsm). FIG. 1 depicts the aquaporin-mediated cell volume change assay with AQP4 expressing cells (FIG. 1A) and AQP2 expressing cells (FIG. 1B). The cells expressing aquaporins shrink more rapidly than control cells, due to enhanced water flow, which shrinkage can be inhibited by a compound that inhibits the aquaporin.

In FIG. 1, aquaporin-expressing cells are shown in the presence of DMSO (triangles) or in the presence of the test compound (here, Compound 3) at 10 µM (squares), along with CHO-CD81 expressing control cells in the presence of DMSO (diamonds). Each curve represents an average of 16 wells in the 96-well plate.

In FIG. 1A, when the AQP4b cells treated with DMSO are exposed to hypertonic shock, the cells show rapid shrinking, giving a rise in light scattering (increasing relative change in absorbance, $Abs/Abs_0$) followed by a decay as cells detach from the plate. The CHO-AQP4b cell line shows a 4.5-fold increase in the rate of shrinking compared to CHO-CD81 control cells (fitted to a double exponential model). CHO-AQP4b cells treated with the Compound 3 analogue at 10 µM (squares) show a slower rate of shrinking (55% inhibition) as seen by characteristic 'unbending' of the light scattering curve. Similarly, FIG. 1B depicts an experiment comparing CHO-AQP2 treated with DMSO or with Compound 3 at 10 µM. Aquaporin-2 has a lower intrinsic water permeability than AQP4 as observed here. CHO-AQP2 cell lines treated with DMSO (FIG. 1B, triangles) show a 1.7-fold increase in the rate of shrinking compared to CHO-CD81 control cells (diamonds) also treated with DMSO (fitted to a double exponential model) (FIG. 1B). CHO-AQP2 cells treated with Compound 3 at 10 µM (squares) show a slower rate of shrinking (81% inhibition), when comparing the relative change in Abs ($Abs/Abs_0$) (FIG. 1B).

The data indicates that in this assay, Compound 3 is capable of significantly inhibiting AQP2 and AQP4 activity, e.g. by greater than 50%, at concentrations of 10 µM.

Example 2—Aquaporin Specificity of the Phenylbenzamide Compounds

Figure 2:
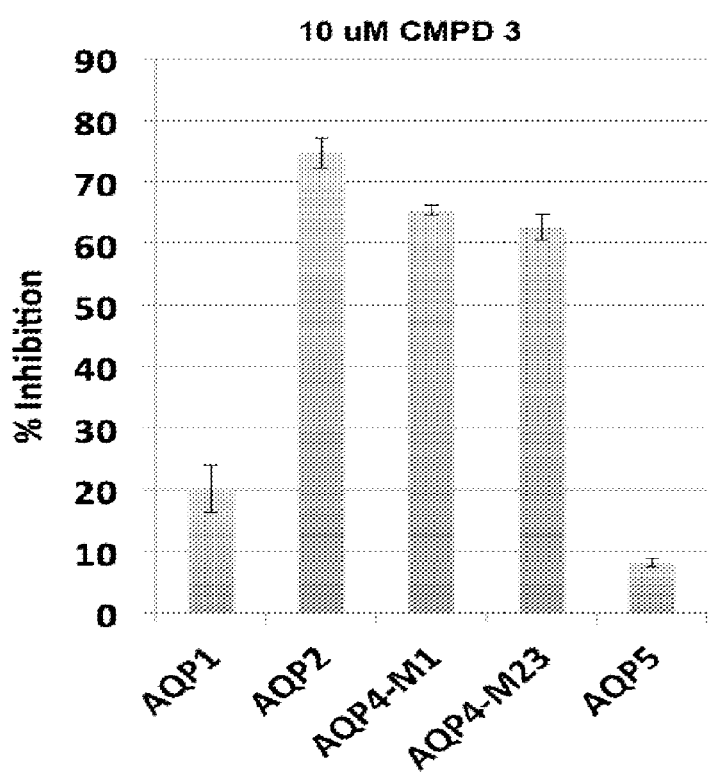
FIG. 2 depicts specificity of Compound 3 towards AQP-1, AQP-2, AQP-4-M1, AQP-4-M23, and AQP-5.

The specificity of the compounds is tested against the most closely related of the 13 known aquaporins: AQP1, AQP2, AQP5 and both splice variants of AQP4 (A and B). A stable CHO cell line is created for each of the above aquaporins and the inhibition of water permeability using the Aquaporin-Mediated Cell Volume Change Assay with 10 µM Compound 3 is tested. Compound 3 inhibits AQP2 and 4, while it poorly inhibits AQP1 and 5 (FIG. 2).

Example 3—Direct Drug-Target Interactions Between Phenylbenzamides and AQP4

Figure 3:
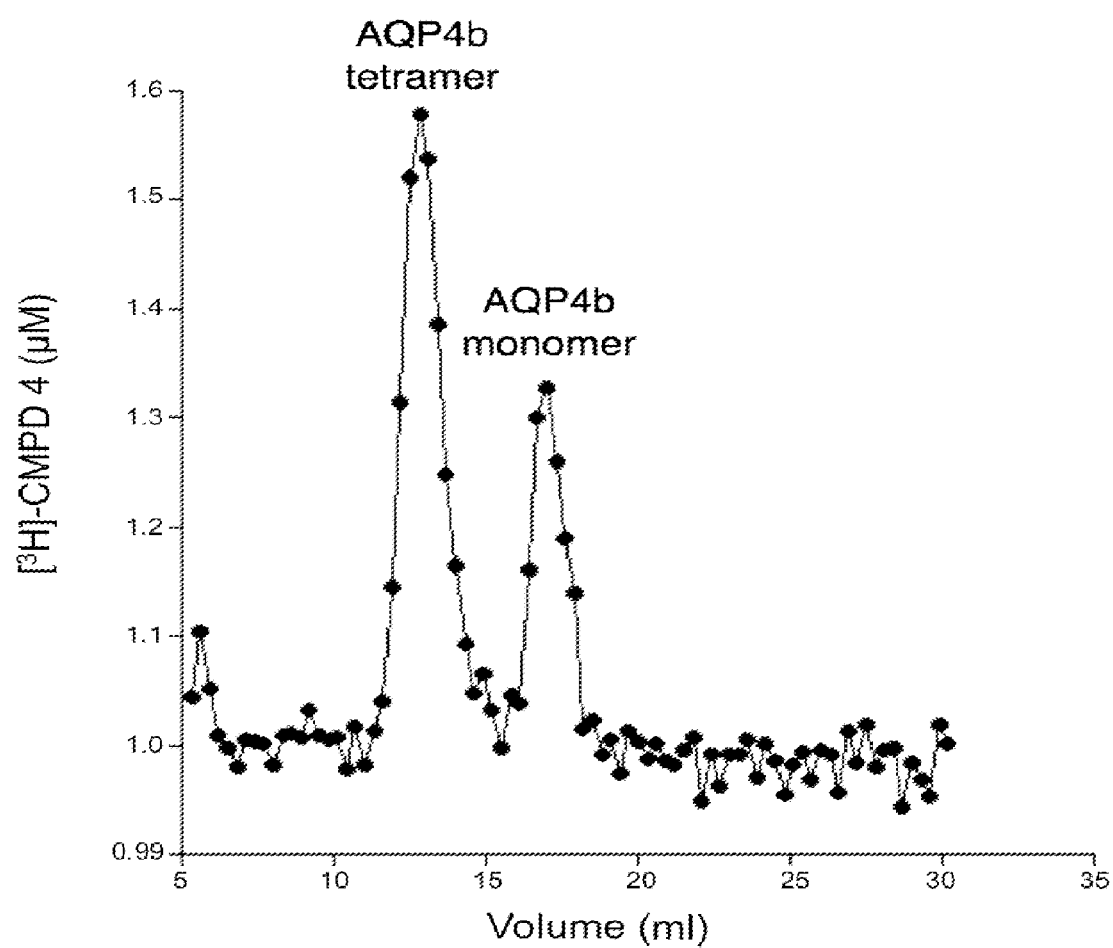
FIG. 3 depicts a Hummel-Dryer style assay for [3H]-labeled Compound 4 (compound of formula 1a where $R_1$, $R_3$ and $R_5$ are each trifluoromethyl, and $R_2$, $R_4$ and $R_6$ are H) binding to purified AQP4b.

To support the mechanism of action by which phenylbenzamides directly block AQP4, we perform in vitro binding studies using purified AQP4b and Compound 4 radiolabeled with $^3H$. Using a Hummel-Dryer style assay, a gel filtration column is equilibratrated with buffer containing detergent, to maintain solubility of AQP4b, and 1 µM [$^3H$]-Compound 4. AQP4b is diluted to 250 µM in this column buffer and incubated at RT for 30 min. The sample is then applied to the column, fractions collected and the presence of [$^3H$]-Compound 4 detected by liquid scintillation counting. FIG. 3 shows the elution profile of [$^3H$]-Compound 4 from the gel filtration column with the elution positions of tetrameric and monomeric AQP4b indicated. The rise in [$^3H$]-Compound 4 from a baseline value of 1 µM represents binding to each of these proteins. Although no monomeric AQP4b can be readily detected in our highly purified AQP4b by conventional means, this assay reveals the presence of a small, albiet vanishing, amount of monomer. The relative affinities for Compound 4 are ~100 µM and less than 1 µM for tetramer and monomer, respectively. This assay shows relatively weak binding of Compound 4 to solubilized AQP4b; nevertheless, it clearly demonstrates that this phenylbenzamide directly interacts with AQP4b.

Example 4—Pharmacological Proof-of-Concept

Mouse Water Toxicity Model—Survival Curves: The in vivo efficacies of the compounds are tested using the mouse water toxicity model, where a mouse is injected with water at 20% of its body weight. Manley, G. T. et al. *Aquaporin-4 deletion in mice reduces brain edema after acute water intoxication and ischemic stroke*. Nat Med 6, 159-163 (2000); Gullans, S. R. & Verbalis, J. G. *Control of brain volume during hyperosmolar and hypoosmolar conditions*. Annual Review of Medicine 44, 289-301 (1993). The resulting euvolemic hyponatremia rapidly leads to CE, making this a practical model to test an inhibitor of the CNS aquaporin, AQP4b.

Figure 4:
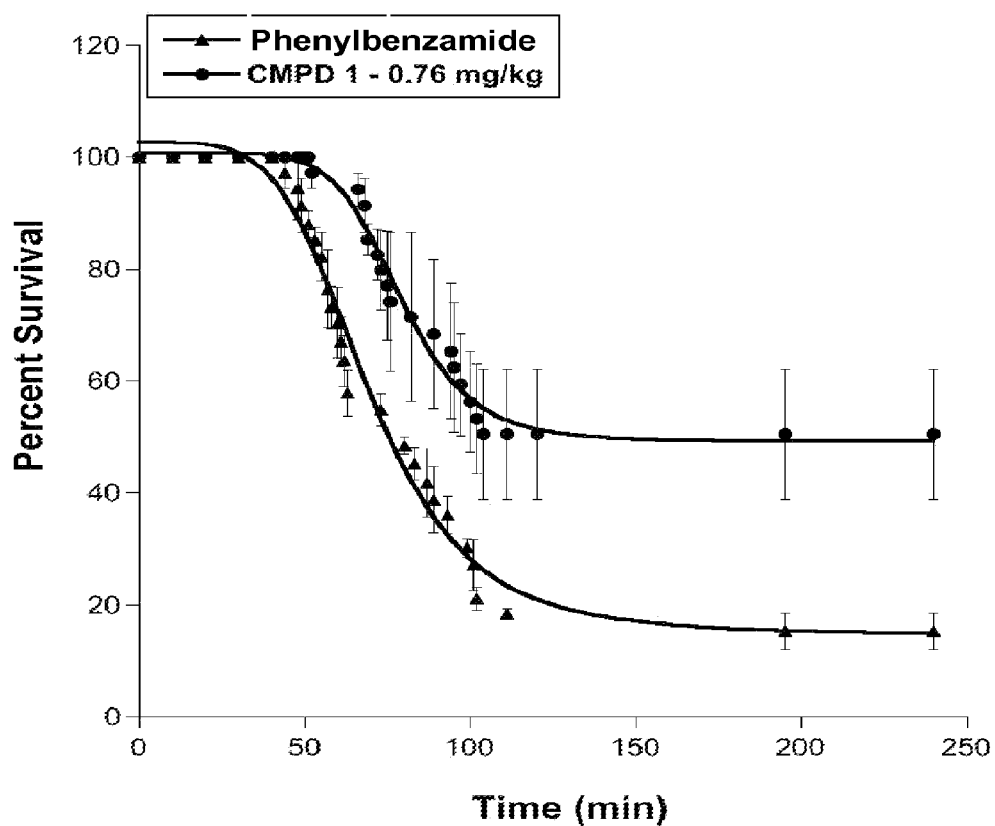
FIG. 4 depicts percent survival curves for the water toxicity mouse model using 0.76 mg/kg Compound 1 (compound of formula 1a where $R_1$ is chloro, $R_3$ and $R_5$ are each trifluoromethyl, and $R_2$, $R_4$ and $R_6$ are H).

The ability of mice to survive $H_2O$ toxicity is determined in three experiments using 10-12 mice each (16-19 weak old male/female). Deionized water is prepared for injection with either 0.39 mg/kg phenylbenzamide (placebo) or 0.76 mg/kg with test compound. FIG. 4 shows the combined results of these experiments (n=33 placebo, n=34 Compound 1). Percent survival of the Compound 1 cohorts improves 3.2 fold and the time to 50% survival for animals treated with Compound 1 is improved by roughly 52 min.

Figure 5:
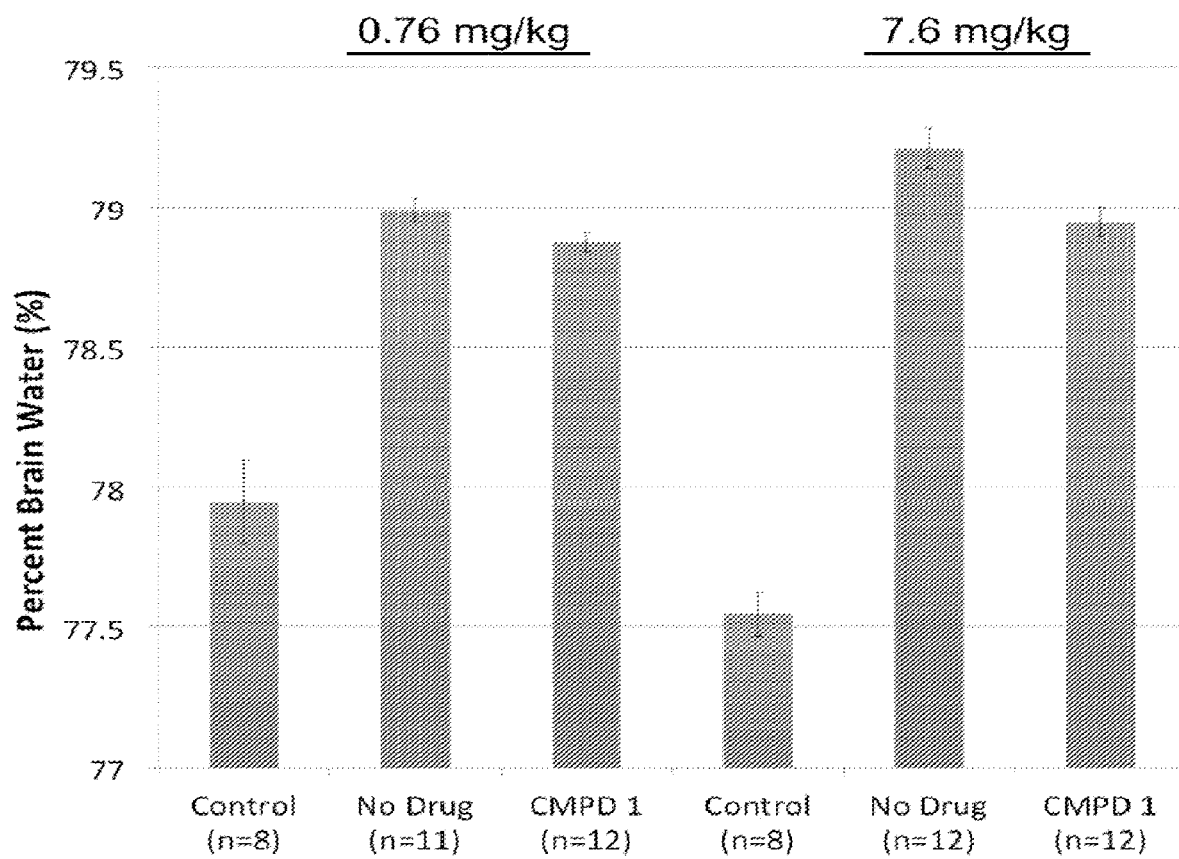
FIG. 5 depicts inhibition of cerebral edema formation in a mouse water toxicity model determined by brain water content using Compound 1.

Mouse Water Toxicity Model—Brain Water Content: Compounds are also tested for the ability to reduce CE in mice exposed to the water shock by examining brain water content. Mice are treated with a water bolus as described above, then sacrificed at 30 minutes. Brain water content is assessed by fresh/dry weight ratio, i.e. the brains are weighed immediately then desiccated in an oven at 100° C. for 24 h and dry weights measured (brain water percentage=100×dry weight/fresh weight). At 30 minutes, mice treated with 0.76 mg/kg and 7.6 mg/kg Compound 1 show an 11.2% and 15.9% reduction in CE, respectively (FIG. 5).

Mouse Water Toxicity Model—Brain Volume by Magnetic Resonance Imaging (MRI): MRI is used to measure changes in brain volume in response to water shock, using the water toxicity model. As described for the survival and brain water content studies above, mice are injected, IP, with a water bolus alone or water bolus and test compound at 0.76 mg/kg, and changes in brain volume as detected by MRI are monitored. Mouse brain volumes are assessed using MRI scans collected with a 9.4T Bruker Biospec MRI scanner at the Case Center for Imaging Research at Case Western Reserve University. This imaging method is found to provide sufficient contrast and resolution to sensitively detect changes in total brain volume in the mouse water toxicity model for cerebral edema. High resolution T2-weighted sagittal scans (resolution=0.1 mm×0.1 mm×0.7 mm) of the mouse head are obtained prior to water injection, 5.67 min post water injection, and then every 5.2 minutes until the animal expires from the water loading. Each scan contains twenty-five 0.7 mm contiguous imaging slices of which 14-15 slices contain a portion of the brain. The cross sectional area of the brain in each imaging slice is measured by manual region-of-interest selection using ImageJ. Brain volumes are then calculated for each scan by summing the individual cross sectional brain areas and multiplying by the slice thickness (0.7 mm).

Figure 6:
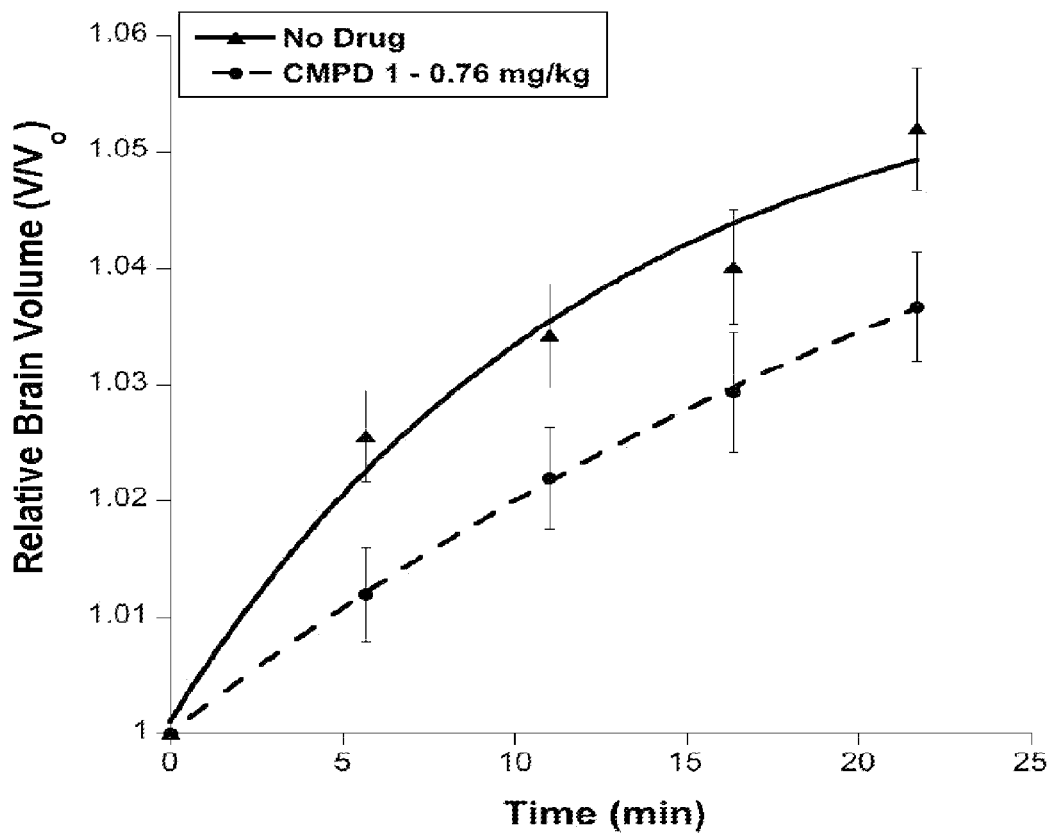
FIG. 6 depicts inhibition of cerebral edema formation by Compound 1 in the mouse water toxicity model by MRI brain volume analysis, with n=14 mice/treatment. A time course of edema formation is shown comparing no drug vs. Compound 1 at 0.76 mg/kg. The first time point at 5.67 min coincides with the scan slice at the middle of the brain during the first post-injection scan. Other time points are placed in a similar manner. The data is fitted to a single exponential equation.

Treatment with Compound 1 at 0.76 mg/kg reduces the rate of CE development from 0.081 to 0.032 $min^{-1}$ (or 2.5-fold) fit to a single exponential model (FIG. 6). Also, the extent of CE during the period of observation is reduced (FIG. 6). Moreover, plasma levels in the same assay are found to range between 0.03-0.06 µg as determined by LC-MS/MS (performed at Lerner Center, Cleveland Clinic, Cleveland, OH) and are sufficient to show efficacy in this model for CE.

The brain volume by magnetic resonance imaging experiment is also conducted with phenylbenzamide (0.39 mg/kg) and Compound 4 (0.83 mg/kg). Compound 4 reduces the rate of CE development from 0.081 to 0.022 $min^{-1}$ (Table 1). Phenylbenzamide fails to show reduction in the rate of CE in mice (Table 1).

TABLE 1

Efficacy of compounds on CE formation in the mouse water toxicity model

| Compound | AQP inhibition Cell-Based Assay (%) | Cerebral Edema Rate by MRI ($min^{-1}$) |
|---|---|---|
| No Drug | 0 | 0.081 |
| Compound 1 | 47.9 | 0.032 |
| Phenylbenzamide | 4.5 | 0.096 |
| Compound 4 | 38.9 | 0.022 |

For no drug and Compound 1, n=14 mice each. For phenylbenzamide and Compound 4, n=12 mice each.

Example 5—High Throughput Screening Assay

Under hypotonic shock, both untransfected cells and cells expressing an unrelated transmembrane protein (CD81, at levels equivalent to AQP4b) swell slowly but remain intact. These observations are used to develop our high-throughput screening assay (HTS).

After hypotonic shock in a 384 well plate format, we return osmolality to normal (300 mOSM) by adding 2× concentrated phosphate buffered saline supplemented to 2 µM with a nonfluorescent acetoxymethyl derivative of calcein (calcein-AM) to each well. Intact cells take up calcein-AM and convert it to the fluorescent dye calcein—giving a quantitative measure of the remaining intact cells. Burst cells do not convert the precursor to the dye. Water uptake by AQP4-expressing cells is relatively rapid, with most test cells bursting within 4 min of hypotonic shock, whereas most cells expressing CD81 remain viable after 8 min. Intracellular conversion of calcein-AM provides a strong and easily detectable signal at 535 nM in our assay (FIG. 7).

Calcein fluorescence end-point assay: Cells are seeded 24 hr before assay to reach 100% confluence. Culture medium was replaced with $H_2O$ for 5:30 min (osmotic shock). Osmolality is then normalized with the addition of 2× PBS plus 2 µM calcein-AM. Cells are then incubated at 37° C. for an additional 30 min and fluorescence measured on a plate-reader. Rows 1-22 are seeded with CHO-AQP4 cells, and rows 23-24, with CHO-CD81 cells (384 well plate). Note, all plate edges are discarded. Relative Fluorescence Intensity is calculated as the fluorescence intensity (FI) of each well divided by the mean FI of AQP4 cells treated with DMSO (control). Criteria for a successful assay: coefficients of variation (CVs)<15%, and Z-factors >0.5. Statistical analysis shows that 5.5 min of osmotic shock provides the optimal signal-to-noise ratio.

TABLE 2

Statistics for endpoint 'calcein' assay in FIG. 7; 5:30 min time point shown:

| | Mean | StDev | CV | Z' | S/B |
|---|---|---|---|---|---|
| AQP4 | 581618 | 66311 | 11% | 0.629 | 5.0 |
| CD81 | 2910106 | 221240 | 8% | | |

As will be observed, the signal for the CD81 cells is ca. 5× higher than the signal for the APQ4 cells, because by 5.5 mins, most of the AQP4 cells have burst, while most of the CD81 cells remain intact. Inhibition of AQP4 would therefore be expected to provide a higher signal, more like the CD81 cells.

This assay is applied in a pilot screen of the MicroSource GenPlus 960 and the Maybridge Diversity™ 20k libraries (approximately 21,000 compounds tested, each compound at 10-20 µM).

From this assay, a specific chemical series is identified, phenylbenzamides, which represents 3 out of the top 234 hits.

Hits from the HTS are validated using the same assay using a different plating arrangement. In FIG. 8, we show this validation assay used to examine Compound 3. Cells are seeded in a 96 well multiplate format with the plates edges omitted (lanes 1 and 24) and an entire column (n=16) is used to test the ability of a compound to block AQP4-mediated cell bursting upon $H_2O$ shock. CHO cells expressing CD81 are seeded in lanes 2-3 as a control, and CHO cells expressing AQP4, in lanes 4-23. Cells are treated with 0.1% DMSO in 10% FBS, DMEM (even numbered columns) or 10 µM Compound 1 (odd number columns) in 0.1% DMSO, 10% FBS, DMEM for 30 minutes. The cells are shocked with $H_2O$ for 5:30 minutes, then osmolality returned to 300 mOSM in the presence of 1 µM calcein-AM, as described above. The cells are incubated at 37° C. for 30 minutes and the relative fluorescence measured (ex 495/em 535 nM) on a fluorescence multiplate reader. The data in FIG. 8 represents the average relative fluorescence units (RFU±SEM, n=16).

Example 6—Water Toxicity Model for CE: Intracranial Pressure (ICP)

ICP is monitored using a Samba 420 Sensor, pressure transducer, with a Samba 202 control unit (Harvard Apparatus, Holliston, MA). This ICP monitoring system consists of a 0.42 mm silicon sensor element mounted on an optical fiber. A 20-gauge syringe needle is implanted through the cisterna magna to a depth of ~1 cm. The needle then acts as a guide for insertion of the Samba Sensor and the site of implantation and the open end of the needle are sealed with 100% silicone sealant. A baseline ICP reading is established followed by a water bolus IP injection (20% weight of animal) with or without Compound 1. ICP is monitored until the animal expires from the water load.

Adjusting for the slight rise in ICP observed in the animals when they are monitored without the water bolus injection (FIG. 9, No Water Toxicity), Compound 1 at 0.76 mg/kg reduces the relative rate of ICP rise by 36%, from $3.6 \times 10^{-3}$ $min^{-1}$ to $2.3 \times 10^{-3}$ $min^{-1}$ (n=6 mice/treatment, mean±SEM).

Example 7—Conversion of Compound 5 to Compound 1

Plasma or serum levels of Compound 1 are measured by LC-MS/MS at the Mass Spectrometry 11 Core facility at the Lerner Research Institute of the Cleveland Clinic Foundation. Measurements are taken at 15 minutes and 24 hours after a 10 mg/kg i.p. loading dose and 1 mg/ml at 8 µl/h maintenance dose (delivered by an Alzet i.p. osmotic pump, Durect Corp., Cupertino, CA) of Compound 5 (n=5 mice/time point, mean±SEM) (FIG. 10). After initial processing to remove proteins (75% acetonitrile extraction), Compound 3 is introduced to improve quantitation using multiple reaction monitoring (MRM). Samples are analyzed by tandem LC-MS/MS using C18 reversed-phase chromatography and mass analysis with a triple-quadrapole mass spectrometer. The LC method is sufficient to separate Compound 1 from Compound 3 and subsequent MRM gave reliable quantitation with a linear response from 0.004-0.4 ng of Compound 1 for its most abundant daughter ion. The dashed line in FIG. 10 is the relative effective plasma concentration of Compound 1 observed in the mouse water toxicity model. Inclusion of an Alzet osmotic pump (Durect Corp., Cupertino, CA) containing Compound 5 in the peritoneum was sufficient, in conjunction with an initial loading dose, to sustain Compound 1 above the expected efficacious plasma concentration of 20 ng/ml for 24 hours (FIG. 10).

The solubility of Compound 1 in water is 3.8 µg/ml. The solubility of Compound 5 in water is 1 mg/ml. Initial experiments show rapid bioconversion of Compound 5 to Compound 1 when added to mouse plasma in vitro. Less than 5 minutes at 20° C. is sufficient to render Compound 5 undetectable. In addition, Compound 1 is undetectable in plasma samples taken from mice injected IP with Compound 5. Instead, Compound 1 is detected at a concentration consistent with good bioavailability and near-complete conversion of Compound 5. With compound 5, doses of 10 mg/kg and IP injection volumes in saline (0.5 ml for a 30 g mouse), that give serum concentrations of Compound 1 in excess of 400 ng/ml (FIG. 10) can be used. Key PK parameters for Compound 5 are: rate of absorption 0.12 $min^{-1}$; rate of elimination 0.017 $min^{-1}$.

Example 8—Animal Stroke Model

Most ischemic strokes 80%) occur in the region of the middle cerebral artery (MCA). To mimic this injury in mice, an intraluminal monofilament model of middle cerebral artery occlusion (MCAo) is used. Occlusion is achieved by inserting a surgical filament into the external carotid artery (ECA) and threading it forward into the internal carotid artery (ICA) until the tip blocks the origin of the MCA. The resulting cessation of blood flow gives rise to subsequent brain infarction in the MCA territory (Longa, E. Z. et al., *Reversible Middle Cerebral Artery Occlusion Without Craniectomy in Rats*, Stroke, 20, 84-91 (1989)). This technique is used to study a temporary occlusion in which the MCA was blocked for one hour. The filament is then removed allowing reperfusion to occur for 24 hours before the animal's brain was imaged using T2-weighted scans in a 9.4T Bruker MRI scanner at the Case Center for Imaging Research (FIG. 11). FIG. 11 shows a single slice from a T2-weighted MR image depicting the center of the brain showing cerebral cortex, hippocampus, thalamus, amygdala and hypothalamus for a "Normal" mouse (left panels) and a mouse which receives MCAo for one hour followed by 24 hours of reperfusion (right panels). Dashed lines mark the midline of the brain and show a large shift in the MCAo brain due to cerebral edema. Solid line highlights the region of infarct in the MCAo brain.

Survival—Mice are treated with Compound 5 using a 2 mg/kg i.p. loading dose and 1 mg/ml at 8 µl/h maintenance dose (delivered by an i.p. osmotic pump) of Compound 5, or given saline (controls; n=17) using an identical approach. In this model, we observed a 29.4% improvement in overall survival at 24 h when animals are treated with Compound 5 ($X^2(1)$=4.26; P<0.05).

Cerebral Edema—Mice are given saline or treated with Compound 5 by multi-dosing at 5 mg/kg i.p. every three hours (n=8 per treatment). This dosing regimen is sufficient to maintain a plasma concentration of Compound 1>10 ng/ml for the duration of the study. Ipsilateral and contralateral hemispheric volume is measured from the T2-weighted MR images of mice 24 hours post-icus. Relative change in hemispheric volume is calculated as a percent of the difference between ipsilateral brain volume ($V_i$) and contralateral brain volume ($V_c$) relative to the contralateral brain volume (Percent Change in Hemispheric Brain Volume=$((V_i-V_c)/V_c) \times 100\%$.

Control animals show swelling in the ipsilateral hemisphere with a relative change in ipsilateral brain volume of 13.4%±1.9%, while animals given Compound 5 show a 4.2±1.7% change (P=0.003, ±SEM, see FIG. 12). This represents a 3.2-fold reduction in brain swelling after MCAo.

Neurological Outcome—In the same experiment as above, animals are scored for neurological outcome on a simple 5 point scale described in Manley, G. T. et al., *Aquaporin-4 Deletion in Mice Reduces Brain Edema After Acute Water Intoxication and Ischemic Stroke*, Nature Medicine, 6, 159-163 (2000). An improvement in neurological outcome is observed for animals given Compound 5. Control animals have an average neurological score of 2.77±0.66, while animals given Compound 5 have an average score of 0.88±0.31 (FIG. 13, inset, P=0.025, n=9 per treatment). Animals given Compound 5 did not progress into a state of severe paralysis or death.

The data from the MCAo stroke model together with the water toxicity (brain edema) model link the pharmacology of Compound 5/Compound 1 with improved outcomes in stroke.

The invention claimed is:

1. A method of treating or controlling cytotoxic cerebral edema consequent to an ischemic stroke in a human patient in need thereof, wherein the method comprises administering to the human patient a phenylbenzamide of formula 1a:

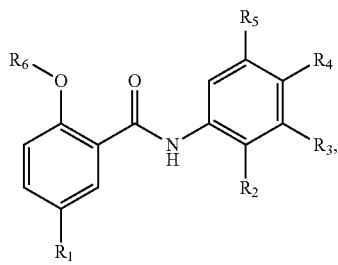

wherein $R_1$ is selected from trifluoromethyl, chloro, fluoro, and bromo;

$R_3$ and $R_5$ are the same or different and selected from trifluoromethyl, chloro, fluoro, and bromo;

$R_2$ and $R_4$ are both H; and $R_6$ is selected from H and physiologically hydrolysable and acceptable acyl;

in free or pharmaceutically acceptable salt form, and treating the human patient with intravenous thrombolysis and/or mechanical clot removal.

2. The method of claim 1, wherein $R_1$ is selected from chloro and bromo; $R_3$ and $R_5$ are both trifluoromethyl; and $R_2$, $R_4$ and $R_6$ are all H.

3. The method of claim 1, wherein $R_6$ is H.

4. The method of claim 1, wherein $R_1$, $R_3$ and $R_5$ are each trifluoromethyl, and $R_2$, $R_4$ and $R_6$ are each H.

5. The method of claim 1, wherein $R_6$ is a phosphono group, which may be substituted or unsubstituted.

6. The method of claim 1, wherein the phenylbenzamide is selected from:

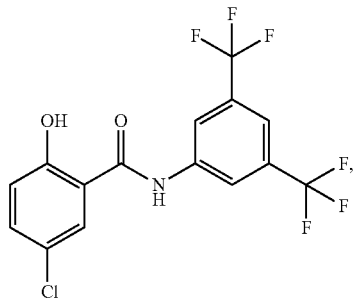

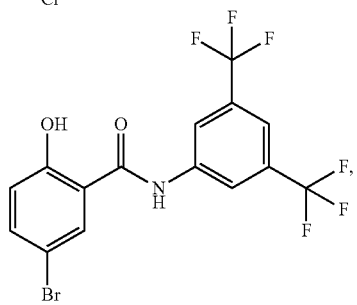

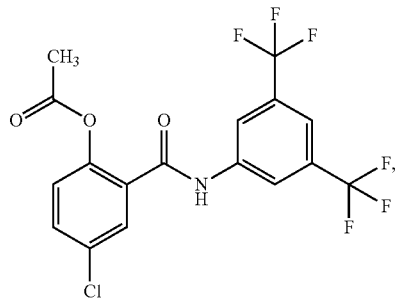

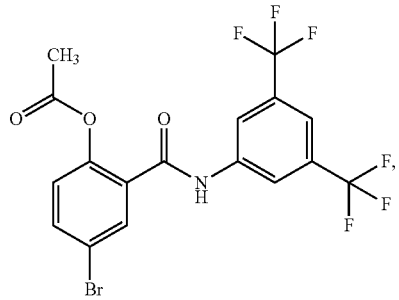

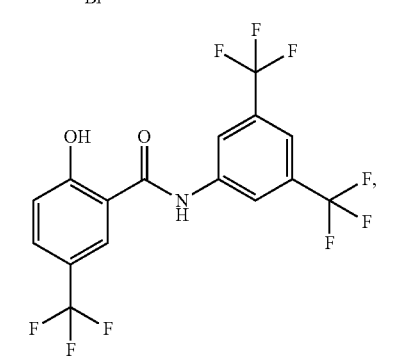

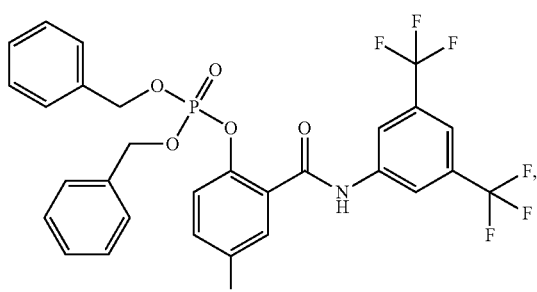

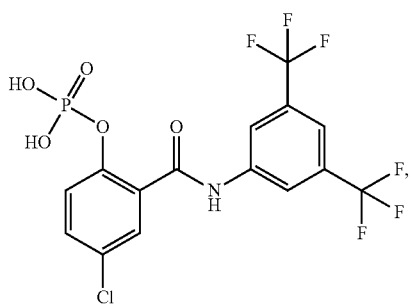

-continued

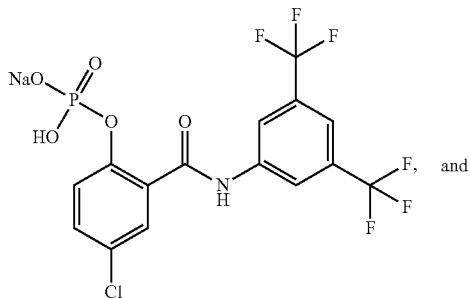

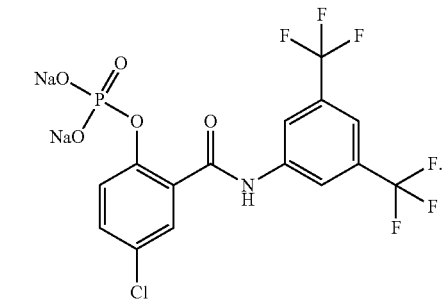

7. The method of claim 1, wherein the phenylbenzamide is:

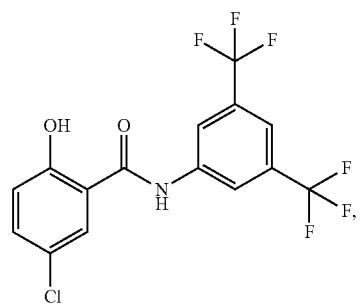 [SMILES: O=C(Nc1cc(C(F)(F)F)cc(C(F)(F)F)c1)c1cc(Cl)ccc1O]

in free or pharmaceutically accepable salt form.

8. The method of claim 1, wherein the phenylbenzamide is:

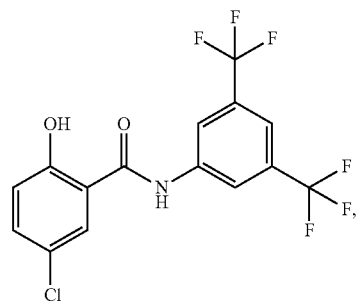 [SMILES: O=C(Nc1cc(C(F)(F)F)cc(C(F)(F)F)c1)c1cc(Cl)ccc1O]

in free form.

9. The method of claim 1, wherein the phenylbenzamide is:

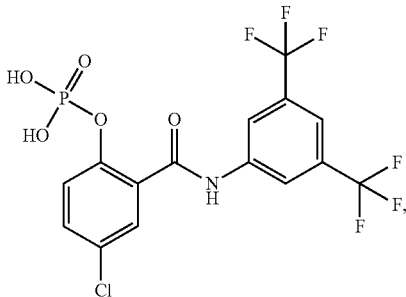 [SMILES: O=C(Nc1cc(C(F)(F)F)cc(C(F)(F)F)c1)c1cc(Cl)ccc1OP(=O)(O)O]

in free or pharmaceutically acceptable salt form.

10. The method of claim 1, wherein the method comprises treating the human patient with intravenous thrombolysis and the intravenous thrombolysis is with rtPA.

11. The method of claim 7, wherein the method comprises treating the human patient with intravenous thrombolysis and the intravenous thrombolysis is with rtPA.

12. The method of claim 8, wherein the method comprises treating the human patient with intravenous thrombolysis and the intravenous thrombolysis is with rtPA.

13. The method of claim 9, wherein the method comprises treating the human patient with intravenous thrombolysis and the intravenous thrombolysis is with rtPA.

14. The method of claim 7, wherein the phenylbenzamide, in free or pharmaceutically acceptable salt form, is administered within 12 hours of the stroke.

15. The method of claim 8, wherein the phenylbenzamide, in free form, is administered within 12 hours of the stroke.

16. The method of claim 9, wherein the phenylbenzamide, in free or pharmaceutically acceptable salt form, is administered within 12 hours of the stroke.

17. The method of claim 7, wherein the phenylbenzamide, in free or pharmaceutically acceptable salt form, is administered within 6 hours of the stroke.

18. The method of claim 8, wherein the phenylbenzamide, in free form, is administered within 6 hours of the stroke.

19. The method of claim 9, wherein the phenylbenzamide, in free or pharmaceutically acceptable salt form, is administered within 6 hours of the stroke.

20. The method of claim 11, wherein the phenylbenzamide, in free or pharmaceutically acceptable salt form, is administered within 12 hours of the stroke.

21. The method of claim 12, wherein the phenylbenzamide, in free form, is administered within 12 hours of the stroke.

22. The method of claim 13, wherein the phenylbenzamide, in free or pharmaceutically acceptable salt form, is administered within 12 hours of the stroke.

23. The method of claim 11, wherein the phenylbenzamide, in free or pharmaceutically acceptable salt form, is administered within 6 hours of the stroke.

24. The method of claim 12, wherein the phenylbenzamide, in free form, is administered within 6 hours of the stroke.

25. The method of claim 13, wherein the phenylbenzamide, in free or pharmaceutically acceptable salt form, is administered within 6 hours of the stroke.

* * * * *